(12) United States Patent
Deem et al.

(10) Patent No.: US 9,149,331 B2
(45) Date of Patent: *Oct. 6, 2015

(54) METHODS AND APPARATUS FOR REDUCING SWEAT PRODUCTION

(75) Inventors: Mark E. Deem, Mountain View, CA (US); Hanson Gifford, Woodside, CA (US); Steven Kim, Los Altos, CA (US); Alexey Salamini, San Francisco, CA (US)

(73) Assignee: MIRAMAR LABS, INC., Santa Clara, CA (US)

( * ) Notice: Subject to any disclaimer, the term of this patent is extended or adjusted under 35 U.S.C. 154(b) by 630 days.

This patent is subject to a terminal disclaimer.

(21) Appl. No.: 12/450,859

(22) PCT Filed: Apr. 18, 2008

(86) PCT No.: PCT/US2008/060935
§ 371 (c)(1), (2), (4) Date: Oct. 16, 2009

(87) PCT Pub. No.: WO2008/131302
PCT Pub. Date: Oct. 30, 2008

(65) Prior Publication Data
US 2010/0049178 A1    Feb. 25, 2010

Related U.S. Application Data

(60) Provisional application No. 60/912,899, filed on Apr. 19, 2007, provisional application No. 61/013,274, filed on Dec. 12, 2007, provisional application No. 61/045,937, filed on Apr. 17, 2008.

(51) Int. Cl.
*A61B 18/18* (2006.01)
*A61B 18/02* (2006.01)
(Continued)

(52) U.S. Cl.
CPC ............. *A61B 18/18* (2013.01); *A61B 18/02* (2013.01); *A61B 18/06* (2013.01); *A61B 18/082* (2013.01);
(Continued)

(58) Field of Classification Search
CPC ................. A61B 18/06; A61B 18/082
USPC ................. 606/10, 1, 41; 604/141
See application file for complete search history.

(56) References Cited

U.S. PATENT DOCUMENTS 2,407,690 A    9/1946 Southworth
3,307,553 A    3/1967 Liebner
(Continued)

FOREIGN PATENT DOCUMENTS

EP    0139607 B1    4/1990
EP    0370890 B1    11/1995
(Continued)

OTHER PUBLICATIONS

Abraham et al.; Monopolar radiofrequency skin tightening; Facial Plast Surg Clin N Am; 15(2); pp. 169-177; May 2007.
(Continued)

*Primary Examiner* — Tuan Nguyen
(74) *Attorney, Agent, or Firm* — Shay Glenn LLP

(57) ABSTRACT

Methods and apparatuses are provided for reducing sweat production via, for example, the removal, disablement, and incapacitation of sweat glands in the epidermis, dermis and subdermal tissue regions of a patient. In one embodiment, a method of treating a patient is provided which involves identifying a patient having a condition of excessive sweating, positioning an energy delivery device proximate to a skin tissue of the patient and delivering energy to sweat glands to halt secretion of sweat. The energy delivery device may include microwave delivery devices, RF delivery devices, and cryogenic therapy devices. Some embodiments may include using a cooling element for avoiding destruction of non-target tissue and/or a suction device to localize treatment at specific portions of the skin fold.

12 Claims, 57 Drawing Sheets

(51) Int. Cl.

| | | |
|---|---|---|
| A61B 18/06 | (2006.01) | |
| A61B 18/08 | (2006.01) | |
| A61B 18/14 | (2006.01) | |
| A61N 1/40 | (2006.01) | |
| A61N 5/02 | (2006.01) | |
| A61N 5/06 | (2006.01) | |
| A61N 7/00 | (2006.01) | |
| A61B 18/20 | (2006.01) | |
| A61B 19/00 | (2006.01) | |
| A61B 17/00 | (2006.01) | |
| A61B 18/00 | (2006.01) | |
| A61F 7/00 | (2006.01) | |
| A61N 7/02 | (2006.01) | |

(52) U.S. Cl.
CPC ............ *A61B 18/14* (2013.01); *A61B 18/1442* (2013.01); *A61B 18/1477* (2013.01); *A61B 18/1815* (2013.01); *A61N 1/406* (2013.01); *A61N 5/02* (2013.01); *A61N 5/062* (2013.01); *A61N 7/00* (2013.01); *A61B 18/20* (2013.01); *A61B 19/5225* (2013.01); *A61B 2017/00106* (2013.01); *A61B 2018/00005* (2013.01); *A61B 2018/0016* (2013.01); *A61B 2018/0022* (2013.01); *A61B 2018/00023* (2013.01); *A61B 2018/00029* (2013.01); *A61B 2018/00041* (2013.01); *A61B 2018/00291* (2013.01); *A61B 2018/00452* (2013.01); *A61B 2018/00476* (2013.01); *A61B 2018/00577* (2013.01); *A61B 2018/00613* (2013.01); *A61B 2018/00642* (2013.01); *A61B 2018/00702* (2013.01); *A61B 2018/00738* (2013.01); *A61B 2018/00779* (2013.01); *A61B 2018/00785* (2013.01); *A61B 2018/00791* (2013.01); *A61B 2018/00875* (2013.01); *A61B 2018/0262* (2013.01); *A61B 2018/0281* (2013.01); *A61B 2018/143* (2013.01); *A61F 2007/0075* (2013.01); *A61N 7/02* (2013.01); *A61N 2005/0651* (2013.01); *A61N 2005/0659* (2013.01); *A61N 2005/0662* (2013.01); *A61N 2007/0008* (2013.01)

(56) References Cited

U.S. PATENT DOCUMENTS

| | | |
|---|---|---|
| 3,527,227 A | 9/1970 | Fritz |
| 3,693,623 A | 9/1972 | Harte et al. |
| 3,845,267 A | 10/1974 | Fitzmayer |
| 4,069,827 A | 1/1978 | Dominy |
| 4,095,602 A | 6/1978 | Leveen |
| 4,108,147 A | 8/1978 | Kantor |
| 4,140,130 A | 2/1979 | Storm, III |
| 4,174,713 A | 11/1979 | Mehl |
| 4,190,053 A | 2/1980 | Sterzer |
| 4,190,056 A | 2/1980 | Tapper et al. |
| 4,197,860 A | 4/1980 | Sterzer |
| 4,228,809 A | 10/1980 | Paglione |
| 4,375,220 A | 3/1983 | Matvias |
| 4,378,806 A | 4/1983 | Henley-Cohn |
| 4,388,924 A | 6/1983 | Weissman et al. |
| 4,397,313 A | 8/1983 | Vaguine |
| 4,397,314 A | 8/1983 | Vaguine |
| 4,446,874 A | 5/1984 | Vaguine |
| 4,528,991 A | 7/1985 | Dittmar et al. |
| 4,589,424 A | 5/1986 | Vaguine |
| 4,597,379 A | 7/1986 | Kihn et al. |
| 4,614,191 A | 9/1986 | Perler |
| 4,617,926 A | 10/1986 | Sutton |
| 4,632,128 A | 12/1986 | Paglione et al. |
| 4,641,649 A | 2/1987 | Walinsky et al. |
| 4,669,475 A | 6/1987 | Turner |
| 4,672,980 A | 6/1987 | Turner |
| 4,690,156 A | 9/1987 | Kikuchi et al. |
| 4,702,262 A | 10/1987 | Andersen et al. |
| 4,744,372 A | 5/1988 | Kikuchi et al. |
| 4,747,416 A | 5/1988 | Kikuchi et al. |
| 4,800,899 A | 1/1989 | Elliott |
| 4,825,880 A | 5/1989 | Stauffer et al. |
| 4,841,989 A | 6/1989 | Kikuchi et al. |
| 4,841,990 A | 6/1989 | Kikuchi et al. |
| 4,860,752 A | 8/1989 | Turner |
| 4,881,543 A | 11/1989 | Trembly et al. |
| 4,891,483 A | 1/1990 | Kikuchi et al. |
| 4,945,912 A | 8/1990 | Langberg |
| 4,974,587 A | 12/1990 | Turner et al. |
| 5,059,192 A | 10/1991 | Zaias |
| 5,097,846 A | 3/1992 | Larsen |
| 5,101,836 A | 4/1992 | Lee |
| 5,107,832 A | 4/1992 | Guibert et al. |
| 5,143,063 A | 9/1992 | Fellner |
| 5,186,181 A | 2/1993 | Franconi et al. |
| 5,190,518 A | 3/1993 | Takasu |
| 5,198,776 A | 3/1993 | Carr |
| 5,226,907 A | 7/1993 | Tankovich |
| 5,234,004 A | 8/1993 | Hascoet et al. |
| 5,246,438 A | 9/1993 | Langberg |
| 5,272,301 A | 12/1993 | Finger et al. |
| 5,295,955 A | 3/1994 | Rosen et al. |
| 5,301,692 A | 4/1994 | Knowlton |
| 5,305,748 A | 4/1994 | Wilk |
| 5,315,994 A | 5/1994 | Guibert et al. |
| 5,316,000 A | 5/1994 | Chapelon et al. |
| 5,364,336 A | 11/1994 | Carr |
| 5,364,394 A | 11/1994 | Mehl |
| 5,383,917 A | 1/1995 | Desai et al. |
| 5,385,544 A | 1/1995 | Edwards et al. |
| 5,405,346 A | 4/1995 | Grundy et al. |
| 5,407,440 A | 4/1995 | Zinreich et al. |
| 5,409,484 A | 4/1995 | Erlich et al. |
| 5,421,819 A | 6/1995 | Edwards et al. |
| 5,425,728 A | 6/1995 | Tankovich |
| 5,431,650 A | 7/1995 | Cosmescu |
| 5,433,740 A | 7/1995 | Yamaguchi |
| 5,441,532 A | 8/1995 | Fenn |
| 5,443,487 A | 8/1995 | Guibert et al. |
| 5,462,521 A | 10/1995 | Brucker et al. |
| 5,474,071 A | 12/1995 | Chapelon et al. |
| 5,503,150 A | 4/1996 | Evans |
| 5,507,741 A | 4/1996 | L'Esperance, Jr. |
| 5,507,790 A | 4/1996 | Weiss |
| 5,509,929 A | 4/1996 | Hascoet et al. |
| 5,522,814 A | 6/1996 | Bernaz |
| 5,531,662 A | 7/1996 | Carr |
| 5,540,681 A | 7/1996 | Strul et al. |
| 5,549,639 A | 8/1996 | Ross |
| 5,553,612 A | 9/1996 | Lundback |
| 5,569,237 A | 10/1996 | Beckenstein |
| 5,571,154 A | 11/1996 | Ren |
| 5,575,789 A | 11/1996 | Bell et al. |
| 5,584,830 A | 12/1996 | Ladd et al. |
| 5,586,981 A | 12/1996 | Hu |
| 5,595,568 A | 1/1997 | Anderson et al. |
| 5,660,836 A | 8/1997 | Knowlton |
| 5,662,110 A | 9/1997 | Carr |
| 5,669,916 A | 9/1997 | Anderson |
| 5,674,219 A | 10/1997 | Monson et al. |
| 5,683,381 A | 11/1997 | Carr et al. |
| 5,683,382 A | 11/1997 | Lenihan et al. |
| 5,690,614 A | 11/1997 | Carr et al. |
| 5,707,403 A | 1/1998 | Grove et al. |
| 5,724,966 A | 3/1998 | Lundback |
| 5,733,269 A | 3/1998 | Fuisz |
| 5,735,844 A | 4/1998 | Anderson et al. |
| 5,742,392 A | 4/1998 | Anderson et al. |
| 5,743,899 A | 4/1998 | Zinreich |
| 5,755,753 A | 5/1998 | Knowlton |
| 5,769,879 A | 6/1998 | Richards et al. |
| 5,776,127 A | 7/1998 | Anderson et al. |
| 5,782,897 A | 7/1998 | Carr |
| 5,810,801 A | 9/1998 | Anderson et al. |

(56) References Cited

U.S. PATENT DOCUMENTS

| | | |
|---|---|---|
| 5,810,804 A | 9/1998 | Gough et al. |
| 5,814,996 A | 9/1998 | Winter |
| 5,824,023 A | 10/1998 | Anderson |
| 5,830,208 A | 11/1998 | Muller |
| 5,836,999 A | 11/1998 | Eckhouse et al. |
| 5,868,732 A | 2/1999 | Waldman et al. |
| 5,879,346 A | 3/1999 | Waldman et al. |
| 5,891,094 A | 4/1999 | Masterson et al. |
| 5,897,549 A | 4/1999 | Tankovich |
| 5,902,263 A | 5/1999 | Patterson et al. |
| 5,904,709 A | 5/1999 | Arndt et al. |
| 5,919,218 A | 7/1999 | Carr |
| 5,928,797 A | 7/1999 | Vineberg |
| 5,931,860 A | 8/1999 | Reid et al. |
| 5,949,845 A | 9/1999 | Sterzer |
| 5,971,982 A | 10/1999 | Betsill et al. |
| 5,979,454 A | 11/1999 | Anvari et al. |
| 5,983,124 A | 11/1999 | Carr |
| 5,983,900 A | 11/1999 | Clement et al. |
| 5,989,245 A | 11/1999 | Pescott |
| 6,015,404 A | 1/2000 | Altshuler et al. |
| 6,024,095 A | 2/2000 | Stanley, III |
| 6,026,331 A | 2/2000 | Feldberg et al. |
| 6,026,816 A | 2/2000 | McMillan et al. |
| 6,030,378 A | 2/2000 | Stewart |
| 6,036,632 A | 3/2000 | Whitmore, III et al. |
| 6,047,215 A | 4/2000 | McClure et al. |
| 6,050,990 A | 4/2000 | Tankovich et al. |
| 6,077,294 A | 6/2000 | Cho et al. |
| 6,080,146 A | 6/2000 | Altshuler et al. |
| 6,093,186 A | 7/2000 | Goble |
| 6,097,985 A | 8/2000 | Kasevich et al. |
| 6,104,959 A | 8/2000 | Spertell |
| 6,106,514 A | 8/2000 | O'Donnell, Jr. |
| 6,113,559 A | 9/2000 | Klopotek |
| 6,113,593 A | 9/2000 | Tu et al. |
| 6,126,636 A | 10/2000 | Naka |
| 6,129,696 A | 10/2000 | Sibalis |
| 6,139,569 A | 10/2000 | Ingle et al. |
| 6,149,644 A | 11/2000 | Xie |
| 6,162,212 A | 12/2000 | Kreindel et al. |
| 6,162,218 A | 12/2000 | Elbrecht et al. |
| 6,171,301 B1 | 1/2001 | Nelson et al. |
| 6,175,768 B1 | 1/2001 | Arndt et al. |
| 6,181,970 B1 | 1/2001 | Kasevich |
| 6,183,773 B1 | 2/2001 | Anderson |
| 6,187,001 B1 | 2/2001 | Azar et al. |
| 6,197,020 B1 | 3/2001 | O'Donnell, Jr. |
| 6,208,903 B1 | 3/2001 | Richards et al. |
| 6,210,367 B1 | 4/2001 | Carr |
| 6,214,034 B1 | 4/2001 | Azar |
| 6,223,076 B1 | 4/2001 | Tapper |
| 6,231,569 B1 | 5/2001 | Bek et al. |
| 6,235,016 B1 | 5/2001 | Stewart |
| 6,241,753 B1 | 6/2001 | Knowlton |
| 6,245,062 B1 | 6/2001 | Berube et al. |
| 6,264,652 B1 | 7/2001 | Eggers et al. |
| 6,273,884 B1 | 8/2001 | Altshuler et al. |
| 6,277,104 B1 | 8/2001 | Lasko et al. |
| 6,277,111 B1 | 8/2001 | Clement et al. |
| 6,277,116 B1 | 8/2001 | Utely et al. |
| 6,280,441 B1 | 8/2001 | Ryan |
| 6,283,956 B1 | 9/2001 | McDaniel |
| 6,283,987 B1 | 9/2001 | Laird et al. |
| 6,287,302 B1 | 9/2001 | Berube |
| 6,290,699 B1 | 9/2001 | Hall et al. |
| 6,293,941 B1 | 9/2001 | Strul et al. |
| 6,306,128 B1 | 10/2001 | Waldman et al. |
| 6,306,130 B1 | 10/2001 | Anderson et al. |
| 6,319,211 B1 | 11/2001 | Ito et al. |
| 6,322,584 B2 | 11/2001 | Ingle et al. |
| 6,325,769 B1 | 12/2001 | Klopotek |
| 6,330,479 B1 | 12/2001 | Stauffer |
| 6,334,074 B1 | 12/2001 | Spertell |
| 6,347,251 B1 | 2/2002 | Deng |
| 6,350,263 B1 | 2/2002 | Wetzig et al. |
| 6,350,276 B1 | 2/2002 | Knowlton |
| 6,361,531 B1 | 3/2002 | Hissong |
| 6,364,876 B1 | 4/2002 | Erb et al. |
| 6,383,176 B1 | 5/2002 | Connors et al. |
| 6,387,103 B2 | 5/2002 | Shadduck |
| 6,402,739 B1 | 6/2002 | Neev |
| 6,409,720 B1 | 6/2002 | Hissong et al. |
| 6,409,722 B1 | 6/2002 | Hoey et al. |
| 6,413,253 B1 | 7/2002 | Koop et al. |
| 6,413,254 B1 | 7/2002 | Hissong et al. |
| 6,413,255 B1 | 7/2002 | Stern |
| 6,427,089 B1 | 7/2002 | Knowlton |
| 6,428,532 B1 | 8/2002 | Doukas et al. |
| 6,430,446 B1 | 8/2002 | Knowlton |
| 6,436,094 B1 | 8/2002 | Reuter |
| 6,436,127 B1 | 8/2002 | Anderson et al. |
| 6,443,914 B1 | 9/2002 | Costantino |
| 6,443,946 B2 | 9/2002 | Clement et al. |
| 6,451,013 B1 | 9/2002 | Bays et al. |
| 6,451,015 B1 | 9/2002 | Rittman, III et al. |
| 6,457,476 B1 | 10/2002 | Elmer et al. |
| 6,461,378 B1 | 10/2002 | Knowlton |
| 6,468,235 B2 | 10/2002 | Ito et al. |
| 6,470,216 B1 | 10/2002 | Knowlton |
| 6,471,662 B1 | 10/2002 | Jaggy et al. |
| 6,471,696 B1 | 10/2002 | Berube et al. |
| 6,475,179 B1 | 11/2002 | Wang et al. |
| 6,475,211 B2 | 11/2002 | Chess et al. |
| 6,480,746 B1 | 11/2002 | Ingle et al. |
| 6,485,484 B1 | 11/2002 | Connors et al. |
| 6,485,703 B1 | 11/2002 | Cóte et al. |
| 6,500,141 B1 | 12/2002 | Irion et al. |
| 6,508,813 B1 | 1/2003 | Altshuler |
| 6,514,250 B1 | 2/2003 | Jahns et al. |
| 6,517,532 B1 | 2/2003 | Altshuler et al. |
| 6,529,778 B2 | 3/2003 | Prutchi |
| 6,558,382 B2 | 5/2003 | Jahns et al. |
| 6,575,969 B1 | 6/2003 | Rittman, III et al. |
| 6,577,903 B1 | 6/2003 | Cronin et al. |
| 6,584,360 B2 | 6/2003 | Francischelli et al. |
| 6,585,733 B2 | 7/2003 | Wellman |
| 6,595,934 B1 | 7/2003 | Hissong et al. |
| 6,600,951 B1 | 7/2003 | Anderson |
| 6,605,080 B1 | 8/2003 | Altshuler et al. |
| 6,607,498 B2 | 8/2003 | Eshel |
| 6,626,854 B2 | 9/2003 | Friedman et al. |
| 6,628,990 B1 | 9/2003 | Habib et al. |
| 6,629,974 B2 | 10/2003 | Penny et al. |
| 6,645,162 B2 | 11/2003 | Friedman et al. |
| 6,648,904 B2 | 11/2003 | Altshuler et al. |
| 6,652,518 B2 | 11/2003 | Wellman et al. |
| 6,653,618 B2 | 11/2003 | Zenzie |
| 6,662,054 B2 | 12/2003 | Kreindel et al. |
| 6,663,659 B2 | 12/2003 | McDaniel |
| 6,676,654 B1 | 1/2004 | Balle Petersen et al. |
| 6,676,655 B2 | 1/2004 | McDaniel |
| 6,682,501 B1 | 1/2004 | Nelson et al. |
| 6,692,450 B1 | 2/2004 | Coleman |
| 6,723,090 B2 | 4/2004 | Altshuler et al. |
| 6,725,095 B2 | 4/2004 | Fenn et al. |
| 6,736,810 B2 | 5/2004 | Hoey et al. |
| 6,743,222 B2 | 6/2004 | Durkin et al. |
| 6,763,836 B2 | 7/2004 | Tasto et al. |
| 6,766,202 B2 | 7/2004 | Underwood et al. |
| 6,807,446 B2 | 10/2004 | Fenn et al. |
| 6,808,532 B2 | 10/2004 | Andersen et al. |
| 6,821,274 B2 | 11/2004 | McHale et al. |
| 6,823,216 B1 | 11/2004 | Salomir et al. |
| 6,824,542 B2 | 11/2004 | Jay |
| 6,856,839 B2 | 2/2005 | Litovitz |
| 6,861,954 B2 | 3/2005 | Levin |
| 6,878,144 B2 | 4/2005 | Altshuler et al. |
| 6,878,147 B2 | 4/2005 | Prakash et al. |
| 6,881,212 B1 | 4/2005 | Clement et al. |
| 6,887,239 B2 | 5/2005 | Elstrom et al. |
| 6,887,260 B1 | 5/2005 | McDaniel |
| 6,888,319 B2 | 5/2005 | Inochkin et al. |
| 6,897,238 B2 | 5/2005 | Anderson |

(56) References Cited

U.S. PATENT DOCUMENTS

| | | |
|---|---|---|
| 6,907,879 B2 | 6/2005 | Drinan et al. |
| 6,916,316 B2 | 7/2005 | Jay |
| 6,918,908 B2 | 7/2005 | Bonner et al. |
| 6,939,344 B2 | 9/2005 | Kreindel |
| 6,939,346 B2 | 9/2005 | Kannenberg et al. |
| 6,955,672 B2 | 10/2005 | Cense et al. |
| 6,974,415 B2 | 12/2005 | Cerwin et al. |
| 6,976,984 B2 | 12/2005 | Cense et al. |
| 6,997,923 B2 | 2/2006 | Anderson et al. |
| 7,006,874 B2 | 2/2006 | Knowlton et al. |
| 7,022,121 B2 | 4/2006 | Stern et al. |
| 7,029,469 B2 | 4/2006 | Vasily |
| 7,033,352 B1 | 4/2006 | Gauthier et al. |
| 7,044,959 B2 | 5/2006 | Anderson et al. |
| 7,056,318 B2 | 6/2006 | Black |
| 7,066,929 B1 | 6/2006 | Azar et al. |
| 7,074,218 B2 | 7/2006 | Washington et al. |
| 7,081,111 B2 | 7/2006 | Svaasand et al. |
| 7,089,054 B2 | 8/2006 | Palti |
| 7,107,997 B1 | 9/2006 | Moses et al. |
| 7,115,123 B2 | 10/2006 | Knowlton et al. |
| 7,118,590 B1 | 10/2006 | Cronin |
| 7,122,029 B2 | 10/2006 | Koop et al. |
| 7,128,739 B2 | 10/2006 | Prakash et al. |
| 7,135,033 B2 | 11/2006 | Altshuler et al. |
| 7,136,699 B2 | 11/2006 | Palti |
| 7,141,049 B2 | 11/2006 | Stern et al. |
| 7,151,964 B2 | 12/2006 | Desai et al. |
| 7,153,256 B2 | 12/2006 | Riehl et al. |
| 7,153,285 B2 | 12/2006 | Lauman et al. |
| 7,163,536 B2 | 1/2007 | Godara |
| 7,175,950 B2 | 2/2007 | Anderson et al. |
| 7,189,230 B2 | 3/2007 | Knowlton |
| 7,192,429 B2 | 3/2007 | Trembly |
| 7,204,832 B2 | 4/2007 | Altshuler et al. |
| 7,217,265 B2 | 5/2007 | Hennings et al. |
| 7,220,254 B2 | 5/2007 | Altshuler et al. |
| 7,220,778 B2 | 5/2007 | Anderson et al. |
| 7,229,436 B2 | 6/2007 | Stern et al. |
| 7,234,739 B2 | 6/2007 | Saitoh et al. |
| 7,238,182 B2 | 7/2007 | Swoyer et al. |
| 7,241,291 B2 | 7/2007 | Kreindel et al. |
| 7,247,155 B2 | 7/2007 | Hoey et al. |
| 7,250,047 B2 | 7/2007 | Anderson et al. |
| 7,252,628 B2 | 8/2007 | Van Hal et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,290,326 B2 | 11/2007 | Dutton |
| 7,309,335 B2 | 12/2007 | Altshuler et al. |
| 7,311,674 B2 | 12/2007 | Gingrich et al. |
| 7,329,273 B2 | 2/2008 | Altshuler et al. |
| 7,329,274 B2 | 2/2008 | Altshuler et al. |
| 7,331,951 B2 | 2/2008 | Eshel et al. |
| 7,344,587 B2 | 3/2008 | Khan et al. |
| 7,347,855 B2 | 3/2008 | Eshel et al. |
| 7,351,252 B2 | 4/2008 | Altshuler et al. |
| 7,354,448 B2 | 4/2008 | Altshuler et al. |
| 7,367,341 B2 | 5/2008 | Anderson et al. |
| 7,377,917 B2 | 5/2008 | Trembly |
| 7,399,297 B2 | 7/2008 | Ikadai et al. |
| 7,422,586 B2 | 9/2008 | Morris et al. |
| 7,422,598 B2 | 9/2008 | Altshuler et al. |
| 7,431,718 B2 | 10/2008 | Ikadai |
| 7,470,270 B2 | 12/2008 | Azar et al. |
| 7,479,101 B2 | 1/2009 | Hunter et al. |
| 7,481,807 B2 | 1/2009 | Knudsen et al. |
| 7,491,171 B2 | 2/2009 | Barthe et al. |
| 7,524,328 B2 | 4/2009 | Connors et al. |
| 7,530,356 B2 | 5/2009 | Slayton et al. |
| 7,530,958 B2 | 5/2009 | Slayton et al. |
| 7,540,869 B2 | 6/2009 | Altshuler et al. |
| 7,544,204 B2 | 6/2009 | Krespi et al. |
| 7,565,207 B2 | 7/2009 | Turner et al. |
| 7,568,619 B2 | 8/2009 | Todd et al. |
| 7,588,547 B2 | 9/2009 | Deem et al. |
| 7,599,745 B2 | 10/2009 | Palti |
| 7,601,128 B2 | 10/2009 | Deem et al. |
| 7,613,523 B2 | 11/2009 | Eggers et al. |
| 7,630,774 B2 | 12/2009 | Karni et al. |
| 7,643,883 B2 | 1/2010 | Kreindel |
| 7,682,321 B2 | 3/2010 | Naldoni |
| 7,722,535 B2 | 5/2010 | Randlov et al. |
| 7,722,600 B2 | 5/2010 | Connors et al. |
| 7,722,656 B1 | 5/2010 | Segal |
| 7,736,360 B2 | 6/2010 | Mody et al. |
| 7,740,600 B2 | 6/2010 | Slatkine et al. |
| 7,740,651 B2 | 6/2010 | Barak et al. |
| 7,749,260 B2 | 7/2010 | Da Silva et al. |
| 7,758,524 B2 | 7/2010 | Barthe et al. |
| 7,758,537 B1 | 7/2010 | Brunell et al. |
| 7,762,964 B2 | 7/2010 | Slatkine |
| 7,763,060 B2 | 7/2010 | Baumann |
| 7,771,421 B2 | 8/2010 | Stewart et al. |
| 7,799,019 B2 | 9/2010 | Turovskiy et al. |
| 7,805,201 B2 | 9/2010 | Palti |
| 7,815,570 B2 | 10/2010 | Eshel et al. |
| 7,815,633 B2 | 10/2010 | Zanelli et al. |
| 7,824,394 B2 | 11/2010 | Manstein |
| 7,828,734 B2 | 11/2010 | Azhari et al. |
| 7,837,694 B2 | 11/2010 | Tethrake et al. |
| 7,842,029 B2 | 11/2010 | Anderson et al. |
| 7,854,754 B2 | 12/2010 | Ting et al. |
| 7,857,773 B2 | 12/2010 | Desilets et al. |
| 7,857,775 B2 | 12/2010 | Rosenberg et al. |
| 7,862,564 B2 | 1/2011 | Goble |
| 7,864,129 B2 | 1/2011 | Konishi |
| 7,891,362 B2 | 2/2011 | Domankevitz et al. |
| 7,905,844 B2 | 3/2011 | Desilets et al. |
| 8,073,550 B1 | 12/2011 | Spertell |
| 2001/0005775 A1 | 6/2001 | Samson |
| 2001/0016761 A1 | 8/2001 | Rudie et al. |
| 2001/0050083 A1 | 12/2001 | Marchitto et al. |
| 2002/0062124 A1 | 5/2002 | Keane |
| 2002/0087151 A1 | 7/2002 | Mody et al. |
| 2002/0156471 A1 | 10/2002 | Stern et al. |
| 2002/0165529 A1 | 11/2002 | Danek |
| 2002/0193851 A1 | 12/2002 | Silverman et al. |
| 2003/0004082 A1 | 1/2003 | Masschelein et al. |
| 2003/0006811 A1 | 1/2003 | Oosawa et al. |
| 2003/0130575 A1* | 7/2003 | Desai ............................ 600/417 |
| 2003/0130711 A1 | 7/2003 | Pearson et al. |
| 2003/0158566 A1 | 8/2003 | Brett |
| 2003/0212393 A1 | 11/2003 | Knowlton et al. |
| 2003/0216728 A1 | 11/2003 | Stern et al. |
| 2004/0000316 A1 | 1/2004 | Knowlton et al. |
| 2004/0002705 A1 | 1/2004 | Knowlton et al. |
| 2004/0049251 A1 | 3/2004 | Knowlton |
| 2004/0073115 A1 | 4/2004 | Horzewski et al. |
| 2004/0092875 A1 | 5/2004 | Kochamba |
| 2004/0140028 A1 | 7/2004 | Clark et al. |
| 2004/0186535 A1 | 9/2004 | Knowlton |
| 2004/0206365 A1 | 10/2004 | Knowlton |
| 2004/0210214 A1 | 10/2004 | Knowlton |
| 2004/0230260 A1 | 11/2004 | Macfarland et al. |
| 2004/0243182 A1 | 12/2004 | Cohen et al. |
| 2004/0243200 A1 | 12/2004 | Turner et al. |
| 2004/0249426 A1 | 12/2004 | Hoenig et al. |
| 2005/0010271 A1 | 1/2005 | Merchant |
| 2005/0137654 A1 | 6/2005 | Hoenig et al. |
| 2005/0215987 A1 | 9/2005 | Slatkine |
| 2005/0251117 A1 | 11/2005 | Anderson et al. |
| 2005/0251120 A1 | 11/2005 | Anderson et al. |
| 2005/0288666 A1 | 12/2005 | Bertolero et al. |
| 2006/0020309 A1 | 1/2006 | Altshuler et al. |
| 2006/0036300 A1 | 2/2006 | Kreindel |
| 2006/0111744 A1* | 5/2006 | Makin et al. ...................... 607/1 |
| 2006/0112698 A1 | 6/2006 | Cazzini et al. |
| 2006/0129209 A1 | 6/2006 | McDaniel |
| 2006/0151485 A1 | 7/2006 | Cronin |
| 2006/0161228 A1 | 7/2006 | Lach |
| 2006/0167498 A1 | 7/2006 | Dilorenzo |
| 2006/0184205 A1 | 8/2006 | Schuler et al. |
| 2006/0189964 A1 | 8/2006 | Anderson et al. |

(56) References Cited

U.S. PATENT DOCUMENTS

| | | |
|---|---|---|
| 2006/0206110 A1 | 9/2006 | Knowlton et al. |
| 2006/0259102 A1 | 11/2006 | Slatkine |
| 2006/0264926 A1* | 11/2006 | Kochamba ............... 606/41 |
| 2006/0265034 A1 | 11/2006 | Aknine et al. |
| 2006/0271028 A1 | 11/2006 | Altshuler et al. |
| 2006/0276860 A1 | 12/2006 | Ferren et al. |
| 2007/0010810 A1 | 1/2007 | Kochamba |
| 2007/0016032 A1 | 1/2007 | Aknine |
| 2007/0020355 A1 | 1/2007 | Schlebusch et al. |
| 2007/0049918 A1 | 3/2007 | Van Der Weide et al. |
| 2007/0060989 A1* | 3/2007 | Deem et al. ............... 607/99 |
| 2007/0078290 A1 | 4/2007 | Esenaliev |
| 2007/0078502 A1 | 4/2007 | Weber et al. |
| 2007/0088413 A1 | 4/2007 | Weber et al. |
| 2007/0179482 A1 | 8/2007 | Anderson |
| 2007/0179535 A1 | 8/2007 | Morrissey et al. |
| 2007/0233226 A1 | 10/2007 | Kochamba et al. |
| 2007/0237620 A1 | 10/2007 | Mühlhoff et al. |
| 2007/0255355 A1 | 11/2007 | Altshuler et al. |
| 2007/0255362 A1 | 11/2007 | Levinson et al. |
| 2007/0265585 A1 | 11/2007 | Joshi et al. |
| 2007/0270925 A1 | 11/2007 | Levinson |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0215039 A1* | 9/2008 | Slatkine et al. ............... 606/9 |
| 2008/0269851 A1 | 10/2008 | Deem et al. |
| 2008/0294152 A1 | 11/2008 | Altshuler et al. |
| 2008/0319437 A1 | 12/2008 | Turner et al. |
| 2009/0221999 A1 | 9/2009 | Shahidi |
| 2009/0299361 A1 | 12/2009 | Flyash et al. |
| 2010/0114086 A1 | 5/2010 | Deem et al. |
| 2010/0211059 A1 | 8/2010 | Deem et al. |
| 2010/0268220 A1 | 10/2010 | Johnson et al. |
| 2011/0028898 A1 | 2/2011 | Clark, III et al. |
| 2011/0040299 A1 | 2/2011 | Kim et al. |
| 2011/0196365 A1 | 8/2011 | Kim et al. |
| 2011/0313412 A1 | 12/2011 | Kim et al. |
| 2012/0010609 A1 | 1/2012 | Deem et al. |
| 2012/0022622 A1 | 1/2012 | Johnson et al. |
| 2012/0041432 A1 | 2/2012 | Spertell |
| 2013/0066406 A1 | 3/2013 | Spertell |
| 2013/0072925 A1 | 3/2013 | Ben-Haim et al. |
| 2013/0072930 A1 | 3/2013 | Ben-Haim et al. |
| 2014/0005645 A1 | 1/2014 | Ben-Haim et al. |
| 2014/0180271 A1 | 6/2014 | Johnson et al. |
| 2014/0378959 A1 | 12/2014 | Spertell |

FOREIGN PATENT DOCUMENTS

| | | |
|---|---|---|
| EP | 1346753 A2 | 9/2003 |
| JP | 61-364 A | 1/1986 |
| JP | 62-149347 | 9/1987 |
| JP | S-63177856 A | 7/1988 |
| JP | H09-239040 A | 9/1997 |
| JP | 2001-514921 A | 9/2001 |
| JP | 2006503618 | 2/2006 |
| JP | 2006-289098 | 10/2006 |
| WO | WO 89/02292 A1 | 3/1989 |
| WO | WO 92/07622 A1 | 5/1992 |
| WO | WO 96/23447 A1 | 8/1996 |
| WO | WO 96/41579 A1 | 12/1996 |
| WO | WO 99/46005 A1 | 9/1999 |
| WO | WO 00/24463 A2 | 5/2000 |
| WO | WO 01/58361 A1 | 8/2001 |
| WO | WO 01/58361 A1 | 8/2001 |
| WO | WO 03/039385 A2 | 5/2003 |
| WO | WO 2004/034925 A2 | 4/2004 |
| WO | WO 2005/060354 A2 | 7/2005 |
| WO | WO 2005/099369 A2 | 10/2005 |
| WO | WO 2005/112807 A2 | 12/2005 |
| WO | WO 2006/089227 A2 | 8/2006 |
| WO | WO 2006/090217 A1 | 8/2006 |
| WO | WO 2006/117682 A2 | 11/2006 |
| WO | WO 2006/122136 A2 | 11/2006 |
| WO | WO 2007/015247 * | 2/2007 ............... A61M 5/42 |
| WO | WO 2007/015247 A2 | 2/2007 |
| WO | WO 2007/030367 A2 | 3/2007 |
| WO | WO 2007/038567 A1 | 4/2007 |
| WO | WO 2007/050572 A2 | 5/2007 |
| WO | WO 2007/106339 A2 | 9/2007 |
| WO | WO2007/108516 A1 | 9/2007 |
| WO | WO 2007/131112 A2 | 11/2007 |
| WO | WO 2007/140469 A2 | 12/2007 |
| WO | WO 2009/072108 A2 | 6/2009 |

OTHER PUBLICATIONS

Acculis; Microwave Ablation for Healthcare Professionals; 2 pgs.; accessed Jun. 24, 2008; (http://www.acculis.com/mta).

Aesthera US—How it Works; 2 pgs.; accessed Jul. 8, 2008 (http://www.aesthera.com/go/aestheralUS/patients/how_it_works/index.cfm).

Allergan Pharmaceuticals; Botox® (product insert); 16 pgs.; Oct. 2006.

Alster et al.; Improvement of neck and cheek laxity with a non-ablative radiofrequency device: a lifting experience; Dermatol Surg; 30(4); pp. 503-507; Apr. 2004.

Arneja et al.; Axillary hyperhidrosis: a 5-year review of treatment efficacy and recurrence rates using a new arthroscopic shaver technique; Plast. Reconstr. Surg.; vol. 119; pp. 562-567; Feb. 2007.

Ashby et al.; Cryosurgery for Axillary Hyperhidrosis; British Medical Journal Short Reports; London; pp. 1173-1174; Nov. 13, 1976.

Atkins et al.; Hyperhidrosis: A Review of Current Management; Plast Reconstr Surg; 110(1); pp. 222-228; Jul. 2002.

Ball, P.; Radio sweat gland—90 GHz; Nature; 452(7188); p. 676; Apr. 10, 2008; printed Jun. 18, 2012 from website (http://www.nature.com/news/2008/080409/full/452676a.html).

Beer et al., Immunohistochemical Differentiation and Localization Analysis of Sweat Glands in the Adult Human Axilla, Plastic and Reconstructive Surgery, vol. 117, No. 6, pp. 2043-2049, May 2006.

Bentel et al.; Variability of the depth of supraclavicular and axillary lymph nodes in patients with breast cancer: is a posterior axillary boost field necessary?; Int J Radiation Oncology Biol Phys; vol. 47(3); pp. 755-758; Jun. 2000.

Bindu et al.; Microwave characterization of breast-phantom materials; Microwave and Optical Tech. Letters; 43(6); pp. 506-508; Dec. 20, 2004.

Bioportfolio; Tenex Health Receives FDA clearance for innovative TX1) tissue removal system; 2 pgs.; release dated Mar. 9, 2011; printed on Jun. 18, 2012 from website (http://www.bioportfolio.com/news/article/519143/Tenex-Health-Receives-Fda-Clearance-For-Innovative-Tx1-Tissue-Removal-System.html).

Blanchard et al.; Relapse and morbidity in patients undergoing sentinel lymph node biopsy alone or with axillary dissection for breast cancer; Arch Surg; vol. 138; pp. 482-488; May 2003.

Brace et al., Microwave Ablation with a Trixial Antenna: Results in ex vivo Bovine Liver, IEEE transactions on Microwave Theory and Techniques, vol. 53, No. 1, pp. 215-220 (Jan. 2005).

Burns, Jay A.; Thermage: monopolar radiofrequency; Aesthetic Surg J; 25 (6); pp. 638-642; Nov./Dec. 2005.

Campbell et al.; Dielectric properties of female human breast tissue measured in vitro at 3.2 GHz; Phys. Med. Biol.; 37(1); pp. 193-210; Jan. 1992.

Candela Corp.; The Candela SeleroPLUS Laser with Dynamic Cooling Device: The Benefits of Anesthesia without the Risks; Nov. 1998.

Chang et al.; A conductive plastic for simulating biological tissue at microwave frequencies; IEEE Trans on Electromagnetic Compatibility; 42(1); pp. 76-81; Feb. 2000.

Christ et al.; Characterization of the Electromagnetic Near-Field Absorption in Layered Biological Tissue in the Frequency Range from 30 MHz to 6000 MHz, Phys. Med. Biol. 51, pp. 4951-4965; Oct. 2006.

Christ et al., The Dependence of Electromagnetic Far-Field Absorption on Body Tissue Composition in the Frequency Range from 300 MHz to 6 GHz, IEEE Transactions on Microwave Theory and Techniques, vol. 54, No. 5, pp. 2188-2195 (May 2006).

(56) References Cited

OTHER PUBLICATIONS

CK Electronic GmbH; Scientific Measurements of Skin and Hair (product information); 15 pgs.; published after Sep. 2006.

Cobham; Antenna & Radome Design Aids (product list); 1 pg.; Aug. 2001.

Copty et al., Low-power near-field microwave applicator for localized heating of soft matter, Applied Physics Letters, vol. 84, No. 25, pp. 5109-5111 (Jun. 21, 2004).

De Bruijne et al., Effects of waterbolus size, shape and configuration on the SAR distribution pattern of the Lucite cone applicator, International Journal of Hyperthermia, 22(1): 15-28 (Feb. 2006).

Diederich et al.; Pre-clinical Evaluation of a Microwave Planar Array Applicator for Superficial Hyperthermia; International Journal of Hyperthermia; vol. 9, No. 2; pp. 227-246; Jan. 1993.

Drozd et al.; Comparison of Coaxial Dipole Antennas for Applications in the Near-Field and Far-Field Regions; MW Journal, vol. 47, No. 5 (May 2004), http://www.mwjournal.com/Journal, accessed Dec. 10, 2007.

Duparc et al.; Anatomical basis of the variable aspects of injuries of the axillary nerve (excluding the terminal branches in the deltoid muscle); Surg Radiol Anat; vol. 19(3); pp. 127-132; May 1997.

Eleiwa et al.; Accurate FDTD simulation of biological tissues for bio-electromagnetic applications; IEEE Proc. SoutheastCon 2001; Clemson, SC; Mar. 30-Apr. 1, 2001; pp. 174-178.

Farace et al.; An automated method for mapping human tissue permittivities by MRI in hyperthermia treatment planning; Phys. Med. Biol.; 42(11); pp. 2159-2174; Nov. 1997.

Fitzpatrick et al.; Multicenter study of noninvasive radiofrequency for periorbital tissue tightening; Lasers Surg Med; 33(4); pp. 232-242; Mar. 2003.

Gabriel et al.; Dielectric parameters relevant to microwave dielectric heating; Chem Soc Rev; 27(3); pp. 213R224; May-Jun. 1998.

Gabriel et al.; The dielectric properties of biological tissues: I. Literature survey; Phys Med Biol; 41(11); pp. 2231R2249; Nov. 1996.

Gabriel et al.; The dielectric properties of biological tissues: II. Measurements in the frequency range 10 Hz to 20 GHz; Phys Med Biol; 41(11); pp. 2251R2269; Nov. 1996.

Gabriel et al.; The dielectric properties of biological tissues: III. Parametric models for the dielectric spectrum of tissues; Phys Med Biol; 41(11); pp. 2271R2293; Nov. 1996.

Gabriel, et al.; Comparison of the Dielectric Properties of Normal and Wounded Human Skin Material; Bioelectromagnetics; 8; pp. 23-27; Jan. 1987.

Galloway et al.; Ultrasound imaging of the axillary vein—anatomical basis for central venous access; British ournal of Anaesthesia; 90(5); pp. 589-595; May 2003.

Gandhi et al.; Electromagnetic Absorption in the Human Head and Neck for Mobile Telephones at 835 and 1900 MHz; IEEE Transactions on Microwave Theory and Techniques; 44(10); pp. 1884R1897; Oct. 1996.

Garber, B. B.; Office microwave treatment of enlarged prostate symptoms; 2 pgs.; printed from website (http://www.garber-online.com/microwave-treatment.htm) on Jun. 18, 2012.

Gold et al.; Treatment of Wrinkles and Skin Tightening Using Aluma(TM) Skin Renewal System with FACES (TM)(Functional Aspiration Controlled Electrothermal Stimulation) Technology; Lumens, Inc. (Oct. 2005).

Guidant Corp.; Guidant microwave surgical ablation system; 1 pg.; ©2004; printed Jun. 18, 2012 from website (http://web.archive.org/web/20070306031424/http://www.ctsnet.org/file/vendors/872/pdf/MicrowaveAblationIFU.pdf).

Guy, Arthur; History of Biological Effects and Medical Applications of Microwave Energy; IEEE Transactions on Microwave Theory and Techniques; 32(9); pp. 1182-1200; Sep. 1984.

Guy, Arthur; Therapeutic Heat and Cold, Fourth Ed.; Chapter 5: Biophysics of High-Frequency Currents and Electromagnetic Radiation; pp. 179R236. Williams and Wilkins (publishers); Apr. 1990.

Guy; Analyses of electromagnetic fields induced in biological tissues by thermographic studies on equivalent phantom models; IEEE Trans on Microwave Theory and Techniques; MTT-19(2); pp. 205-214; Feb. 1971.

Haedersdal et al.; Evidence-based review of hair removal using lasers and light sources; JEADV; vol. 20; pp. 9-20; Jan. 2006.

Hey-Shipton, et al.; The Complex Permittivity of Human Tissue at Microwave Frequencies; Phys. Med. Biol.; 27(8); pp. 1067-1071; Aug. 1982.

Hisada et al.; Hereditary Hemorrhagic Telangiectasia Showing Severe Anemia which was successfully treated with estrogen; International Medicine; vol. 34; No. 6; pp. 589-592; Jun. 1995.

Hornberger et al.; Recognition, diagnosis, and treatment of primary focal hyperhidrosis; J Am Acad Dermatol; vol. 51; pp. 274-286; Aug. 2004.

Hu, Da Zhang, Electromagnetic Field in Organism of Skin-Fat-Muscle, China Research Institute of Radiowave Propagation IEEE, pp. 807-812 (Aug. 1998).

Jacobsen et al.; Characteristics of microstrip muscle-loaded single-arm archimedean spiral antennas as investigated by FDTD numerical computations; IEEE Trans. On Biomedical Engineering; 52(2); pp. 321-330; Feb. 2005.

Jacobsen et al.; Characterization of a tranceiving antenna concept for microwave heating and thermometry of superficial tumors; PIER; vol. 18; pp. 105-125; (month unavailable) 1998.

Jacobsen et al.; Dual-mode antenna design for microwave heating and noninvasive thermometry of superficial tissue disease; IEEE Trans. On Biomedical Engineering; 47(11); pp. 1500-1509; Nov. 2000.

Jacobsen et al.; Multifrequency radiometric determination of temperature profiles in a lossy homogeneous phantom using a dual-mode antenna with integral water bolus; IEEE Trans. on Microwave Theory and Techniques; 50(7); pp. 1737-1746; Jul. 2002.

Jacobsen et al.; Nonparametric 1-D temperature restoration in lossy media using tikhonov regularization on sparse radiometry data; IEEE Trans. on Biomedical Engineering; 50(2); pp. 178-188; Feb. 2003.

Jacobsen et al.; Transceiving antenna for homogenious heating and radiometric thermometry during hyperthermia; Electronic Letters; 36(6); pp. 496-497; Mar. 16, 2000.

Johnson et al.; Automatic temperature controller for multielement array hyperthermia systems; IEEE Trans. on Biomedical Engineering; 53(6); pp. 1006-1015; Jun. 2006.

Johnson et al.; Evaluation of a dual-arm Archimedean spiral array for microwave hyperthermia; Int J Hyperthermia; 22(6); pp. 475R490; Sep. 2006.

Juang et al.; Construction of a conformal water bolus vest applicator for hyperthermia treatment of superficial skin cancer; Proc. of the 26th Ann. Int. Conf. of the IEEE EMBS; San Francisco, CA, USA; Sep. 1-5, 2004; pp. 3467-3470.

Kawoos et al., Issues in Wireless Intracranial Pressure Monitoring at Microwave Frequencies, PIERS Online, vol. 3, No. 6, pp. 927-931; 2007 (month unavailable).

Kirn, T. F.; Researchers seek to quantify thermage efficacy; Dermatologic Surgery; p. 36; Jan. 2007.

Kirsch et al.; Ultrastructure of collagen thermally denatured by microsecond domain pulsed carbon dioxide laser; Arch Dermatol; 134; pp. 1255-1259; Oct. 1998.

Kobayashi, T.; Electrosurgery Using Insulated Needles: Treatment of Axillary Bromhidrosis and Hyperhidrosis; Journal of Dermatologic Surgery & Oncology; 14(7) pp. 749-752; Jul. 1988.

Krusen, Frank (M.D.); Samuel Hyde Memorial Lecture: Medical Applications of Microwave Diathermy: Laboratory and Clinical Studies. Proceedings of the Royal Society of Medicine; 43(8); pp. 641-658, May 10, 1950.

Kumaradas et al.; Optimization of a beam shaping bolus for superficial microwave hyperthermia waveguide applicators using a finite element method; Phys. Med. Biol.; 48(1); pp. 1-18; Jan. 7, 2003.

Lagendijk et al; Hyperthermia dough: a fat and bone equivalent phantom to test microwave/radiofrequency hyperthermia heating systems; Phys. Med. Biol.; 30(7); pp. 709-712; Jul. 1985.

Land et al.; A quick accurate method for measuring the microwave dielectric properties of small tissue samples; Phys. Med. Biol.; 37(1); pp. 183-192; Jan. 1992.

(56) References Cited

OTHER PUBLICATIONS

Lane et al.; Pressure-Induced Bullae and Sweat Gland Necrosis Following Chemotherapy Induction; The American Journal of Medicine; vol. 117; pp. 441-443; Sep. 15, 2004.
Larson et al.; Microwave treatments for enlared prostate cause blood pressure surges, study shows; 2 pgs.; Apr. 11, 2008; printed on Jun. 18, 2012 from website (http://web.archive.org/web/20080415000815/http://www.sciencedaily.com/releases/2008/04/080408105820.htm).
Lawrence et al.; Selective Sweat Gland Removal with Minimal Skin Excision in the Treatment of Axillary Hyperhidrosis: a Retrospective Clinical and Histological Review of 15 Patients; British Journal of Dermatology; British Association of Dermatologists; 155(1), pp. 115-118; Jul. 2006.
Lehmann et al.; Therapeutic Heat; Therapeutic Heat and Cold, Fourth Ed.; Chapter 9; pp. 417-581; Williams & Wilkins (publishers), Baltimore, MD; Apr. 1990.
Lowe et al.; Botulinum toxin type A in the treatment of primary axillary hyperhidrosis: A 52-week multicenter double-blind, randomized, placebo-controlled study of efficacy and safety; J Am Acad Dermatol; vol. 56; pp. 604-611; Apr. 2007.
Lowe et al.; Microwave delivery system for lower leg telangiectasia; Journal of Cutaneous Laser Therapy; 2(1); pp. 3-7; Mar. 2000.
Lumenis Inc.; Aluma RF Skin Renewal System (product information); copyright 2007 (PB-1013670); 8 pgs.; Oct. 2007 (printed version).
MacCarini et al.; Advances in microwave hyperthermia of large superficial tumors; Microwave Symposium Digest, IEEE MTT-S International; pp. 1797-1800; Jun. 2005.
MacCarini et al.; Electromagnetic optimization of dual mode antennas for radiometry controlled heating of superficial tissue; Proceedings of SPIE; vol. 5698; Bellingham, WA; pp. 71-81; Jan. 2005.
MacCarini et al.; Optimization of a dual concentric conductor antenna for superficial hyperthermia applications; Proc. of the 26th Ann. Int. Conf. of the IEEE EMBS; San Francisco, CA, USA; Sep. 1-5, 2004; pp. 2518-2521.
Mazzurana et al.; A semi-automatic method for developing an anthropomorphic numerical model of dielectric anatomy by MRI; Phys. Med. Biol.; 48(19); pp. 3157-3170; Oct. 7, 2003.
Michel et al.; Design and Modeling of Microstrip—Microslot Applicators with Several Patches and Apertures for Microwave Hyperthermia; Microwave and Optical Technology Letters; vol. 14, No. 2; pp. 121-125; Feb. 5, 1997.
Mrozowski et al.; Parameterization of media dispersive properties for FDTD; IEEE Trans on Antennas and Propagation; 45(9); pp. 1438-1439; Sep. 1997.
Nagaoka et al.; Development of realistic high-resolution whole-body voxel models of Japanese adult males and females of average height and weight, and application of models to radio-frequency electromagnetic-field dosimetry; Phys. Med. Biol.; 49(1); pp. 1-15; Jan. 7, 2004.
Neuman; SAR pattern perturbations from resonance effects in water bolus layers used with superficial microwave hyperthermia applicators; Int. J. Hyperthermia; 18(3); pp. 180-193; May-Jun. 2002.
Park et al.; A Comparative Study of the Surgical Treatment of Axillary Osmidrosis by Instrument, Manual, and Combined Subcutaneous Shaving Procedures; 41(5); pp. 488-497; Nov. 1998.
Paulides et al.; A Patch Antenna Design for Application in a Phased-Array Head and Neck Hyperthermia Applicator; IEEE Transactions on Biomedical Engineering; 54(11); pp. 2057-2063; Nov. 2007.
Popovic et al.; Dielectric spectroscopy of breast tissue—improved model of the precision open-ended coaxial probe; Proc of the 25th Ann Int Conf of the IEEE EMBS; Cancun, Mexico; pp. 3791-3793; Sep. 17-21, 2003.
Popovic et al.; Response characterization of the precision open-ended coaxial probe for dielectric spectroscopy of breast tissue; 2003 IEEE—Anntennas and Propagation Soc. Int. Symp.; vol. 4; pp. 54-57; Jun. 22-27, 2003.
Pozar, David M.; Electromagnetic Theory (Introduction); Microwave Engineering, Second Edition; John Wiley & Sons, Inc.; p. 1; Aug. 1997.
Rappaport, C.; Treating Cardiac Disease with Catheter-Based Tissue Heating; IEEE Microwave Magazine; 3(1); pp. 57-64; Mar. 2002.
Riddle et al.; Complex permittivity measurements of common plastics over variable temperatures; IEEE Trans on Microwave Theory and Techniques; vol. 51(3); pp. 727-733; Mar. 2003.
Rolfsnes et al.; Design of spiral antennas for radiometric temperature measurement; Proc. of the 26th Ann. Int. Conf. of the IEEE EMBS; San Francisco, CA, USA; Sep. 1-5, 2004; pp. 2522-2525.
Rosen et al.; Microwaves treat heart disease; IEEE Microw Mag; 8(1); pp. 70R75; Feb. 2007.
Ross et al.; A pilot study of in vivo immediate tissue contraction with $CO_2$ skin laser resurfacing in a live farm pig; Dermatol Surg; 25(11); pp. 851R856; Nov. 1999.
Ross et al.; Comparison of carbon dioxide laser, erbium: Yag laser, dermabrasion, and dermatome A study of thermal damage, wound contraction, and woundhealing in a live pig model: Implications for skin. resurfacing; J Am Acad Dermatol; 42(1); pp. 92R105; Jan. 2000.
Ross et al.; Use of a novel erbium laser in a yucatan minipig: A study of residual thermal damage, ablation, and wound healing as a function of pulse duration; Lasers Surg Med; 30(2); pp. 93R100; Feb. 2002.
Rossetto et al.; Effect of complex bolus-tissue load configurations on SAR distributions from dual concentric conductor applicators; IEEE Trans. on Biomedical Engineering; 46(11); pp. 1310-1319; Nov. 1999.
Saito et al.; Clinical Trials of Interstitual Microwave Hyperthermia by Use of Coaxial-Slot Antenna With Two Slots; IEEE Trans. on Microwave Theory and Techniques; vol. 52; No. 8; pp. 1987-1991; Aug. 2004.
Sherar et al.; Helical antenna arrays for interstitial microwave thermal therapy for prostate cancer: tissue phantom testing and simulations for treatment; Physics in Medicine and Biology; 46(7); pp. 1905-1918; Jul. 2001.
Shimm, D et al.; Hyperthermia in the Treatment of Malignancies; Therapeutic Heat and Cold Fourth Edition edited by Justin Lehmann M.D., Chapter 14, pp. 674-699, Williams & Wilkins Publishers, Baltimore, MD; Apr. 1990.
Sipahioglu et al.; Dielectric properties of vegetables and fruits as a function of temperature, ash, and moisture content; Journal of Food Science; 68(1); pp. 234-239; Jan. 2003.
Solish et al.; A comprehensive approach to the recognition, diagnosis, and severity-based treatment of focal hyperhidrosis: recommendations of the Canadian hyperhidrosis advisory committee; Dermatol Surg; vol. 33; pp. 908-923; Aug. 2007.
Solish et al.; Prospective open-label study of botulinum toxin type A in patients with axillary hyperhodrosis: effects on functional impairment and quality of life; Dermatol Surg; vol. 31(4); pp. 405-413; Apr. 2005.
Solta Medical, Inc.; Study Published in Facial Plastic Surgery Journal Finds Selective Heating of Fibrous Septae Key to Success and Safety of Thermage(R) ThermaCool(TM) System; Thermage® Press Release; 2 pgs.; Jun. 20, 2005.
Spertell et al.; Review of clinical data on hair removal using the MW 2000 microwave delivery system (promotional material); 2000; MW Medical, Inc.; printed from http://www.hairfacts.com/medpubs/mwave/spertell.html on Jun. 23, 2009; 5 pgs.
Spertell; Presentation at the American Academy of Dermatology; MW Medical, Inc.; Mar. 10, 2000; 21 pgs.
Spertell; The application of microwaves to the treatment of cosmetic skin conditions: a technical summary; MW Medical, Inc.; pp. 1-15; May 25, 1999.
SRLI Technologies; BTC-2000} (product information); printed from website: http://www.srli.com/technologies/BTC2000.html on Nov. 16, 2009; 1 pg.
Stauffer et al.; Combination applicator for simultaneous heat and radiation; Proc. of the 26th Ann. Int. Conf. of the IEEE EMBS; San Francisco, CA, USA; Sep. 1-5, 2004; pp. 2514-2517.
Stauffer et al.; Dual mode antenna array for microwave heating and non-invasive thermometry of superficial tissue disease; SPIE Conf.

(56) References Cited

OTHER PUBLICATIONS on Thermal Treatment of Tissue with Image Guidance; San Jose, CA; SPIE; vol. 3594; pp. 139-147; Jan. 1999.
Stauffer et al.; Microwave array applicator for rediometry controlled superficial hyperthermia; Proc. of the SPIE; vol. 4247; pp. 19-29; Jun. 2001.
Stauffer et al.; Phantom and animal tissues for modelling the electrical properties of human liver; Int. J. Hyperthermia; 19(1); pp. 89-101; Jan.-Feb. 2003.
Stauffer et al.; Practical induction heating coil designs for clinical hyperthermia with ferromagnetic implants; IEEE Trans. on Biomedical Engineering; 41(1); pp. 17-28; Jan. 1994.
Stauffer et al.; Progress on system for applying simultaneous heat and brachytherapy to large-area surface disease; Proceedings of SPIE; vol. 5698; Bellingham, WA; pp. 82-96; Jan. 2005.
Stauffer et al.; Progress toward radiometry controlled conformal microwave array hyperthermia applicator; Proc. of the 22nd Ann. EMBS Int. Conf.; Chicago, IL; Jul. 23-28, 2000; pp. 1613-1616.
Stauffer, Paul R.; Evolving technology for thermal therapy of cancer; International Journal of Hyperthermia; 21(8); pp. 731-744; Dec. 2005.
Stauffer, Paul R.; Thermal Therapy Techniques for Skin and Superficial Tissue Disease; Critical Reviews; SPIE Optical Engineering Press (Bellingham, WA); vol. CR75; pp. 327-367; Jan. 2000.
Sterzer, Fred, Microwave Medical Devices; IEEE Microwave Magazine, 3 (1); pp. 65-70; Mar. 2002.
Stoy et al.; Dielectric properties of mammalian tissues from 0.1 to 100 MHz: a summary of recent data; Phys. Med. Bil.; 27(4); pp. 501-513; Apr. 1982.
Strutton et al.; US prevalence of hyperhidrosis and impact on individuals with axillary hyperhidrosis: Results from a national survey. J Am Acad Dermatol; 51(2); pp. 241R248; Feb. 2004.
Stuchly et al.; Diathermy applicators with circular aperture and corrugated flange; IEEE Trans on Microwave Theory and Techniques; MTT-28(3); pp. 267-271; Mar. 1980.
Stuchly et al.; Dielectric properties of animal tissues in vivo at frequencies 10 MHz-1 GHz; Bioelectromagnetics; 2(2); pp. 93-103; Apr. 1981.
Stuchly et al.; Dielectric properties of animal tissues in vivo at radio and microwave frequencies: comparison between species; Phys. Med. Biol.; 27(7); pp. 927-936; Jul. 1982.
Sullivan et al.; Comparison of measured and simulated data in an annular phased array using an inhomogeneous phantom; IEEE Trans on Microwave Theory and Techniques; 40(3); pp. 600-604; Mar. 1992.
Sullivan et al.; The pig as a model for human wound healing; Wound Repair Regen; 9(2); pp. 66R76; Mar. 2001.
Sunaga et al.; Development of a dielectric equivalent gel for better impedance matching for human skin; Bioelectromagnetics; 24; pp. 214-217; Apr. 2003.
Surowiec et al.; Dielectric properties of breast carcinoma ind the surrounding tissues; IEEE Trans on Biomedical Engineering; 35(4); pp. 257-263; Apr. 1988.
Tavernier et al.; Conductivity and dielectric permittivity of dermis and epidermis in nutrient liquid saturation; Engineering in Medicine and Biology Society; 1992 14th Annual Int. Conf of the IEEE; Paris, France; pp. 274-275; Oct. 29-Nov. 1, 1992.
Thermolase Corp.; 510K Pre-Market Notification (No. K950019) and Product User Manual ThermoLase Model LT100 Q-Switched Nd: YAG, Laser Hair Removal System, Jan. 3, 1995.
Trembly et al.; Combined Microwave Heating and Surface Cooling of the Cornea; IEEE Transactions on Biomedical Engineering; vol. 38; No. 1; pp. 85-91; Jan. 1991.
Urolgix, Inc.; Cooled Thermotherapy+Prostiva RF=Durability+Versatility; 1 pg.; printed Jun. 18, 2012 from website (http://www.urologix.com/).
Uzunoglu et al.; A 432-MHz Local Hyperthermia System Using an Indirectly Cooled, Water-Loaded Waveguide Applicator; IEEE Trans. on Microwave Theory and Techniques; vol. 35, No. 2; pp. 106-111; Feb. 1987.

Valleylab; Cool-tip} RF Ablation System; (http://www.cool-tiprf.com/physics.html) accessed Jun. 24, 2008.
Van Rhoon et al.; A 433 MHz Lucite Cone Waveguide Applicator for Superficial Hyperthermia; International Journal of Hyperthermia; vol. 14, No. 1; pp. 13-27; Jan.-Feb. 1998.
Vander Vorst et al.; RF/microwave interaction with biological tissues; Hoboken, NJ; John Wiley & Sons, Inc.; pp. 264-305; Jan. 2006.
Vardaxis et al.; Confocal laser scanning microscopy of porcine skin: Implications for human wound healing studies; J Anat; 190(04); pp. 601R611; May 1997.
Vrba, et al.; Evanescent-Mode Applicators (EMA) for Superficial and Subcutaneous Hyperthermia; IEEE Trans. on Biomedical Engineering; vol. 40; No. 5; pp. 397-407; May 1993.
Weiss et al.; Monopolar radiofrequency facial tightening: a retrospective analysis of efficacy and safety in over 600 treatments; J Drugs Dermatol; 5(8); pp. 707-712; Sep. 2006.
Wonnell et al.; Evaluation of microwave and radio frequency catheter ablation in a myocardium-equivalent phantom model; IEEE Trans. on Biomedical engineering; 39(10); pp. 1086-1095; Oct. 1992.
Yang et al.; A Floating Sleeve Antenna Yields Localized Hepatic Microwave Ablation; IEEE Transactions on Biomedical Engineering; 53(3); pp. 533-537; Mar. 2006.
Zelickson et al.; Histological and ultrastructural evaluation of the effects of a radiofrequency-based nonablative dermal remodeling device; Arch Dermatol; 140; pp. 204-209; Feb. 2004.
Zelickson et al.; Ultrastructural effects of an infrared handpiece on forehead and abdominal skin; Dermatol Surg; 32(7); pp. 897-901; Jul. 2006.
Zhou et al.; Resection of Meningiomas with Implantable Microwave Coagualation; Bioelectromagnetics; vol. 17; No. 2; pp. 85-88; (month unavailable) 1996.
Ben-Haim et al.; U.S. Appl. No. 13/563,656 entitled "Applicator and Tissue Interface Module for Dermatological Device," filed Jul. 31, 2012.
Deem et al.; U.S. Appl. No. 13/762,264 entitled "Systems and Methods for Creating an Effect Using Microwave Energy to Specified Tissue," filed Feb. 7, 2013.
Johnson et al.; U.S. Appl. No. 13/772,238 entitled "Systems, Apparatus, Methods and Procedures for the Noninvasive Treatment of Tissue Using Microwave Energy," filed Feb. 20, 2013.
Houzen et al.; Implanted antenna for an artificial cardiac pacemaker system; Progress in Electromagnetics Research Symposium 2007; Prague, CZ; pp. 51-54; Aug. 27-30, 2007.
Kim et al.; Implanted antennas inside a human body: Simulations, designs, and characterizations; IEEE Trans on Microwave Theory and Techniques; 52(8); pp. 1934-1943; Aug. 2004.
Soontornpipit et al.; Design of implantable microstrip antenna for communication with medical implants; IEEE Trans on Microwave Theory and Techniques; 52(8); pp. 1944-1951; Aug. 2004.
Virga et al.; Low-profile enhanced-bandwith PIFA antennas for wireless communications packaging; IEEE Trans on Microwave Theory and Techniques; 45(10); pp. 1879-1888; Oct. 1997.
Wikipedia; ISM band; 5 pages; printed Jul. 22, 2014 from website (http://en.wikipedia.org/wiki/ISM_band).
Wikipedia; Bayonet mount; 6 pages; Dec. 18, 2014; retrieved from the internet (www.http://en.wikipedia.org/wiki/Bayonet mount).
Gabriel; Compilation of the dielectric properties of body tissues at RF and microwave frequencies (Technical Report); Armstrong Laboratory; Doc. No. AL/OE-TR-1996-004; pp. 1-16; Jan. 1996.
Gandhi et al.; Electromagnetic Absorption in the Human Head from Experimental 6-GHz Handheld Transceivers; IEEE Trans. On Electromagnetic Compatibility; 37(4); pp. 547-558; Nov. 1995.
Klemm et al.; EM energy absorption in the human body tissues due to UWB antennas; Progress in Electromagnetics Research; PIER; 62; pp. 261-280; 2006.
Wright et al.; Hepatic microwave ablation with multiple antennae results in synergistically larger zones of coagulation necrosis; Ann. Surg. Oncol.; 10(3); pp. 275-283; Apr. 2003.

* cited by examiner

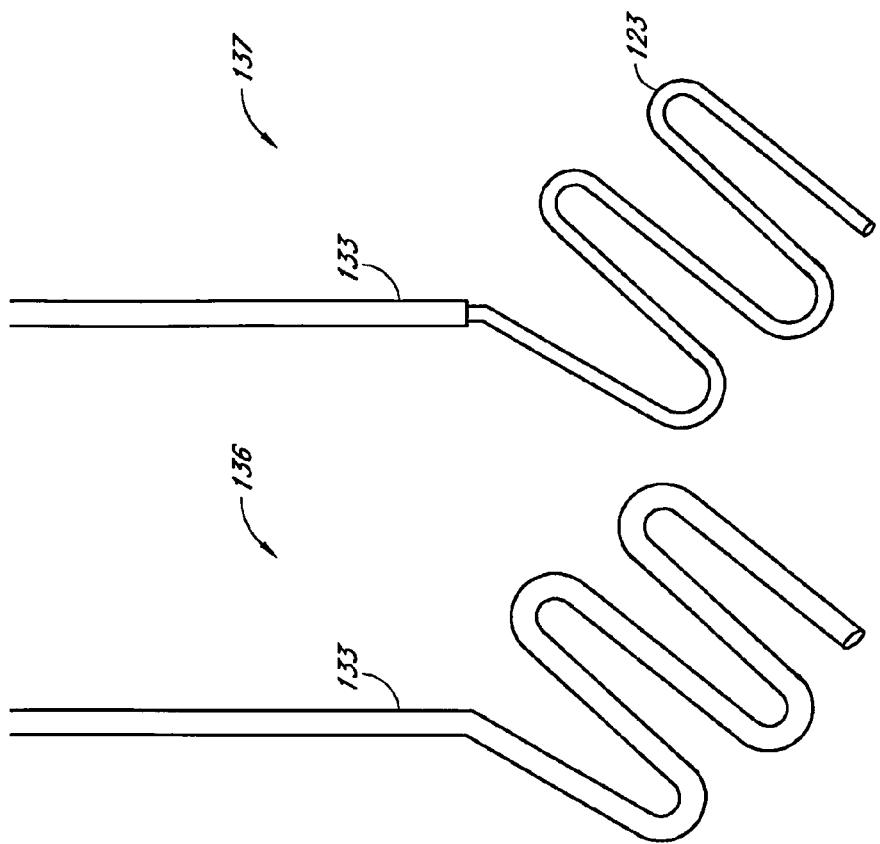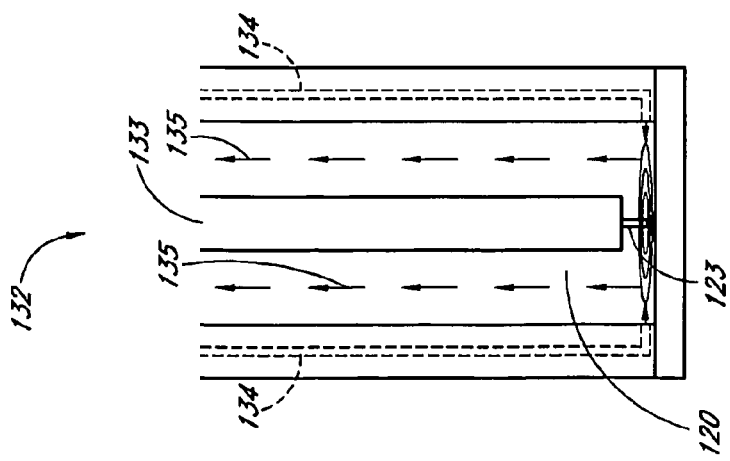

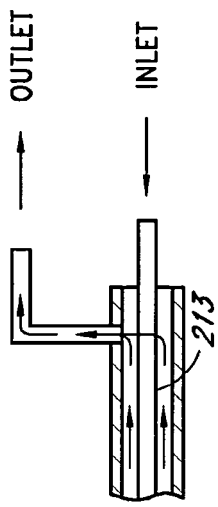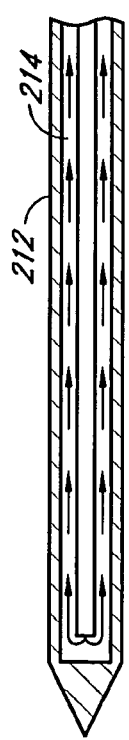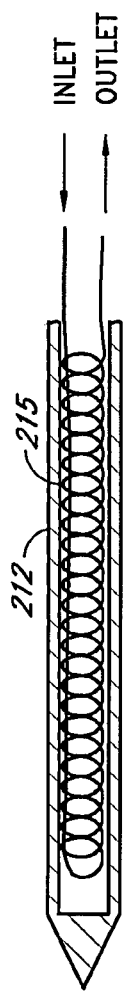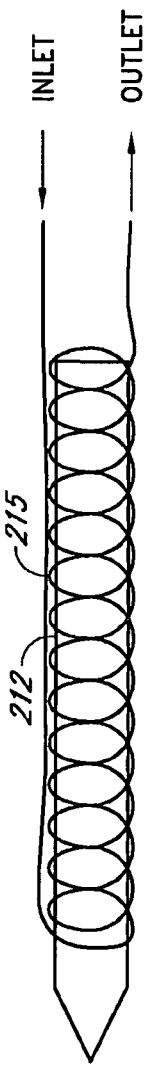
FIG. 12A  FIG. 12B  FIG. 12C

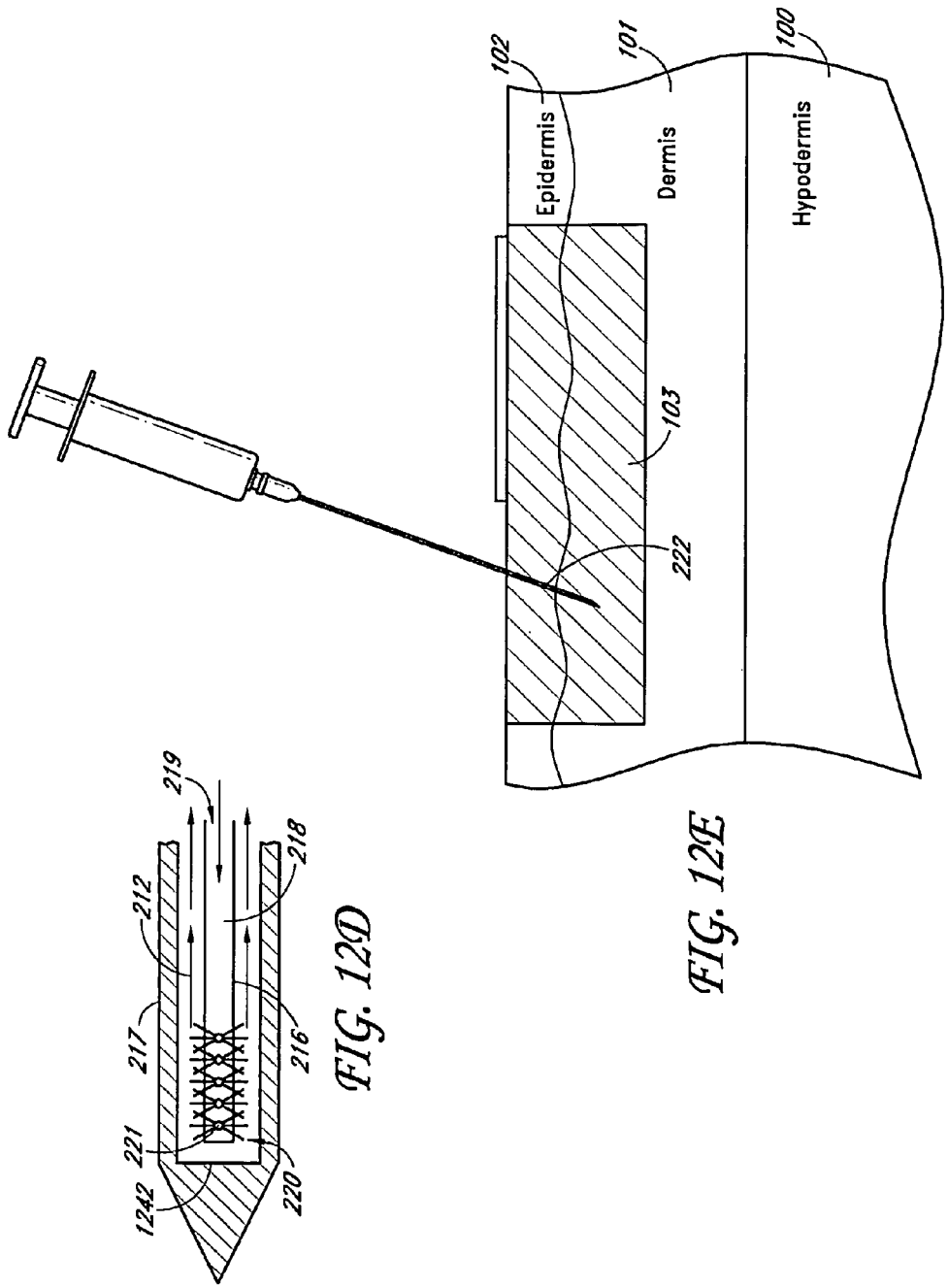

FIG. 15
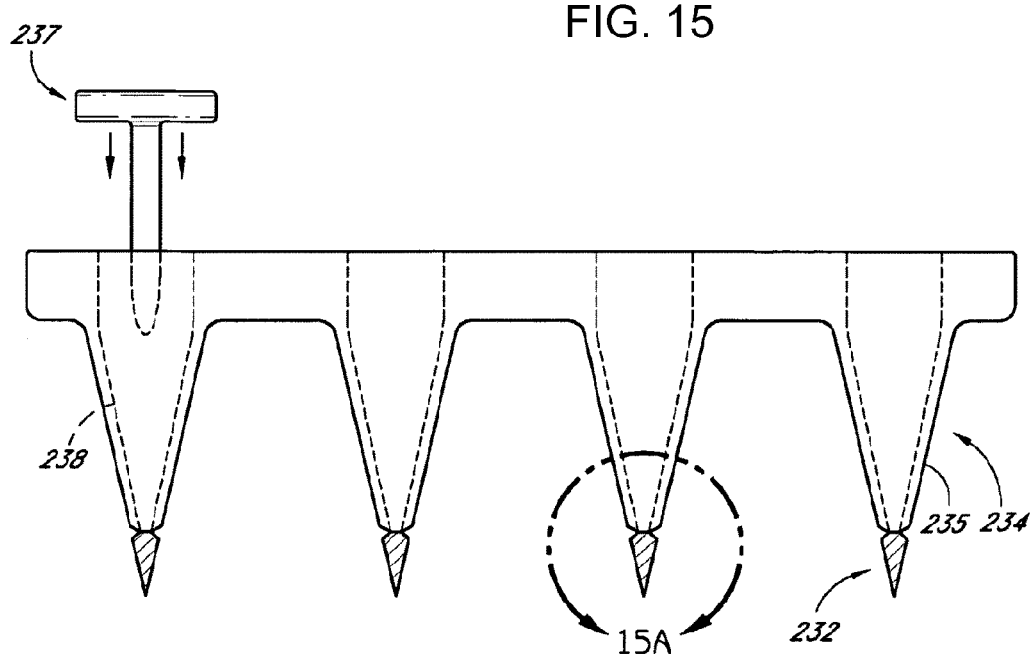
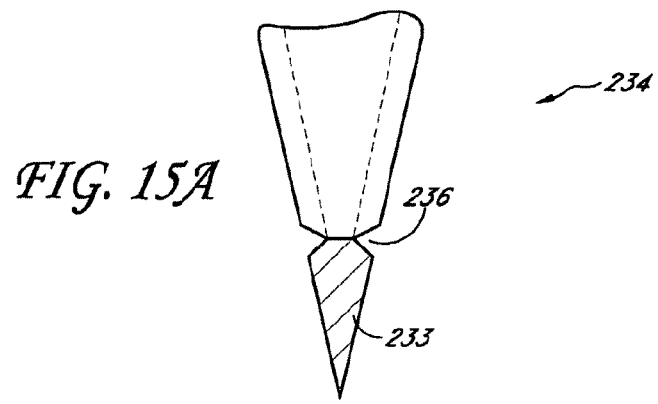
FIG. 15A

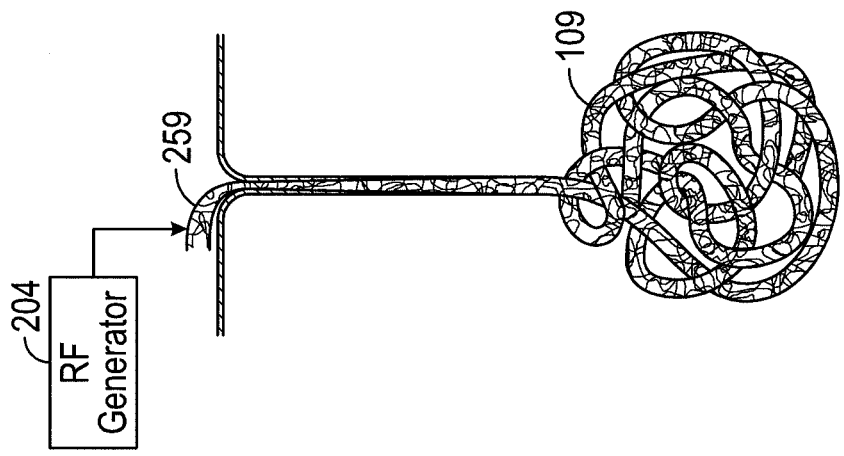
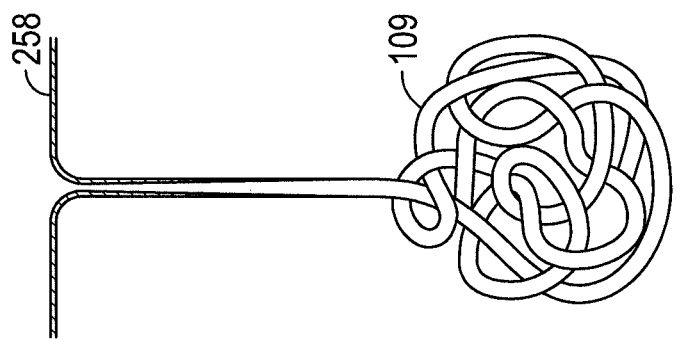
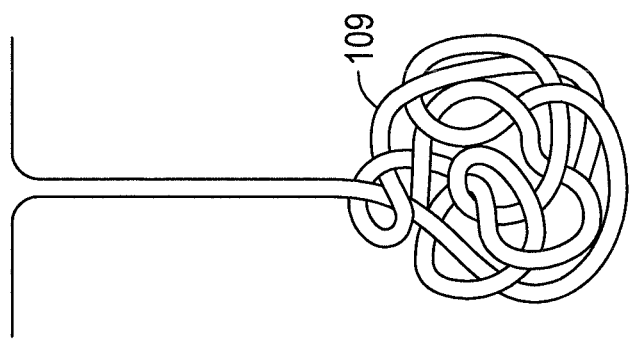
FIG. 20C
FIG. 20B
FIG. 20A

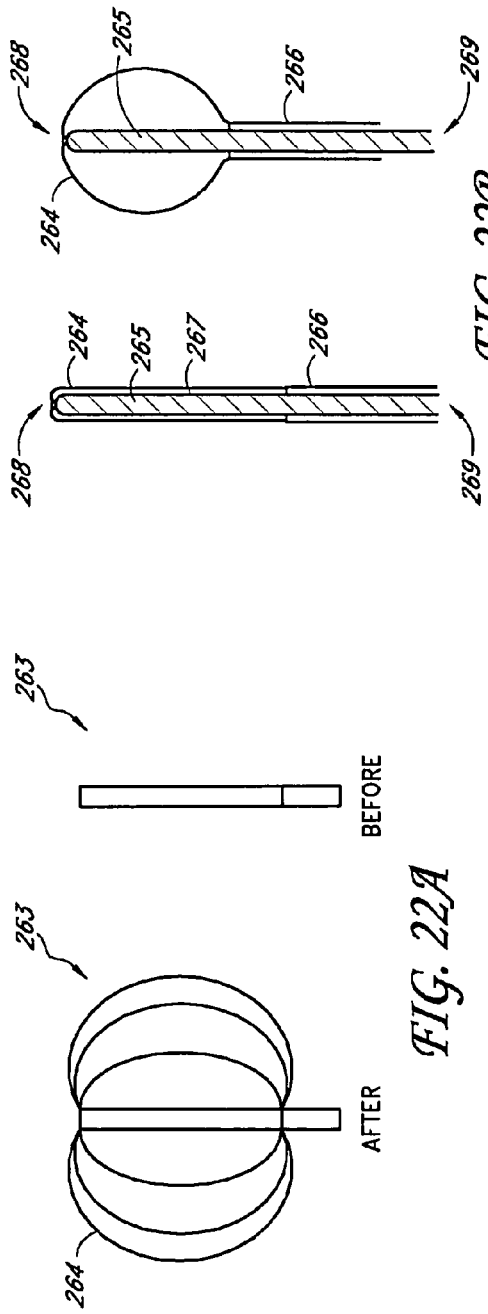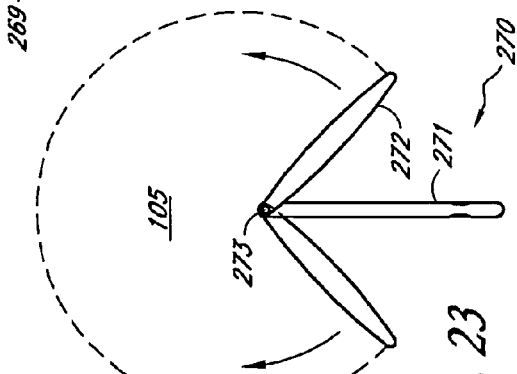

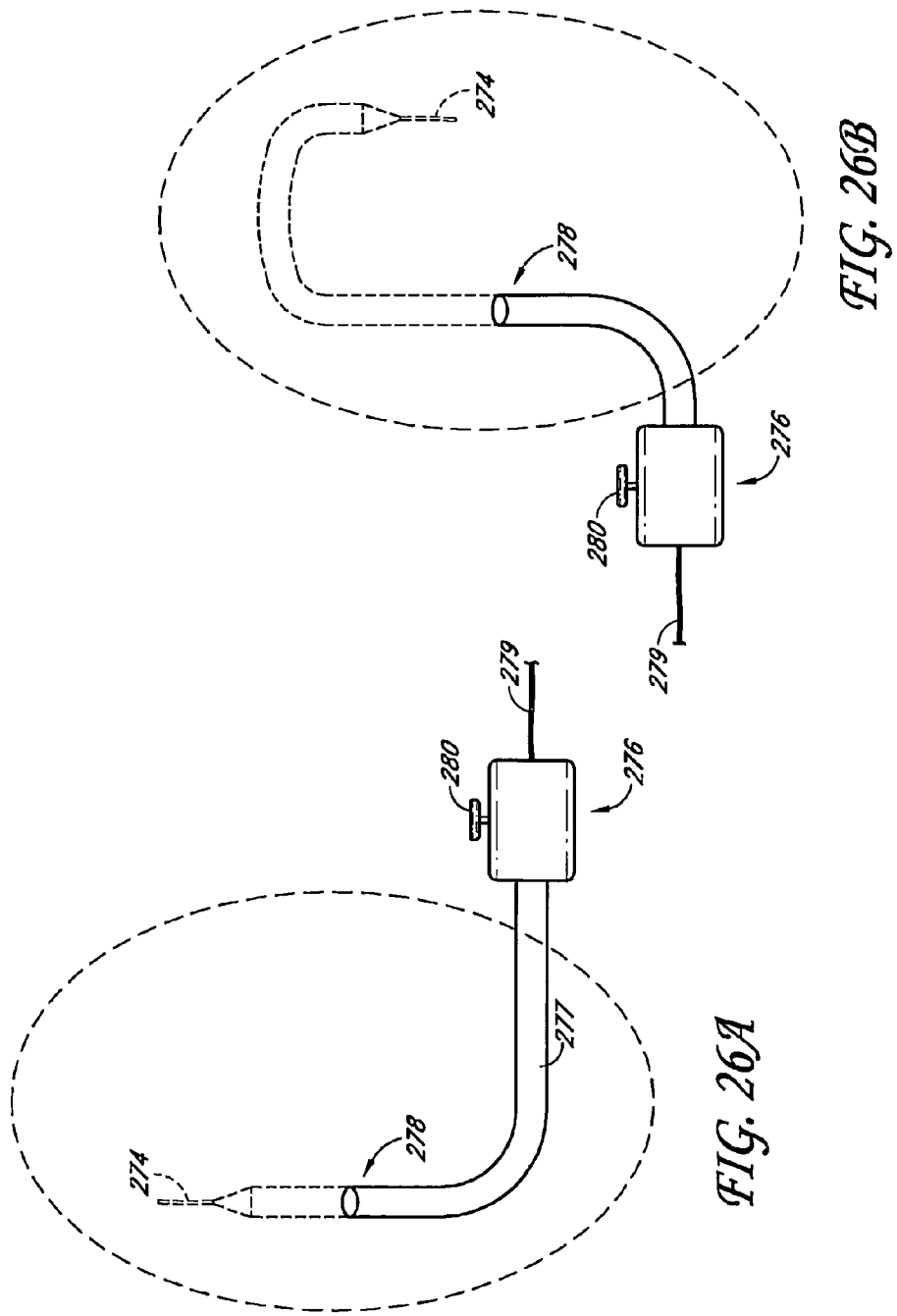

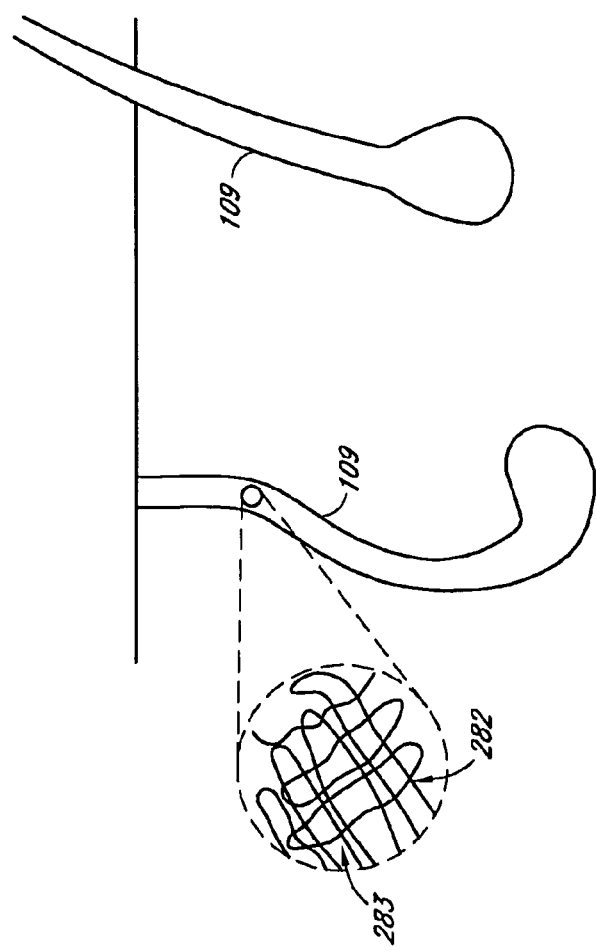

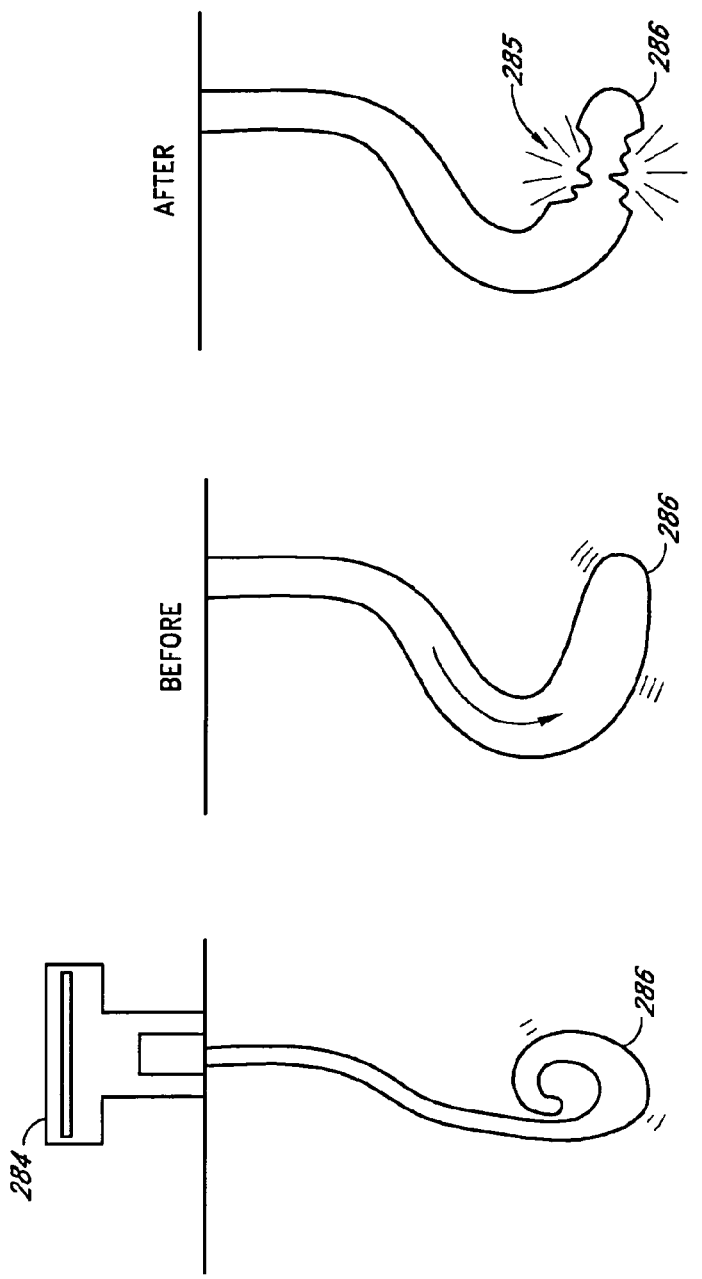

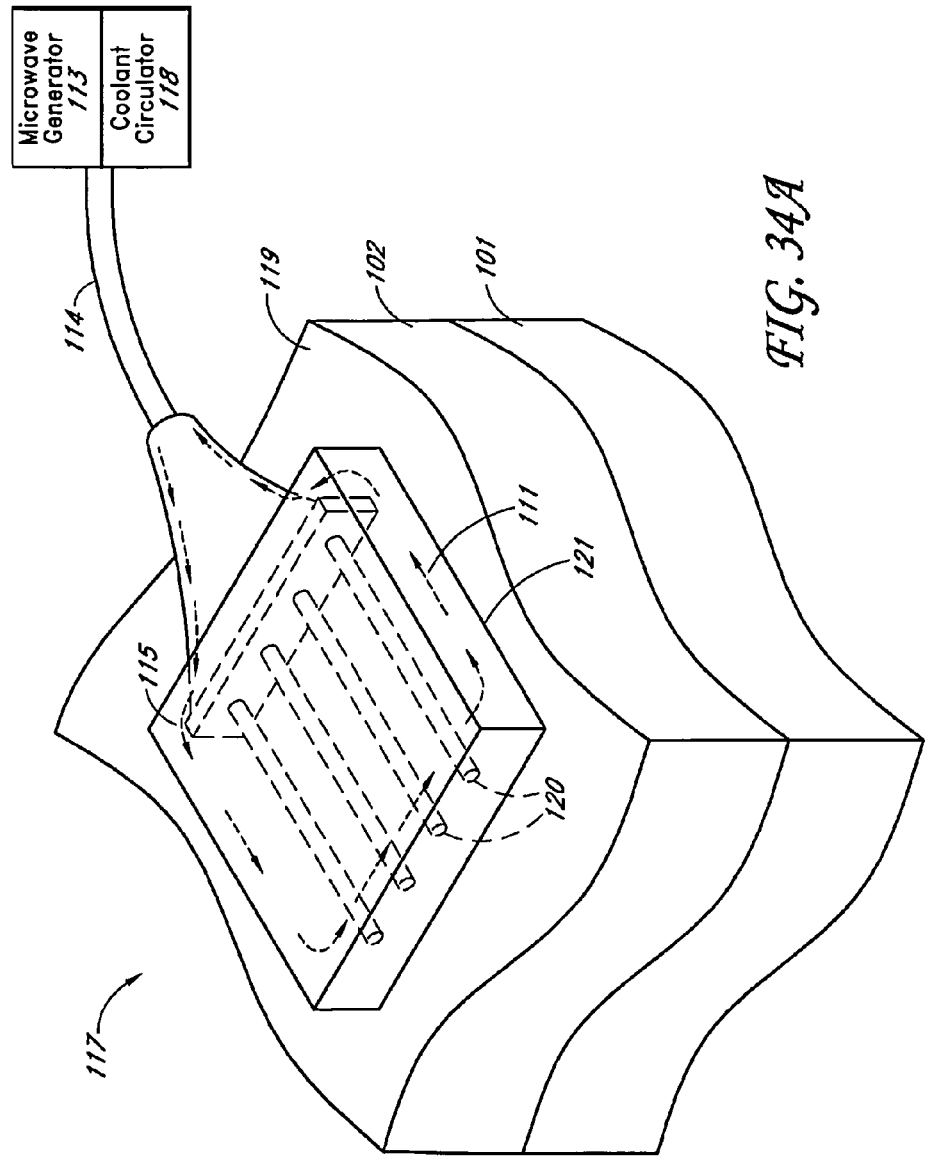

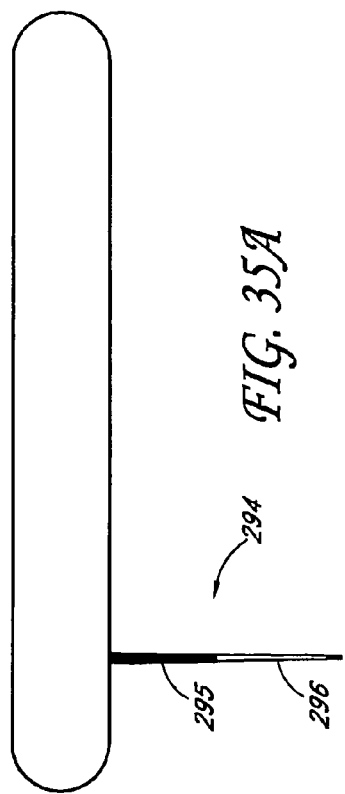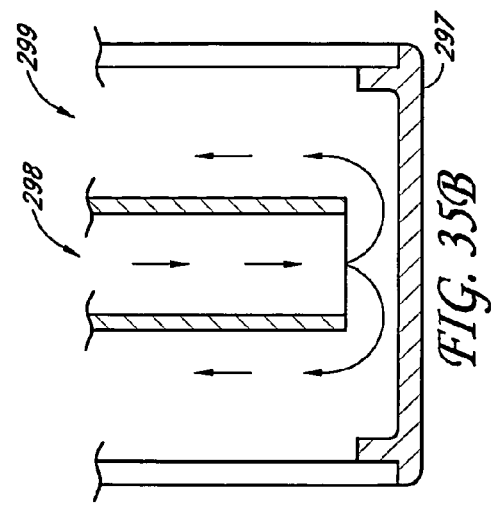
FIG. 35A
FIG. 35B

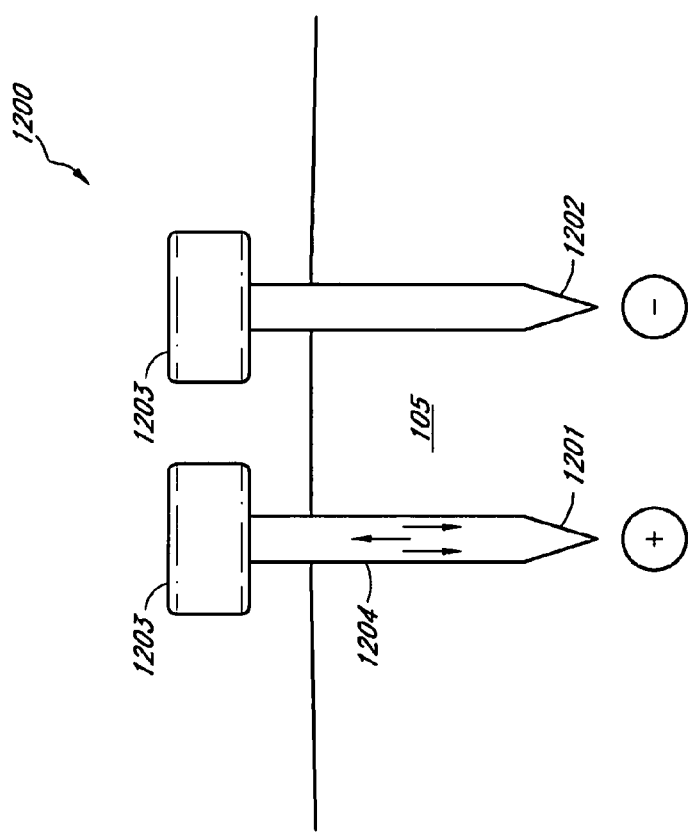

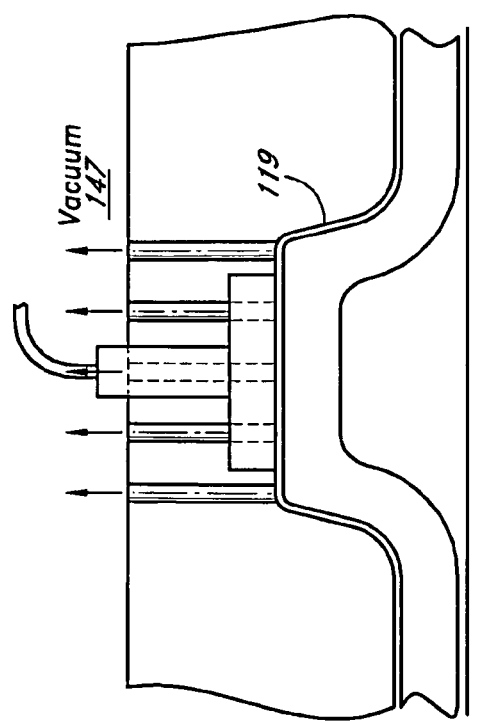

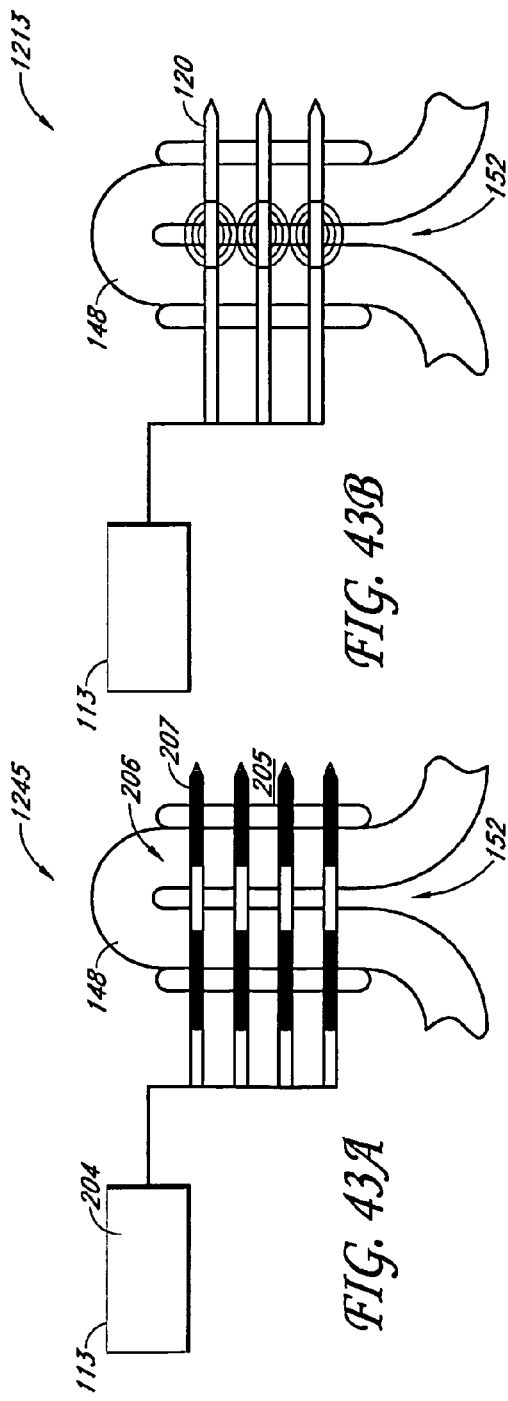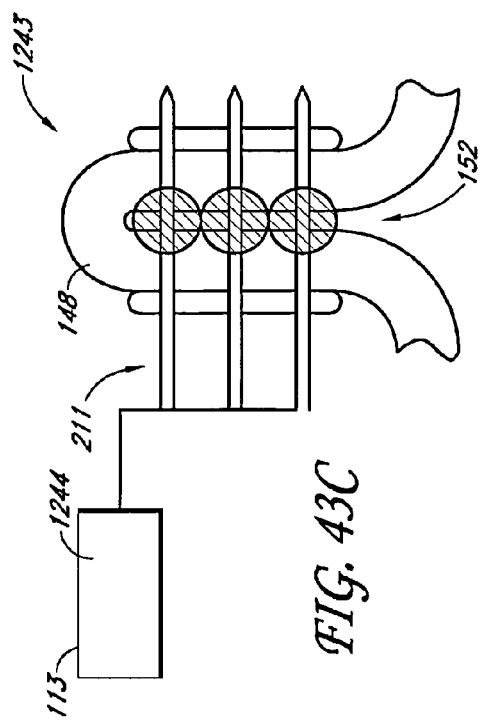
FIG. 43A  
FIG. 43B  
FIG. 43C

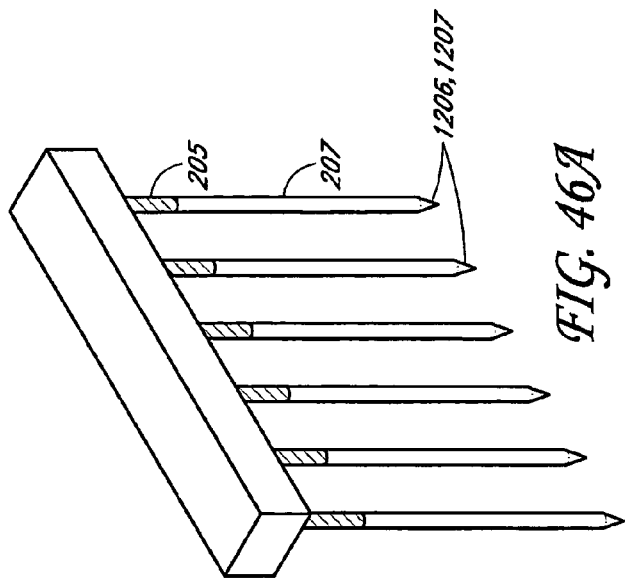
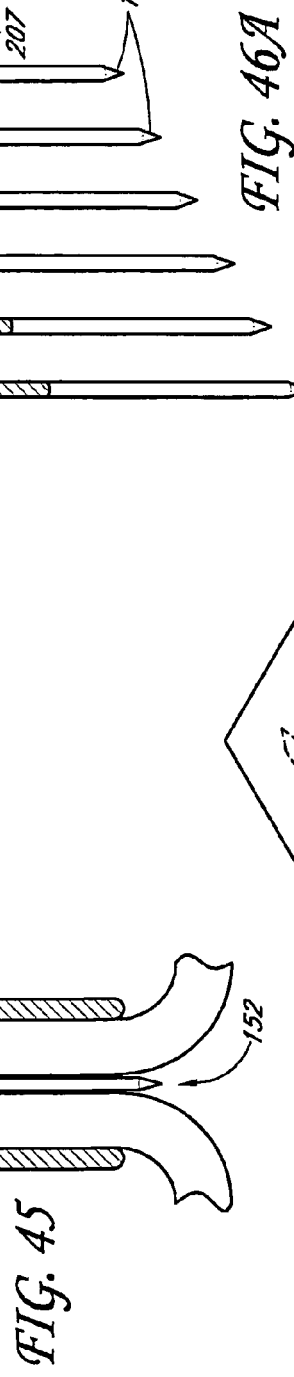
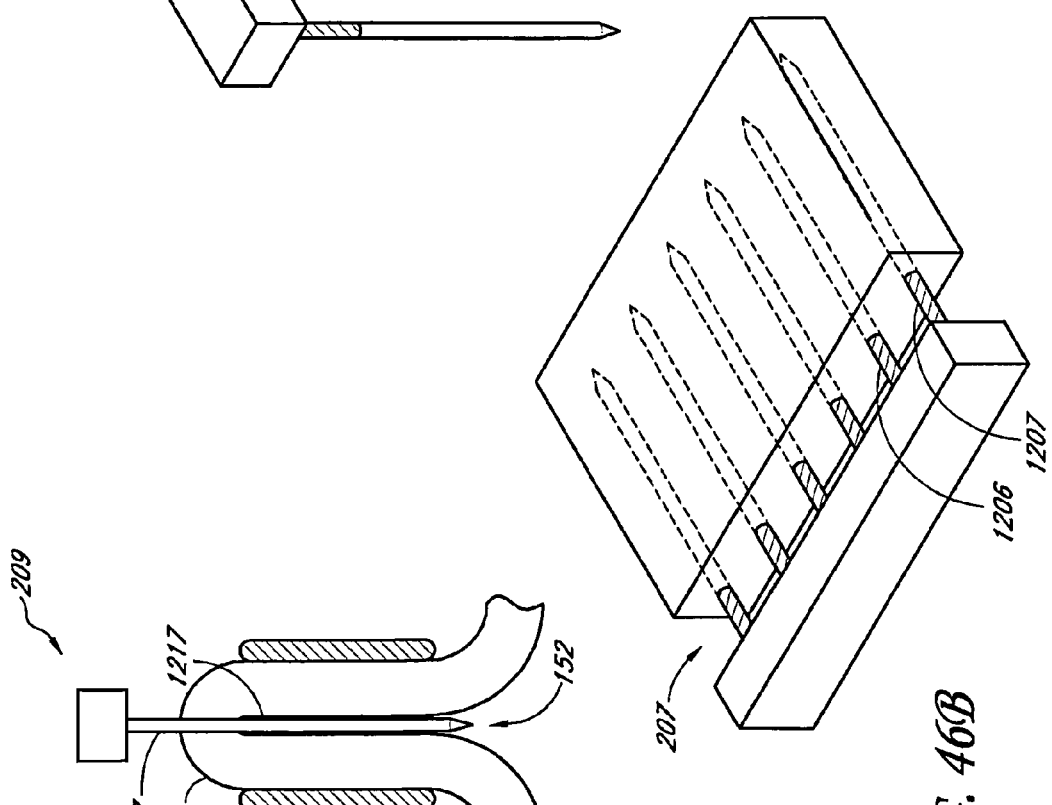

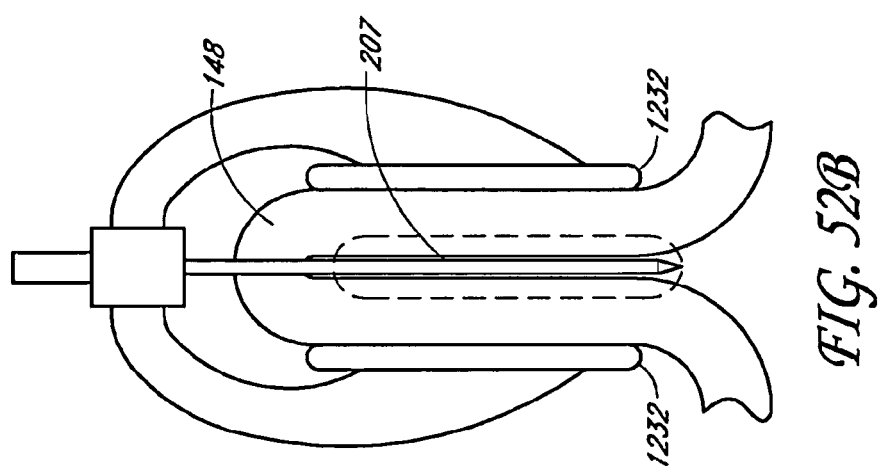

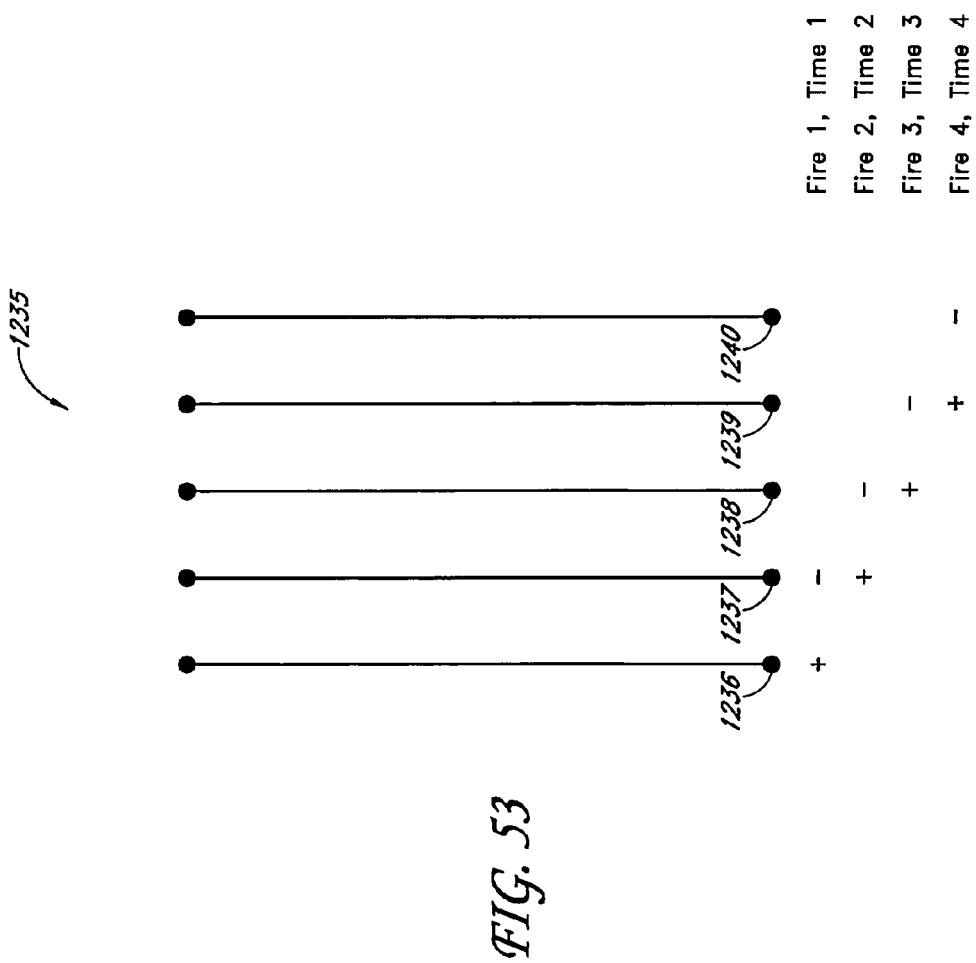

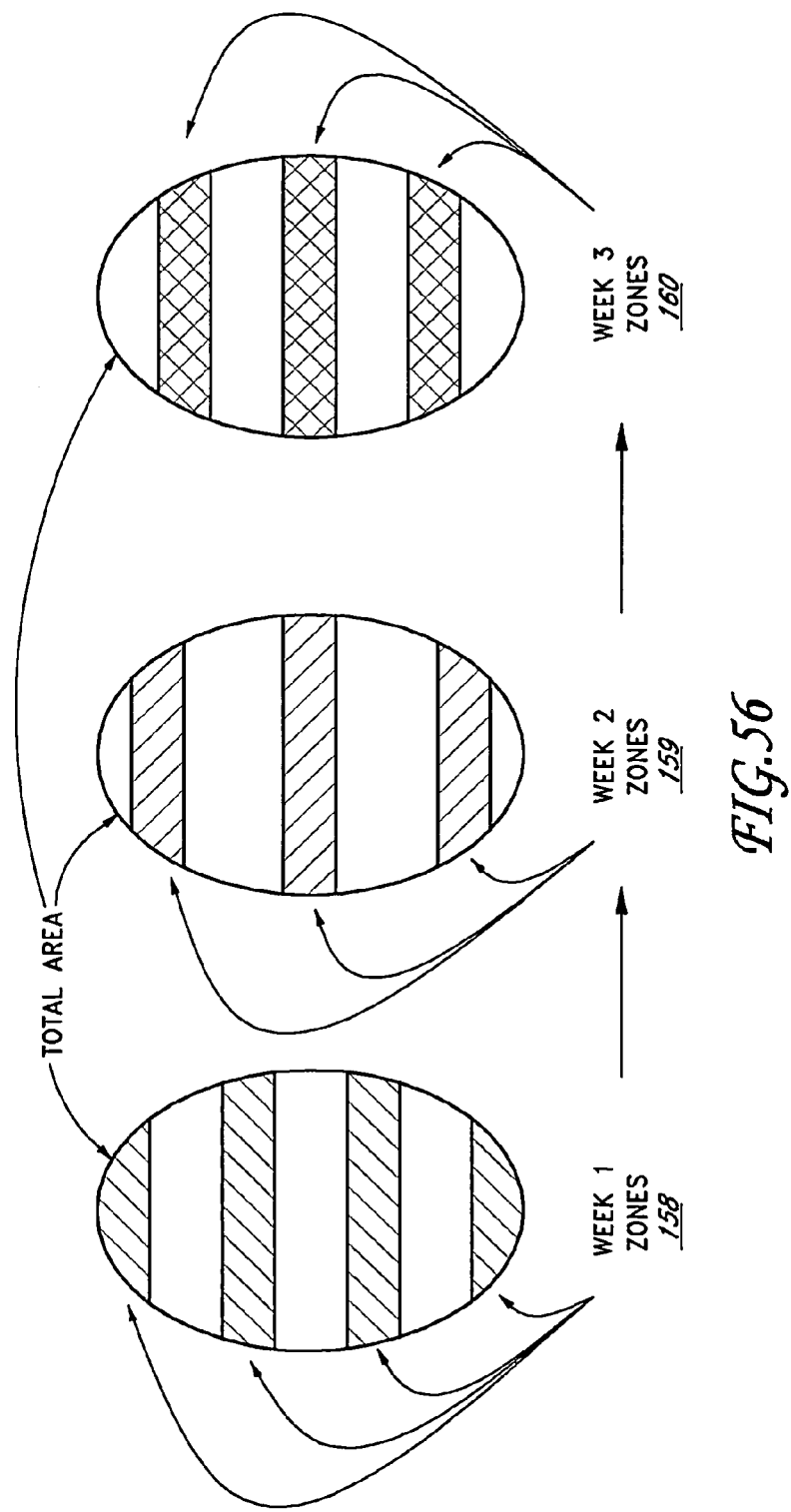

METHODS AND APPARATUS FOR REDUCING SWEAT PRODUCTION

The present application claims priority under 35 U.S.C. §119(e) to U.S. Provisional Patent Application Ser. No. 60/912,899, entitled "Methods and Apparatus for Reducing Sweat Production," filed Apr. 19, 2007, U.S. Provisional Patent Application Ser. No. 61/013,274, entitled "Methods, Delivery and Systems for Non-Invasive Delivery of Microwave Therapy," filed Dec. 12, 2007, and U.S. Provisional Patent Application Ser. No. 61/045,937, entitled "Systems and Methods for Creating an Effect Using Microwave Energy in Specified Tissue," filed Apr. 17, 2008. The entire disclosures of all of the priority applications are hereby expressly incorporated by reference in their entireties.

BACKGROUND

1. Field of the Invention

The present application relates to methods and apparatuses for reducing sweat production. In particular, the present application relates to methods and apparatuses for reducing sweat production via the removal, disablement, incapacitation of apocrine and eccrine glands in the dermal and subcutaneous tissue.

2. Description of the Related Art

It is known that energy-based therapies can be applied to tissue throughout the body to achieve numerous therapeutic and/or aesthetic results. There remains a continual need to improve on the effectiveness of these energy-based therapies and provide beneficial pathological change with minimal adverse side effects or discomfort.

BRIEF DESCRIPTION OF THE DRAWINGS

These and other features, aspects and advantages of the various devices, systems and methods presented herein are described with reference to drawings of certain embodiments, which are intended to illustrate, but not to limit, such devices, systems, and methods. It is to be understood that the attached drawings are for the purpose of illustrating concepts of the embodiments discussed herein and may not be to scale.

FIG. 7A shows a cross-sectional view of an antenna having an inner conductor disposed within a coaxial cable according to one embodiment.

FIG. 7B shows a coiled antenna having a coiled conductor element formed entirely from a coaxial cable according to one embodiment.

FIG. 7C shows a coiled antenna having a coiled conductor element formed from an inner conductor according to one embodiment.

FIG. 12A shows a cryogenic system configured to have an interstitial element comprising at least two concentric tubes according to one embodiment.

FIG. 12B shows a cryogenic system configured to have an interstitial element configured with a tubular coil residing inside the element.

FIG. 12C shows a cryogenic system configured to have an interstitial element configured with a tubular coil residing partially inside and partially outside the element.

FIG. 12D shows a cryogenic system configured to have an inner portion and outer portion such that nitrous oxide gas exits the distal portion of the inner tube and absorbs thermal energy from the distal portion of the outer tube.

FIG. 12E shows the injection of a cryoprotective agent according to one embodiment.

FIGS. 15 and 15A show needles comprised of at least one chromophore on their tips according to one embodiment.

FIG. 20A shows a sweat duct.

FIG. 20B shows the sweat duct of FIG. 20A having a layer of insulation according to one embodiment.

FIG. 20C shows a sweat duct of FIG. 20B having a layer of insulation and being treated with electrical energy according to one embodiment.

FIG. 22A shows a wire device having an actuator to bow out the wire into an expanded profile according to one embodiment.

FIG. 22B shows an actuator having an outer element and inner element according to one embodiment.

FIG. 23 shows a planar cutting device comprising a pinwheel cutter according to one embodiment.

FIG. 26A shows a tunneling instrument having an actuator according to one embodiment.

FIG. 26B shows a tunneling instrument having an actuator according to another embodiment.

FIG. 28 shows biocompatible scaffolding introduced into a sweat duct according to one embodiment.

FIG. 29 shows a piston used to deliver pressurized gas to a sweat gland according to one embodiment.

FIG. 30A shows a sweat gland having liquid according to one embodiment.

FIG. 30B shows the sweat gland of FIG. 30A ruptured after the liquid has frozen.

FIG. 34A shows an isometric view of a non-invasive energy delivery device comprising multiple microwave antennas electrically connected to a microwave generator according to one embodiment.

FIG. 35A shows a needle configured with a proximal region comprising a cooling element and a distal end comprising an electrode tip according to one embodiment.

FIG. 35B shows an energy delivery device element comprising a metal electrode, an inner tube and an outer circumferential surface according to one embodiment.

FIG. 36 shows an energy delivery device comprising a bipolar pair of needle-tipped electrodes according to one embodiment.

FIG. 38 shows a side view of a vacuum pulling and holding skin according to one embodiment.

FIG. 43A shows a minimally-invasive RF delivery device comprising one or more needles for insertion into a skin fold according to one embodiment.

FIG. 43B shows a minimally-invasive microwave delivery device comprising one or more microwave antennas for insertion into a skin fold according to one embodiment.

FIG. 43C shows a minimally-invasive cryogenic therapy device comprising one or more injection needles, catheters, stylets, cannulas or catheters according to one embodiment.

FIG. 45 shows an energy delivery device according to one embodiment inserted at the top of a skin fold.

FIG. 46A shows an array of monopolar electrode needles used to deliver treatment along the longitudinal length of a skin fold according to one embodiment.

FIG. 46B shows an array of monopolar electrode needles used to deliver treatment along the longitudinal length of a skin fold according to another embodiment.

FIG. 52B shows a side view of a clamp used to create and hold a skin fold according to a second embodiment.

FIG. 53 shows an array of electrodes configured to deliver energy according to one embodiment.

FIG. 56 shows three templates to be used in a staged treatment, wherein each template is configured to allow treatment to a different portion of the overall treatment area according to one embodiment.

DETAILED DESCRIPTION OF PREFERRED EMBODIMENTS

Overview of Treatments

Figure 1:
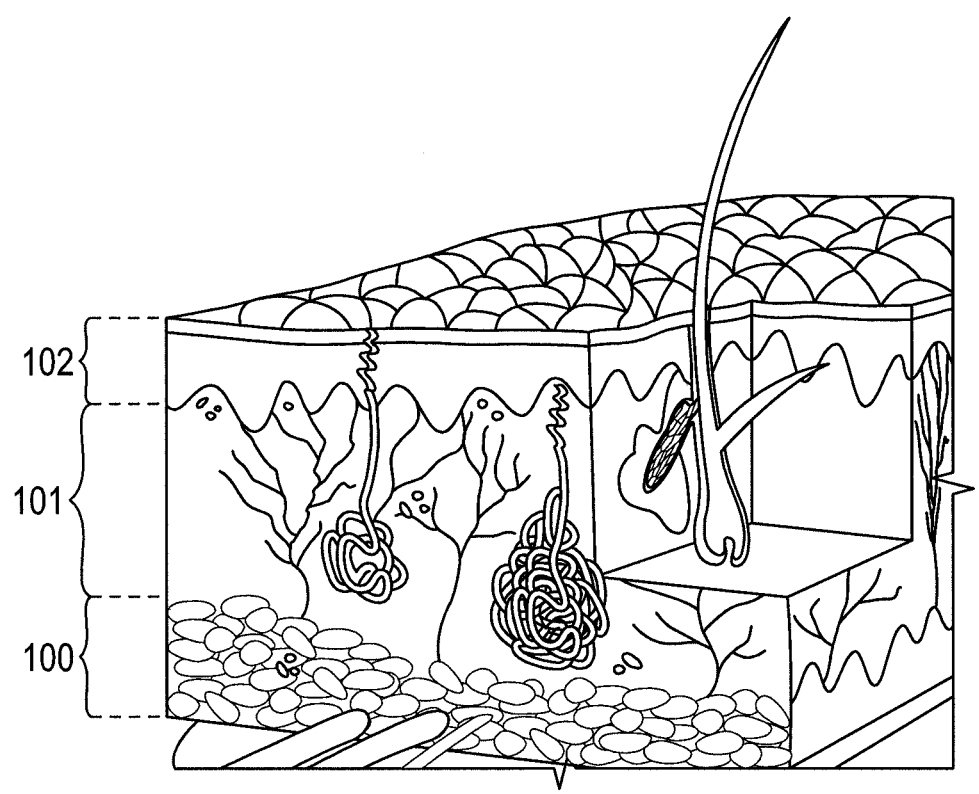
FIG. 1 shows a cross-sectional view of the skin, its internal structures and surrounding tissue.

Sweating is both a normal thermoregulation process for human beings and a normal physiological response to a psychological stress or emotional stimuli. For most people, sweating is only a minor cosmetic annoyance. For others, however, sweating may be excessive and abnormal and, consequently, become a socially embarrassing condition. Some embodiments of the present invention relate to methods for reducing sweat production via the removal, disablement, incapacitation or destruction of sweat glands in the subcutaneous tissue of a human being.

Hyperhidrosis is a clinically diagnosed disorder in which there is excessive secretion of sweat from the sweat glands. The excessive sweating, which is thought to result from the over activity of the sympathetic nervous system, usually occurs in the palms, soles, and axillae. Palmar hyperhidrosis is a condition of excessive sweating in the hand. This condition is often exhibited in cold, wet handshakes. Plantar hyperhidrosis is a condition of excessive sweating in the foot. This condition may cause blisters and fungal infections. Axillary hyperhidrosis is a condition of excessive sweating in the armpit. Such excessive sweating is not only socially embarrassing, but may even cause staining and rotting of clothes.

The sweat glands in the body are comprised of the apocrine and eccrine glands. Eccrine sweat glands, which lie superficially in the dermis layer of the skin, are located all over the body so that they can secrete sweat to regulate body heat and temperature. Apocrine glands, which exist within the subcutaneous tissue and border on the interface between the subcutaneous tissue layer and dermal layer, secrete an oily, milky, protein-rich product into the follicles. Bacterial digestion of apocrine sweat is largely responsible for osmidrosis or bromohidrosis (i.e., body odor), which can be most pronounced in the foot and underarm area.

There are various treatments used for treating hyperhidrosis. For example, chemical antiperspirants and deodorants are commonly used as a matter of personal hygiene. Antiperspirants are aluminum based salts that mechanically block the sweat gland ducts, thereby preventing sweat from reaching the skin surface. Deodorants change the pH of the skin surface, thereby minimizing the presence of smell inducing bacteria. Because the effects of both of these products are temporary and can irritate the skin in some users, these products are suboptimal solutions to cases of excessive sweating.

In addition to antiperspirants and deodorants, other topical preparations have been used to treat hyperhidrosis. For example, glutaraldehyde and tannic acid have been used in the treatment of plantar and palmar hyperhidrosis. However, these treatments have generally lost favor because they may cause an unsightly browning of the skin.

Anticholinergic drugs have also been applied both topically and systemically to treat hyperhidrosis. These agents block the sympathetic stimulation of the eccrine glands by inhibiting the action of acetylcholine at the nerve synapse. Use of these drugs is limited because of the systemic side effects they can cause, including, dry mouth, urinary retention, constipation, and visual disturbances such as mydriasis and cycloplegia. Moreover, topical anticholinergics sometimes have difficulty absorbing into the skin in sufficient quantities to affect the cholinergic nerve endings.

Some patients with hyperhidrosis have resorted to surgical treatments such as sweat gland excision and thoracic sympathectomy. For example, U.S. Pat. No. 5,190,518 to Takasu, which is herein incorporated by reference in its entirety, discloses an ultrasonic surgical device for disabling and excising sweat glands. These treatments may provide for a longer duration of alleviation from hyperhidrosis. However, these treatments are rarely indicated due to their invasive nature, adverse consequences and cost. For example, surgery may cause contractures of the skin, muscle or other surrounding tissue. Sympathectomy may result in complications including infection, pneumothorax, Horner's syndrome, and compensatory hyperhidrosis of the trunk, back and thighs.

Recently, botulinum type-A neurotoxin (e.g., BOTOX™) has proved effective in treating hyperhidrosis in some patients. BOTOX is commonly used by dermatologists to denervate the neuroglandular junctions between the autonomic nerves and the sweat glands. With the nerve connections disabled, acetylcholine is prevented from reaching the eccrine sweat glands, thereby disabling a component of the hyperhidrosis patient's overactive sympathetic nervous system. This treatment, however, is not without its downsides. Botulinum toxin is one of the most lethal substances on earth and, consequently, injecting it in a patient's body is full of risk. Additionally, since the apocrine sweat glands are innervated by adrenergic nerves, which are not blocked by botulinum toxin, injections of botulinum toxin do not have a clinical impact on the body odor caused by the secretions from apocrine glands. Botulinum toxin treatment also requires multiple, painful injections with a needle. Furthermore, the results of this treatment last only a few months, thereby necessitating repeated costly and painful treatments.

In light of the shortcomings of the aforementioned approaches, a minimally-invasive, convenient, effective, long-lasting treatment with few side effects would be a desirable alternative for treating hyperhidrosis.

Discussion of Anatomy

FIG. 1 is an isometric view of a cross-section of the skin, its internal structures and surrounding tissue. The skin comprises three principal layers, the epidermis 102, dermis 101 and subcutaneous tissue 100. The epidermis 102 is the thin, epithelial surface of the skin. The epidermis 102 is comprised of several sub-layers, including, the stratus corneum, keratinocytes layer and basal layer. The epidermis 102 also contains melanin producing melanocyte cells, which are responsible for skin pigmentation. The thickness of the epidermis 102 ranges from 0.05 mm to 1.5 mm depending on the location of the skin on the body.

The dermis 101 is the middle layer of the skin and is composed of blood vessels, lymph vessels, hair follicles, sebaceous glands, eccrine glands and, occasionally, apocrine glands. The dermis 101 is held together by fibroblast cells that may be present as collagen protein, elastic tissue and/or reticular fibers. The dermis 101 layer also contains neural receptors corresponding to the pain and touch senses. The dermis 101 varies in thickness depending on the location of the skin. The thickness of the dermis 101 can range from 0.3 mm at the eyelid to 3.0 mm on the back.

The subcutaneous tissue 100 is a layer of fat and connective tissue that houses larger blood vessels and nerves. While apocrine glands will sometimes be located in the dermis layer of the skin, it is more common for these glands to reside in the subcutaneous tissue. This layer 100 provides a thermal barrier to help conserve body heat and additional cushion to protect the organs from injury due to trauma. Beneath the subcutaneous layer lies the muscular frame of the body.

Eccrine glands are distributed over the entire body surface with a density ranging from 50 glands per square centimeter to 200 glands per square centimeter. These glands are most densely located on the palms of hands, soles of feet, forehead and underarms. An eccrine gland comprises three distinct portions: (1) the intraepidermal portion, (2) the intradermal duct (coiled and straight duct), and (3) the secretory portion (coiled gland). The coiled gland is located in the deep dermis or at the border of the dermis 101 and subcutaneous layer 100. The intradermal duct extends upward from the coiled gland through the dermis 101, first as the coiled duct, and then as the straight duct. The straight duct ends as it enters into the epidermis 102 and then spirals as it continues through the epidermis 102 and opens directly onto the skin surface.

Human eccrine sweat is composed of water, sodium, potassium lactate, urea, ammonia, serine, ornithine, citrulline, aspartic acid, heavy metals, organic compounds, and proteolytic enzymes. Generally, the concentration of sodium in eccrine sweat varies from 35-65 mmol/l.

The eccrine glands are controlled by sympathetic cholinergic nerves which are controlled by the hypothalamus. The hypothalamus senses core temperature directly and also obtains input from temperature receptors in the skin. Production of eccrine sweat is initiated by the hypothalamus through postganglionic fiber production of acetylcholine.

Apocrine glands are primarily present in the armpits and around the anogenital areas. These glands are comprised of: (1) a coiled gland in the deeper parts of the dermis or at the junction of the dermis and subcutaneous fat; and (2) a straight duct which traverses the dermis and empties into the isthmus (uppermost portion) of a hair follicle. The lumen of the coiled portion of the apocrine gland is approximately ten times the diameter of its eccrine counterpart. The straight duct runs from the coiled gland to the isthmus of the hair follicle and is virtually identical in appearance to the eccrine straight duct.

Emotional stressors stimulate the sympathetic adrenergic nerves, which initiate the release of viscous, fatty sweat from the apocrine glands. The amount of sweat produced by these glands is significantly smaller than that produced by the eccrine glands. Although odorless initially, apocrine sweat develops an odor when it comes into contact with the surface of the skin, wherein surface bacteria breaks down the organic compounds in the sweat and produces an odor.

Another type of sweat producing glands, the apoeccrine glands, are sometimes found in the axillae (underarms). These hybrid sweat glands are most commonly found in hyperhidrosis patients and are thought to play a role in axillary hyperhidrosis. Their secretory portion has both a small diameter portion similar to an eccrine gland, and a large diameter portion which resembles an apocrine gland. These glands are similar to eccrine glands in that they respond mainly to cholinergic stimuli, and their ducts are long and open directly onto the skin surface. However, apoeccrine glands secrete nearly ten times as much sweat as eccrine glands. Other non-limiting examples of tissue structures and medical conditions that may be treated using systems, methods, devices of some embodiments disclosed herein are described, for example, at pp. 1-10 of U.S. Provisional App. No. 61/013,274 which is incorporated by reference in its entirety.

Overview of Methods and Apparatuses

Embodiments of the present application relate to methods and apparatuses for reducing sweat production via the removal, disablement, incapacitation or destruction of apocrine and eccrine glands in the dermal and subcutaneous tissue. It is envisioned that many mechanisms and modalities can be implemented individually or in combination to achieve a reduction in sweat production in a patient. It is contemplated that the treatments disclosed herein could be applied to any part of the body that is responsible for or contributes to the production, secretion and/or presence of sweat.

In one approach for reducing sweat production, a target area on a target patient is first identified. More preferably, particular sweat glands or an area containing such sweat glands may be identified, and the sweat glands and/or surrounding tissue can be treated with energy. This energy can take many forms (e.g., electromagnetic, microwave, radiofrequency, laser, infrared, ultrasound, etc.) and can be delivered any number of ways (e.g., topically, minimally-invasively, etc.). Additionally, the devices employed in an energy treatment may include one or more electrodes, antennas, transducers, needles, probes, catheters, microneedles and stylets. Some of the other thermal treatments that can be employed include inductive heating, resistive heating, hyperthermic chemical reactions and/or cryogenic therapy.

In combination with the thermal treatments disclosed herein, protective treatments can be employed to prevent damage or pain to non-target tissue. In one embodiment, thermal protective treatments may be used. For example, surface cooling can be applied to protect the epidermal layer and portions of the dermal layer of the skin while deeper regions of skin tissue are heated via energy delivery. Various types of active and passive cooling or heating can be configured to provide this thermal protection to non-target tissue.

There are also numerous mechanical approaches for reducing sweat production. For example, the sweat glands can be surgically excised, sheared using various wires and/or blades, sealed and plugged shut, ruptured under pressure and disabled via acoustic cavitation.

A reduction in sweat production may be facilitated by administering many of the treatments disclosed herein in one or more spatial configurations or skin geometries. For example, treatment can be directed perpendicular to the skin surface, parallel to the skin plane or at some angle in between. Additionally, treatment can be administered to skin in a flat, planar configuration, in an elevated orientation or in a folded geometry.

A reduction in sweat production may also be facilitated by administering treatment over multiple stages and in a patterned arrangement. This approach can enhance the body's healing response, making for a quicker recovery with fewer complications. Various templates are disclosed to assist in administering a staged and patterned treatment.

With reference to the drawings disclosed in this specification, the particulars shown are by way of example and for purposes of illustrative discussion of certain embodiments. In this regard, not all structural details may be shown in detail. Accordingly, it should be understood that the invention is not limited in its application to the details of construction and the arrangement of components set forth in the descriptions or illustrations provided herein. Additionally, it should be understood that the terminology used herein is for the purpose of description and should not be regarded as limiting.

Figure 2:
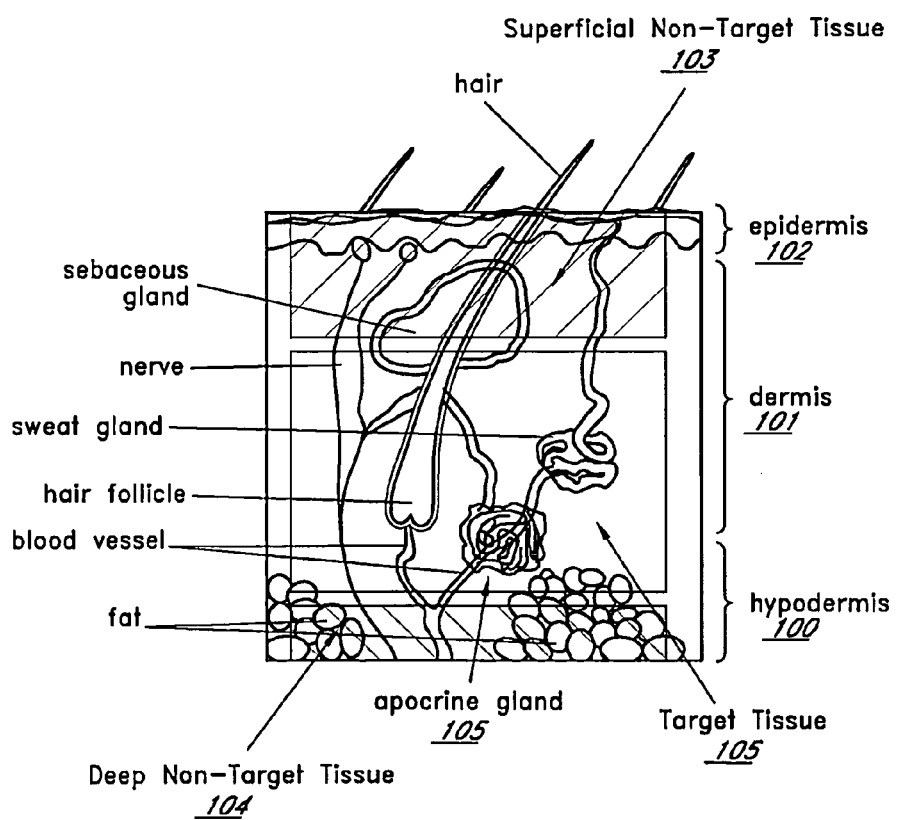
FIG. 2 shows a cross-sectional view of a target tissue having a zone of thermal treatment according to one embodiment.

FIG. 2 shows a cross-sectional view of the skin, its three primary layers and internal structures. In one embodiment, it is desirable to concentrate the treatment within the region of dermal 101 and subcutaneous tissue 100 (hypodermis) in which the eccrine and apocrine glands reside (e.g., "target tissue" 105) while doing minimal damage to the tissue above the sweat glands in the epidermis 102 and dermis 101 (e.g., "superficial non-target tissue" 103) and fat cells and other structures within the subcutaneous layer 100 (e.g., "deep non-target tissue" 104). Depending on the area of the body, the target tissue 105 region may begin anywhere from about 0.5 mm to about 4 mm beneath the skin's surface and end anywhere from about 1 mm to about 10 mm beneath the skin's surface. Depending on the area of the body, the superficial non-target tissue 103 region may begin at the skin surface and end anywhere from about 0.5 mm to about 4 mm beneath the skin's surface. Depending on the area of the body, the deep non-target tissue region 104 may begin anywhere from about 1 mm to about 10 mm beneath the skin's surface.

In the case of the axillae (underarm), the target tissue region may begin anywhere from about 1 mm to about 3 mm beneath the skin's surface and end anywhere from about 3 mm to about 8 mm beneath the skin's surface. Therefore, a treatment that concentrates energy from about 1 mm to 8 mm beneath the skin's surface in the axillae would be beneficial in treating axillary sweating.

For the purposes of this specification, eccrine glands, apoeccrine glands, and apocrine glands may be separately or collectively referred to as sweat glands or target structures. Similarly, the terms treatment, treatment effect, treating area/region may relate to the treatment of the target tissue and/or any target structures residing therein for the purpose of temporarily or permanently reducing or halting sweating, wherein the treatment itself may impact the target tissue and/or target structures in one or more of the following ways: modification, deactivation, disablement, denervation, damage, electroporation, apoptosis, necrosis, coagulation, ablation and destruction.

It should be noted that although the methods and apparatuses discussed herein are directed to the reduction of sweat production in sweat glands, the disclosed methods and apparatuses can be modified, and may be used for treating various kinds of target tissue and non-target tissue regions within the skin. For example, it is believed that the treatments disclosed herein can be used to, in certain embodiments, (1) tighten skin, reduce wrinkles and contour the skin by treating collagen, induce collagen formation and/or shrink collagen, (2) treat acne by targeting sebaceous glands within the dermis layer of the skin, (3) stimulate or retard hair growth, or temporarily or permanently remove hair by treating hair follicles and/or (4) treat cellulite for the purposes of weight loss and/or body sculpting.

Specific Embodiments

A. Energy Transfer Treatment

One approach for reducing sweat production includes thermally treating target tissue by either delivering energy to or extracting energy from the target tissue. A system can be configured to include a processor, an energy generator connected to the processor, and a device operatively coupled to the generator. The device can further include an energy delivery applicator or energy delivery element for delivering energy to the target tissue. In the illustrated embodiment, a cable electrically connects the device to an energy generator. In other embodiments, the processor, the device, and/or the energy generator can be connected wirelessly via, for example, radio frequency signals.

For purposes of this specification, the terms "electrode", "antenna", "energy", "energy element", "energy delivery element", "energy delivery applicator" or "energy source" individually and collectively encompass, but are not limited to, the use of one or more types of energy transfer modalities, including electromagnetic, x-ray, radiofrequency (RF), DC current, AC current, microwave, ultrasound (including high intensity focused ultrasound (HIFU)), radiation, near infrared, infrared, light/laser, cooling and cryotherapy, adapted and applied in ranges, intensities and/or quantities sufficient to treat, directly or indirectly (e.g., heating an intermediary substance) the target skin tissue via thermally or by other means. It should be noted that although one specific modality may be disclosed in a particular embodiment, the embodiment can be adapted to accommodate other forms of energy transfer. Even if a mechanism of energy transfer differs significantly from that disclosed in an illustrated embodiment, it should be understood that such mechanism can be employed by this embodiment. For example, the energy generator in one embodiment can generate an electric signal having a desired frequency, amplitude, and power level, and the cable can transmit the generated signal to the device, which comprises an electrode. In this embodiment, the processor is in communication with the energy generator to control the power output of the energy generator for providing the desired amount of energy to heat the target tissue. Alternatively, in an embodiment where the device comprises a Peltier electrode, the energy generator can supply the device with voltage to thermoelectrically cool the target tissue.

In embodiments relating to the delivery of thermal energy, in one embodiment it would be desirable to reach a temperature of at least about 50 degrees C. in the target tissue and/or target structures therein to achieve a treatment effect. For example, it is believed that delivering thermal energy sufficient to heat the target tissue to about 60 degrees C. would likely result in thermal ablation of the target tissue. In embodiments relating to cooling the target tissue, it is believed that cooling the target tissue from about 0 degrees C. to −40 degrees C. would likely result in a treatment effect to the target tissue.

Microwave Energy Delivery Device

Figure 3:
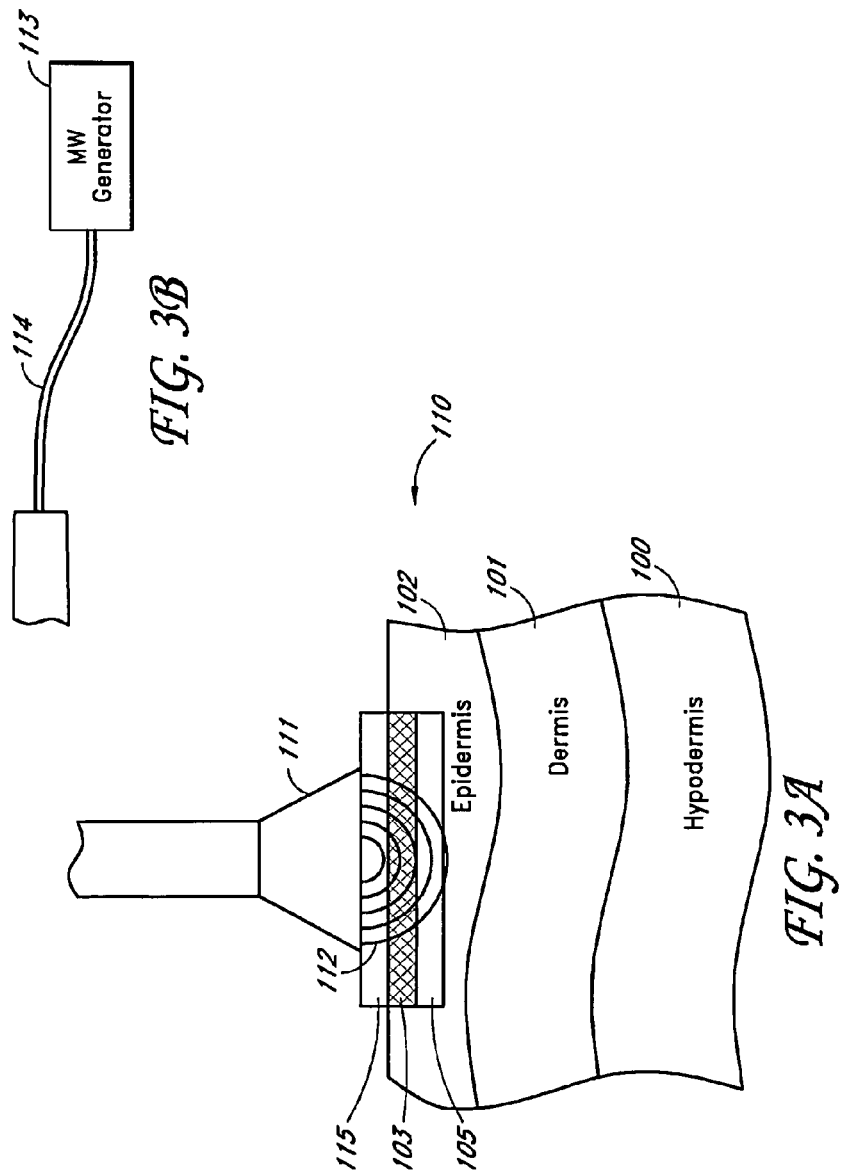
FIG. 3 shows a device having an energy applicator according to one embodiment.

The system illustrated in FIG. 3 shows a device 110 having an energy applicator 111 for non-invasively delivering microwave energy 112 to the target tissue layer 105 and a microwave generator 113 for supplying the applicator 111 with microwave energy 112. In this embodiment, the energy applicator 111 comprises one or more antennas for delivering microwave energy 112 to the target tissue 105. The antennas would be configured, when the device 110 is placed against or near the patient's skin, to heat and treat the target tissue 105 and target structures within the target tissue 105. The treated tissue could either be left in place to be resorbed by the body's immune system and wound healing response, or could be extracted using any number of minimally invasive techniques. As illustrated, the antenna may also comprise a horn shape, as described below, to provide a directional component to the energy field. In one embodiment, the energy generator 113 is remotely located from the energy applicator 111, wherein the generator 113 can be either stationary or mobile. Alternatively, the applicator 111 and generator 113 can be coupled such that they comprise a portable unit. Still alternatively, the applicator 111 and generator 113 can be combined into a single unit.

Microwave energy is absorbed by the tissue in a process called dielectric heating. Molecules in the tissue, such as water molecules, are electric dipoles, wherein they have a positive charge at one end and a negative charge at the other.

As the microwave energy induces an alternating electric field, the dipoles rotate in an attempt to align themselves with the field. This molecular rotation generates heat as the molecules hit one another and cause additional motion. The heating is particularly efficient with liquid water molecules, which have a relatively high dipole moment.

The delivery of energy to the target tissue can be facilitated by antenna designs that incorporate a dielectric element. Unlike other forms of electrical energy delivery, such as radiofrequency, where energy is typically transmitted through direct electrical contact between a metal conductor and body tissue, microwave energy can be delivered across a dielectric material. A dielectric element will not block the microwave energy from radiating to adjacent tissue, but it may help optimize the delivery of energy to the target tissue over the course of the treatment. Since the dielectric heating properties and thermal conductivity of skin tissue change over the course of the treatment (e.g., as temperature rises) due to loss of moisture, a dielectric that is properly matched to the antenna design can maintain the delivery of energy to the target tissue.

The dielectric's impact on the antenna's energy delivery properties will decrease the further it is from the antenna. Therefore, to optimize energy delivery to target tissue over the course of the treatment, in one embodiment, it may be desirable to place the dielectric directly next to the antenna rather than locating it remote from the antenna. Therefore, the antenna design could be optimized by incorporating a covering comprising a dielectric (e.g., ceramic, PTFE, polyimid, etc.) with a dielectric constant that's matched to the heating requirements of the treatment. The dielectric may be incorporated into the antenna or be a separate component of the energy delivery device or system. Further details regarding antenna designs are discussed below.

Figure 4:
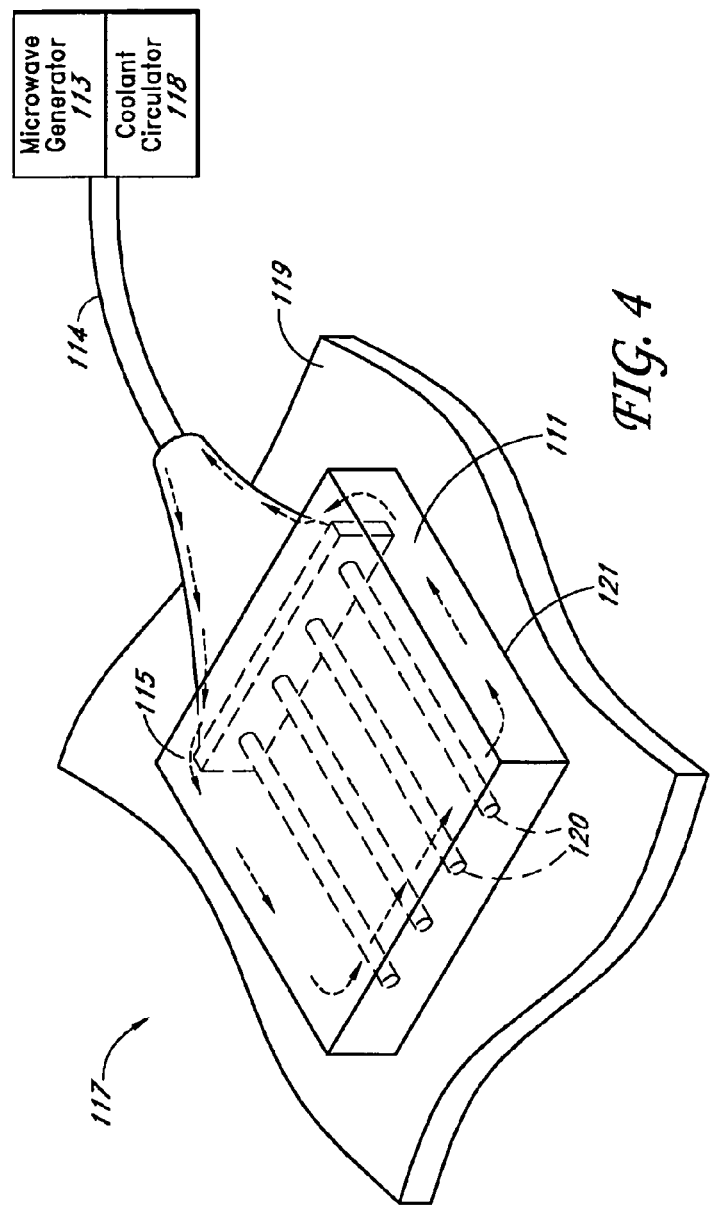
FIG. 4 shows an isometric view of a non-invasive energy delivery device comprising multiple microwave antennas electrically connected to a microwave generator according to one embodiment.

FIG. 4 is an isometric view depicting a non-invasive energy delivery device 117 comprising multiple microwave antennas 120 electrically connected to a microwave generator 113. In one embodiment, the antennas 120 are contained in a substantially planar applicator plate 121 sized for application against a target area of a patient's skin 119. In one embodiment, the device 117, and the applicator plate 121 therein, can be sized and configured to substantially match the area of tissue being treated. For example, in treatments relating to the reduction of axillary sweating, the device 117 can be configured to cover substantially all of the axillae region of the patient. Alternatively, the device 117 can be configured to cover at least a portion of the axilla. Additionally, the applicator plate 121 may be flexible to help the device 117 conform to the contours of the patient's skin 119.

Figure 5:
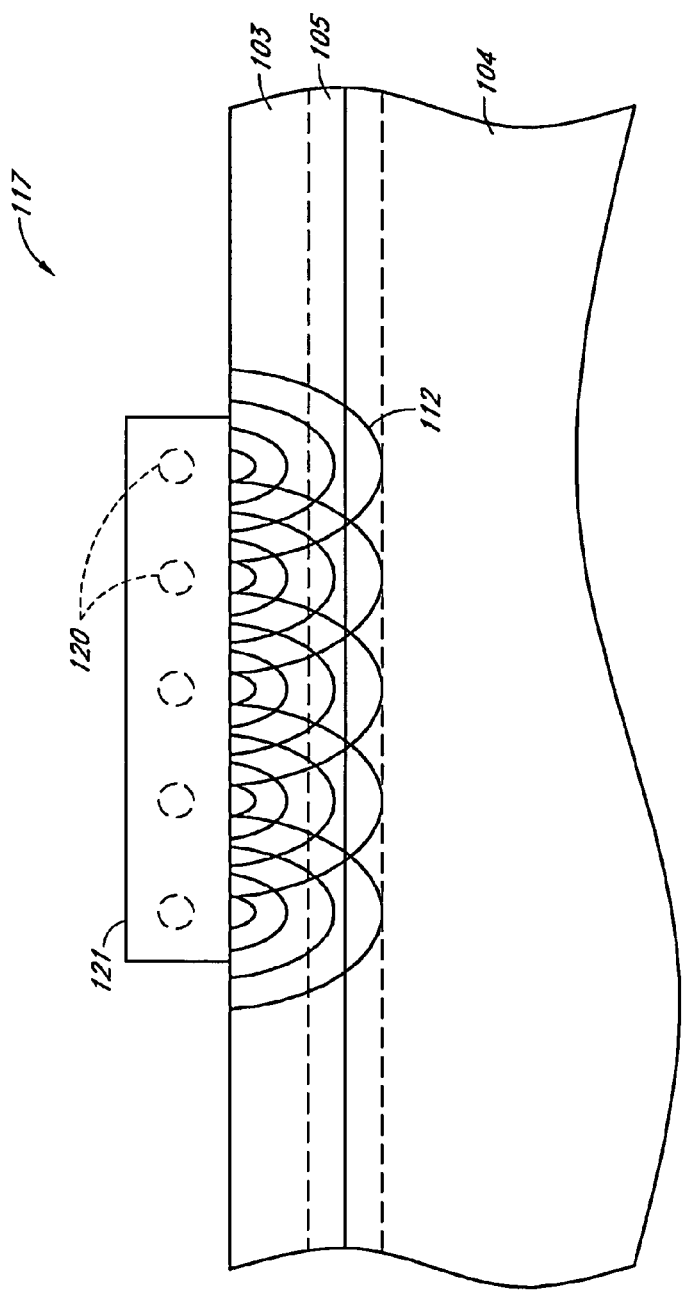
FIG. 5 shows a cross-sectional side view of the non-invasive energy delivery device of FIG. 4 delivering energy into the skin.

FIG. 5 is a cross-sectional side view of the same device of FIG. 4 showing the delivery of energy 112 into the skin. In such multi-antenna embodiments, it may be useful to orient the antennas 120 along the same plane in the same longitudinal direction to deliver energy 112 in a planar fashion. As shown in FIGS. 4 and 5, four or five microwave antennas 120 are positioned parallel to each other. In other embodiments, fewer or greater microwave antennas 120 may be provided, for example, one, two, three, five, six, seven, eight, nine, ten or more. With this planar configuration, energy can be delivered to a larger area of tissue in one treatment and in a more consistent fashion.

As discussed later in this specification, thermal protective measures can be employed in conjunction with thermal treatments. As shown in FIGS. 4 and 5, the applicator plate 121 containing the antennas 120 may be connected by a conduit 114 to the microwave generator 113, with cooling fluid passing through the conduit 114 to and from the applicator plate 121 from a coolant circulator 118. The cooling fluid creates a protected zone in the epidermis 103 of the patient, so that that target tissue 105 below the protected zone is treated.

The amount of energy 112 delivered to the target tissue 105 and consequent extent of treatment effect can be adjusted based on the number of antennas 120, their specific configuration and the power delivered to each antenna. In one embodiment, a microwave generator 113 with a microwave energy 112 output frequency ranging from 300 MHz to 20 GHz is suitable for feeding the energy delivery device 117 with power. In another embodiment, a microwave signal of anywhere from about 915 MHz to about 2450 MHz would be preferential for yielding a treatment effect on tissue. Alternatively, a signal having a frequency ranging from about 2.5 GHz to about 10 GHz may also be preferential. Additionally, solid state, traveling wave tube and/or magnetron components can optionally be used to facilitate the delivery of microwave energy 112.

Figure 6B:
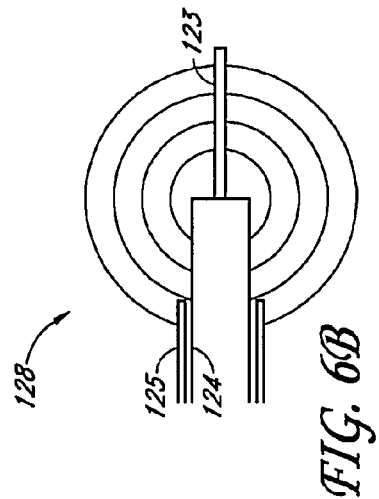
FIG. 6B shows a dipole antenna according to one embodiment.
Figure 6D:
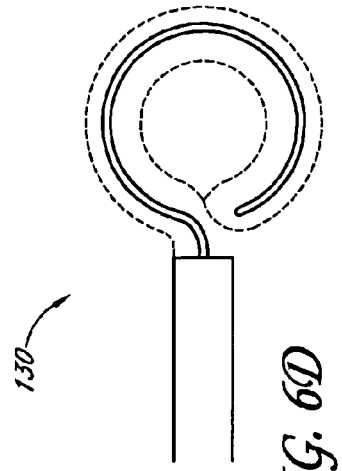
FIG. 6D shows a loop antenna according to one embodiment.
Figure 6A:
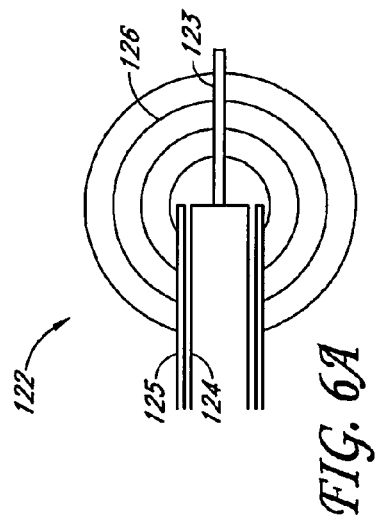
FIG. 6A shows a monopole antenna according to one embodiment.
Figure 6C:
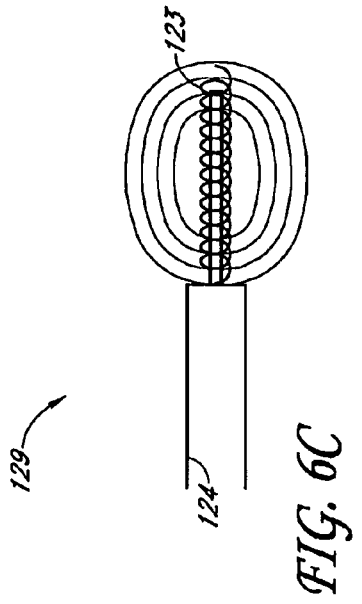
FIG. 6C shows a helical antenna according to one embodiment.
Figure 6E:
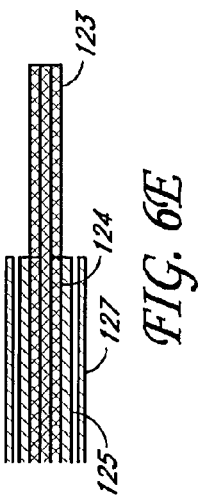
FIG. 6E shows a monopole antenna with a conductive shield or sleeve according to one embodiment.

With respect to antenna design, FIGS. 6A to 6G illustrate several possible variations that can be implemented to achieve the energy delivery function disclosed herein. In each design, the antenna comprises the distal end of a coaxial cable feedline through which electrical energy is transferred from an energy generator. The coaxial cable further comprises an inner conductor shaft 124 and outer conductor 125. FIG. 6A shows one embodiment of a monopole antenna 122. As shown in FIG. 6E, the antenna may be shielded or choked by a metal 127 to limit the electromagnetic field propagated by the antenna. In such monopolar configurations, an inner conductor element 123 extends from the inner conductor shaft 124 and beyond the outer conductor 125 such that the electromagnetic field propagated by the antenna originates from only the inner conductor element 123. In dipole antenna 128 configurations, as illustrated in FIG. 6B, the outer conductor 125 is exposed in such a manner that an electromagnetic-field is created between the inner conductor element 123 and outer conductor 125.

Figure 6F:
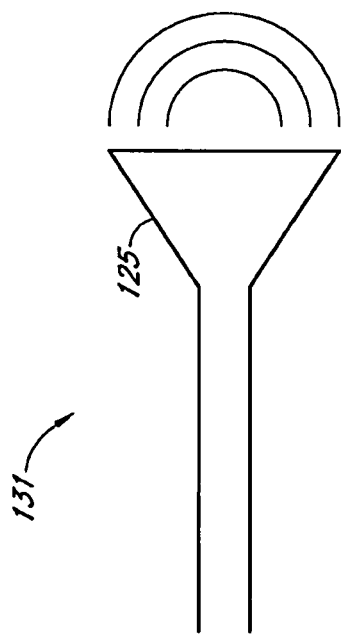
FIG. 6F shows an antenna having a shaped outer conductor according to one embodiment.
Figure 6G:
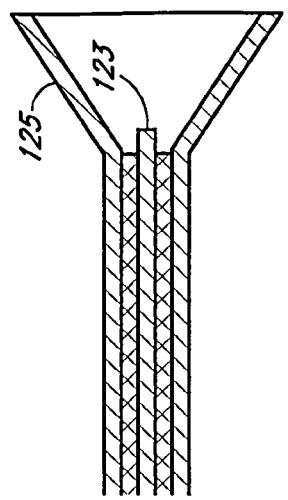
FIG. 6G shows an antenna having a shaped outer conductor according to a second embodiment.

Depending on the performance desired of the antenna, the antenna may optionally comprise a helical antenna 129 (FIG. 6C), loop antenna 130 (FIG. 6D) or horn antenna 131 (FIGS. 6F and 6G). These alternative antenna configurations provide geometric radiating patterns. For example, as illustrated in FIG. 6F, the outer conductor 125 may comprise a shaped element, such as a horn shape, to provide a directional component to the field created between the inner conductor element 123 and outer conductor 125. Optionally, the outer conductor element 125 and/or inner conductor element 123 may be bordered by, coupled to or coated by a dielectric element to optimize the energy delivery capabilities of the antenna.

In another embodiment relating to energy delivery to target tissue, the energy applicator comprises an antenna connected to a coaxial cable that is coupled to a microwave power source. As illustrated in FIG. 7A, the antenna 132 further comprises an inner conductor disposed within the coaxial cable 133, wherein an inner conductor element 123 extends beyond the distal end of the coaxial cable 133 to form a coiled conductor element. The coiled conductor element provides a relatively flat structure which can be aligned with the skin surface to deliver an even amount of energy to a plane of target tissue. The applicator may optionally further comprise at its distal end a thin shield comprised of a polymer or ceramic. FIGS. 7B and 7C illustrate additional embodiments of the coiled antenna configuration, wherein the coiled conductor element may comprise either the coaxial cable 133 or just the inner conductor 123.

Note that FIG. 7A shows the use of cooling fluid flowing through a coaxial antenna system 132. This antenna embodiment, or any other antenna configuration previously shown, for example FIG. 6E, can be configured to not only cool the skin, but also to create an area of lower pressure inside the device chamber than in the ambient surroundings. This area of lower pressure or suction within the device will help (1) adhere the device to the skin, bringing the target tissue into closer apposition to the antenna, and (2) reduce blood flow in the target tissue, thereby enabling more efficient heating of the tissue.

Additionally, suction may help to control pain by triggering stretch and pressure receptors in the skin, thereby blocking pain signals via the gate control theory of pain management. The gate control theory holds that an overabundance of nerve signals arriving at the dorsal root ganglion of the spinal cord will overwhelm the system, and mask or block the transmission of pain receptor signals to the brain. This mechanism of pain management is exploited by implantable electrical pain controls units, TENS systems, the Optilase system and others.

Since microwave heating is particularly efficient when water molecules are present in tissue, it may be desirable to have relatively high water content or molecule density at the target tissue or within the target structures. This high water content would result in greater microwave energy absorption and consequent heating at the point of treatment. Moreover, this phenomenon will allow the selective heating of target tissue, thereby minimizing the impact to non-target tissue.

Figure 8:
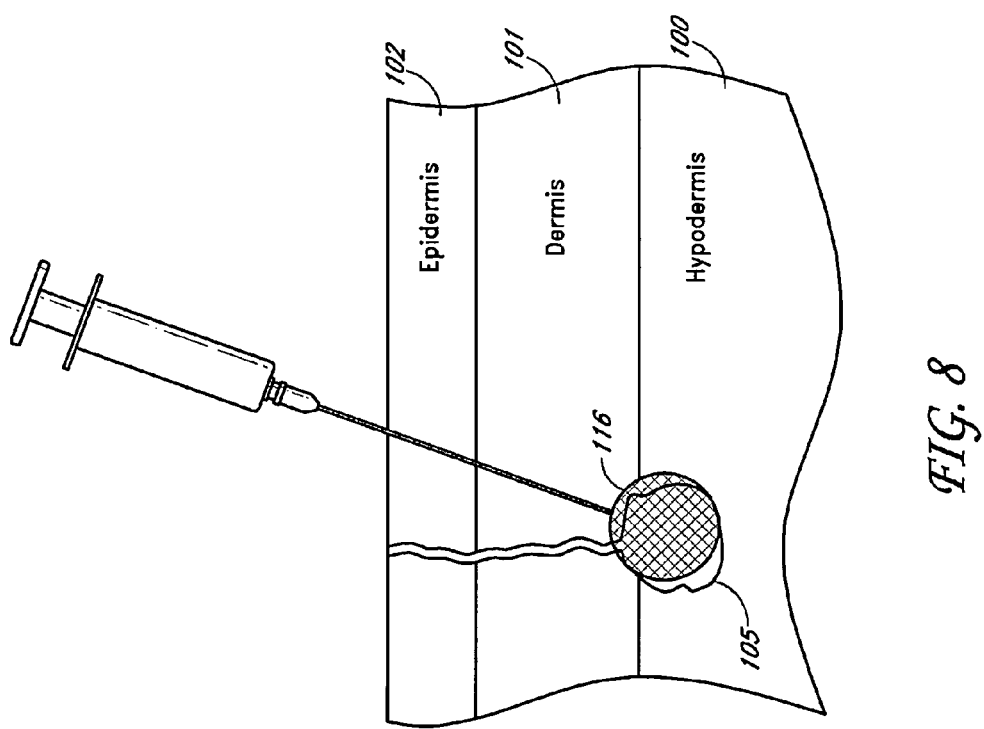
FIG. 8 shows a needle injecting fluid near the base of a sweat gland and target tissue according to one embodiment.
Figure 9A:
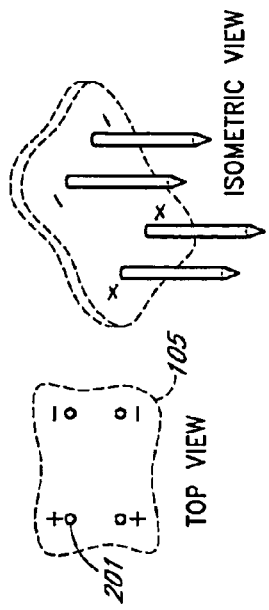
FIG. 9 shows a number of possible configurations of bipolar electrodes with respect to a desired treatment zone.
Figure 9B:
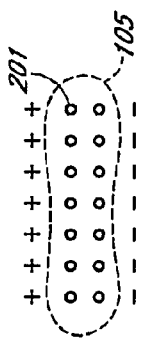
Figure 9C:
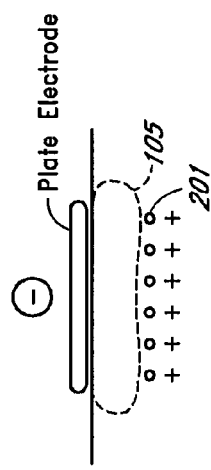
Figure 9D:
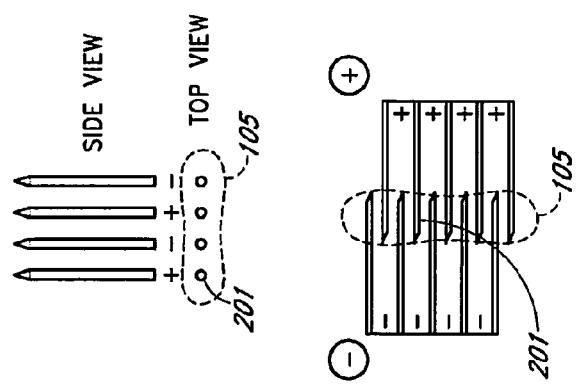
Figure 9E:
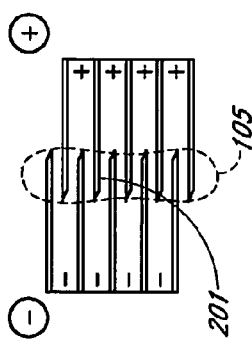
Figure 9F:
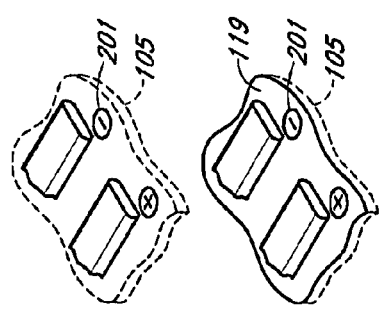

There are numerous ways in which water content in the target tissue can be achieved. For example, injecting a bolus of fluid (e.g., water, saline, etc.) into the target tissue or target structures would render such areas more susceptible to microwave treatment. FIG. 8 shows one embodiment of the injection of fluid 116 to near the base of a sweat gland and target tissue 105. In the case of target sweat glands, the patient can be induced to sweat in the area of treatment (such as by raising the ambient temperature or the temperature in the target area) in order to achieve higher water content in the target structures. In any of these cases, the water dense sweat glands can be plugged to prevent any of the water/sweat from escaping through the sweat ducts. Sealing the gland ducts can be achieved by using aluminum ion based topical products such as antiperspirants or any type of biocompatible polymer coating.

Further non-limiting examples of embodiments and components of embodiments of microwave systems, devices, and methods that can be utilized with those described herein are described, for example, in FIGS. 3-9 and 20-26 and pp. 11-20 and 34-48 of U.S. Provisional App. No. 61/013,274 previously incorporated by reference in its entirety, as well as FIGS. 1-25 and pp. 9-18 and pp. 56-69 of U.S. Provisional App. No. 61/045,937, also previously incorporated by reference in its entirety. Furthermore, embodiments and components of embodiments described herein as well as, for example, those discussed in the previous sentence can be used to generate tissue profiles as illustrated in FIGS. 26-51 and described in pp. 18-39 of U.S. Provisional App. No. 61/045, 937, previously incorporated by reference in its entirety.

RF Energy Delivery Device

Radiofrequency (RF) energy is another mode of electromagnetic energy delivery that can be used to treat the target tissue. In one embodiment, a device comprising at least one electrode for delivering an electric field therapy is operatively connected to an RF generator for delivering RF energy via the electrode to target tissue. The energy delivery might be continuous or pulsed, thermal or non-thermal. For example, a continuous or pulsed electric field delivered from the electrode can heat the target tissue to a temperature necessary to achieve a desired treatment effect. Alternatively, the delivered energy can heat and/or ablate the nerves, neuromuscular junctions and/or neuroglandular junctions associated with the target structures in order to temporarily or permanently denervate the target structures. A pulsed electric field can also induce electroporation in these neural structures or the target structures themselves to achieve a treatment effect.

The electrode(s) can be individual electrodes that are electrically independent of each other, a segmented electrode with commonly connected contacts, or a continuous electrode. A segmented electrode can, for example, be formed by providing an insulated tube with slots into which the electrode is placed, or by electrically connecting a series of individual electrodes. Individual electrodes or groups of electrodes can be configured to provide a bipolar signal. The electrodes can be dynamically assignable or hardwired to facilitate monopolar and/or bipolar energy delivery between any of the electrodes and/or between any of the electrodes and one or more external ground pads. For example, an array of electrodes can be configured such that both a monopolar energy field and a bipolar energy field can be selectively, sequentially, and/or simultaneously delivered. A ground pad can, for example, be attached externally to the patient's skin (e.g., to the patient's leg).

There are a wide variety of configurations for the active electrodes in either monopolar or bipolar configurations. They may be flat or curved to promote uniform contact over the electrode surface. The contact area of the active electrodes may be round (e.g., circular, elliptical) or rectilinear (e.g., square, rectangular, polygonal)—virtually any shape is possible. The shape may be chosen, for example, to suit the tissue to be treated or to allow optimal coverage for repeated activations. For example, in one embodiment, an electrode with a hexagonally shaped contact area may offer the advantage of providing complete coverage when treating irregular areas through multiple activations. It will be appreciated that similar shapes may be used for the applicator plate in the microwave embodiments discussed above. The number of electrodes may be varied to allow patterned delivery of energy to tissue; at least one active electrode for monopolar and at least two active electrodes for bipolar are desired. Multiple electrodes can be configured in many different patterns such as circular patterns, radial patterns, rectangular arrays, or in approximation of any of the shapes described in this specification. FIGS. 9A-F show a number of possible configurations of bipolar electrodes 201 with respect to a desired treatment zone 105, including top and side views of alternating configuration electrodes shown in FIG. 9A, top and isometric views of alternating plane configuration electrodes shown in FIG. 9B, trident configuration electrodes shown in FIG. 9C, sandwich configuration electrodes shown in FIG. 9D, flat plate configuration electrodes shown in FIG. 9E, and roof with plate configuration electrodes shown in FIG. 9F.

The depth of energy penetration, achieved tissue temperature and consequent extent of tissue effect caused by the RF delivery device will depend on a number of factors, including, the power delivered by the RF generator, the spacing of the one or more electrodes, the size of the electrodes, the orientation of the electrodes, the amount of contact the electrodes have with the target tissue and the properties of the tissue itself.

The electrical generator may be a conventional power supply that operates at a frequency in one embodiment in the range from about 200 KHz to about 1.25 MHz, more preferably about 400 KHz to about 1.0 MHz, with a conventional sinusoidal or non-sinusoidal wave form. Such power supplies are available from many commercial suppliers, such as Valleylab, Aspen, and Bovie. Depending on the desired treatment effect, it may be necessary for the electrical generator to operate at relatively low and relatively high voltages and power levels. For example, generator operability may include a power anywhere from about ½ W to about 100 W. In some embodiments, to achieve the desired treatment effect it may be desirable to continuously deliver energy for periods as short as ¼ second or as long as 300 seconds.

For embodiments that require the delivery of a pulsed electric field (PEF), PEF parameters may include, but are not limited to, voltage, field strength, pulse width, pulse duration, the shape of the pulse, the number of pulses and/or the interval between pulses (e.g., duty cycle), etc. in any range and combination. Suitable pulse widths include, for example, widths of at least 10 seconds and up to about 500 milliseconds. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, and combinations thereof. Suitable numbers of pulses include, for example, at least one pulse. Suitable pulse intervals include, for example, intervals less than about 10 seconds. These parameters are provided for the sake of illustration and should in no way be considered limiting.

Figure 10:
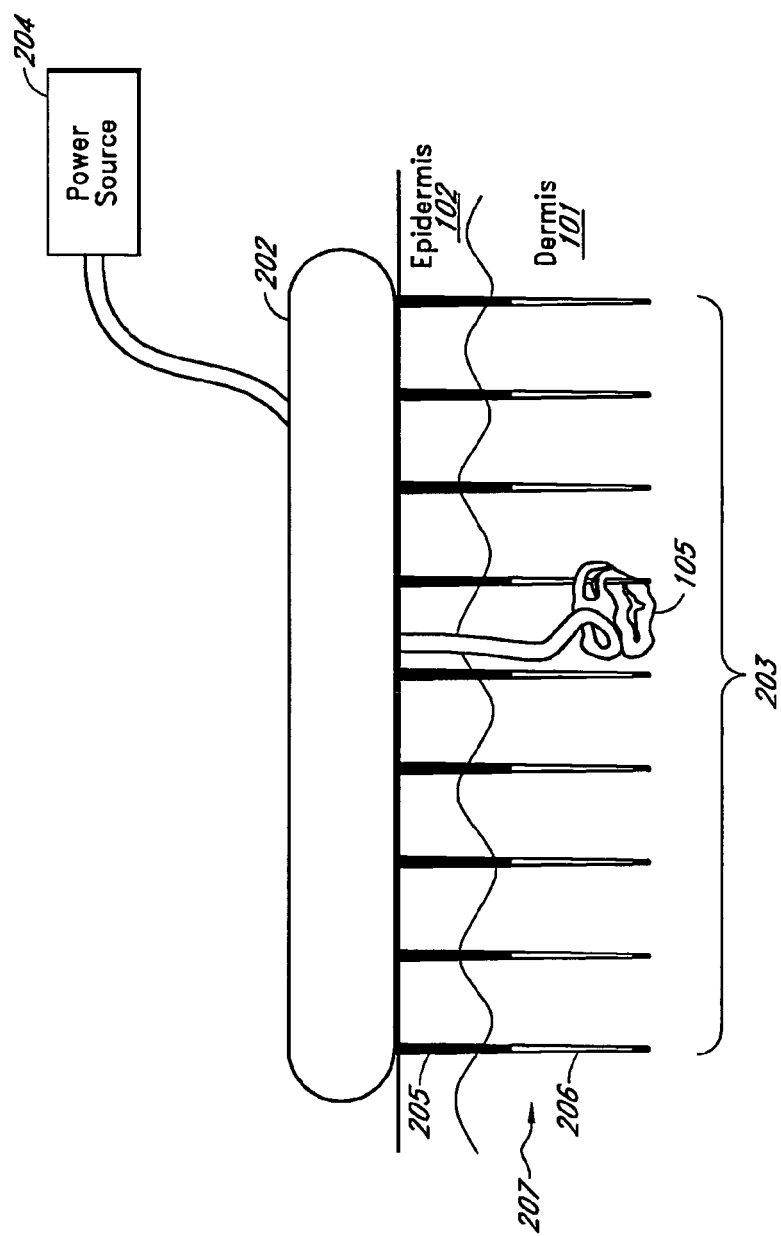
FIG. 10 shows an RF delivery device having one or more energy delivery elements comprising electrode-tip needles, microneedles or stylets for insertion into the skin according to one embodiment.

In the embodiment illustrated in FIG. 10, the RF delivery device 202 can take the form of one or more energy delivery elements comprising electrode-tip needles, micro-needles, or stylets for insertion into or across the epidermal layer 102 of the skin. Alternatively, the entire energy delivery element can comprise an electrode that is optionally insulated at points along the element where energy delivery is undesirable (e.g., non-target tissue). This minimally-invasive insertion approach allows for a more localized treatment of target tissue 105 such that damage to non-target tissue is minimized. Following needle 203 insertion to a reasonable depth, which would preferably be the depth of target tissue, but may be more or less deep, the operator can direct the RF generator 204 to deliver an electric field to the electrode for subsequent delivery to the target tissue 105. The electric field from the electrode will resistively heat the target tissue 105. In instances where the target tissue 105 is outside the electric field, and therefore outside the zone of resistive heating, the target tissue can be heated conductively by adjacent tissue that is resistively heated by the electrode's electric field.

Another potential benefit of having the interstitial needle insulated along its length is avoiding unnecessary heating of non-target tissue via thermal conduction from the needle itself. As the electrode resistively heats the surrounding tissue during RF treatment, the electrode also absorbs heat from the tissue. Heat absorbed by the electrode may then be conducted to the rest of the needle where it may be undesirably passed to surrounding, non-target tissue. A needle 203 configured with an insulated shaft 205 as illustrated in FIG. 10 can prevent the conduction of heat to non-target tissue alongside the needle shaft 205. In this embodiment, a proximal portion of the needle is insulated to the depth of the non-target tissue while the electrode 206 at the distal portion of the needle 203 is exposed to treat the target tissue 105. Alternatively, the electrode 206 tip can be partially insulated in such a fashion as to provide a directional component to the delivery of RF energy. This directional bias may advantageously provide a means for minimizing energy delivery and consequent thermal damage to non-target tissue.

Protective treatments may be used with certain embodiments (not shown). In the case of thermal treatments such as by RF energy or microwave energy, a cooling system, cooling element or cooling component may be provided such as described elsewhere in this specification. In one embodiment, the cooling element may be used in combination with an insulating element, while in another embodiment, the cooling element may be used as an alternative to an insulating element. When a cryogenic treatment is provided (as described further below), a protective treatment may include heating a portion of an energy delivery device.

Depending on the target tissue 105 region being treated, the needle electrodes 206 of FIG. 10 may have a length of about, for example, 1 to 10 mm, and preferably no greater than about 8 mm. Even more preferably, the needle electrodes 206 may have a length of about 2 to 5 mm in some embodiments. It will be appreciated that the length of the needles 203 may be optimized to be inserted to a depth where the target tissue 105 is located.

Figure 11:
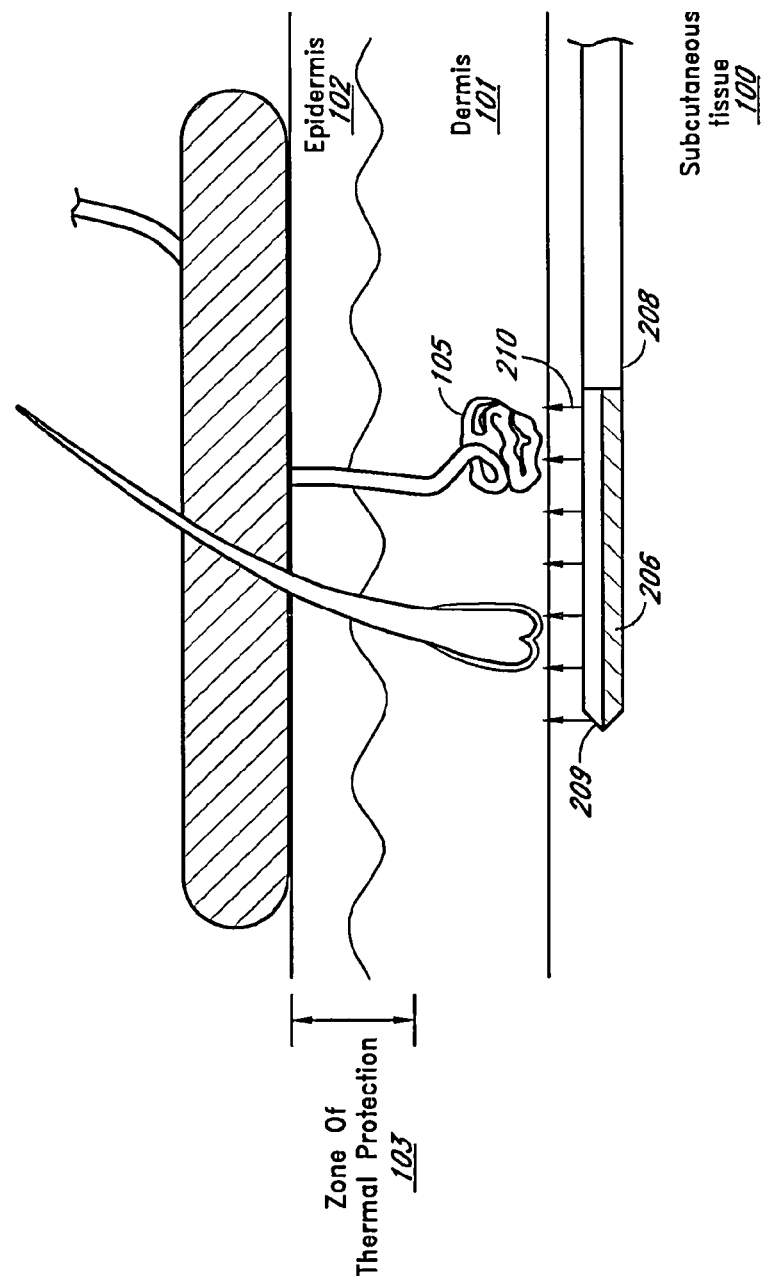
FIG. 11 shows an energy delivery device comprising a needle configured for percutaneous insertion according to one embodiment.

In the embodiment illustrated in FIG. 11, the energy delivery device comprises a needle 208 configured for percutaneous insertion. The needle 208 further comprises a distal portion having one or more energy delivery elements 209 for delivering energy 210 to the target tissue 105. More specifically, this embodiment may comprise a needle 208 having one or more electrodes for treating the target tissue with RF energy 210. As mentioned above, a portion of the needle 208 can be insulated to provide a directional component to the energy delivery. This directional component can advantageously allow for a more controlled treatment, wherein less non-target tissue is damaged. In one embodiment, the needle 208 is insulated so that energy is delivered toward the epidermis 102 and away from subcutaneous 100 tissue. The electrode 206 provided on the needle 208 may have any suitable length to treat a single sweat gland or multiple sweat glands. Alternatively, multiple electrodes 206 can be placed on the needle 208 spaced apart for treating multiple sweat glands. To treat a larger area of target tissue 105, the needle 208 can optionally be configured to translate angularly or be "fanned" out parallel to the target tissue 105. For example, the energy delivery element 209 can be rotably coupled to the needle 208 so that it may translate parallel to the target tissue 105. As discussed with previous embodiments, a cooling source may be provided on the skin to protect the skin surface, epidermis 102 and parts of the dermis 101.

Cryogenic Therapy Device

Cryotherapy may present an opportunity to provide a treatment effect on target tissue. Since the collagen matrix of the skin is less sensitive to cold, it is possible to cool target structures without damaging non-target skin tissue comprising collagen. The embodiments depicted in FIGS. 10 and 11 can also be utilized to treat the target tissue via cryotherapy. In these embodiments, an interstitial element comprising one or more needles, stylets, catheters or probes can be configured with one or more passageways to deliver a cryogenic fluid to at least one thermally conductive element adjacent or near the target tissue to provide treatment to the target tissue. The system can be configured to have an adjacent or remotely located generator for supplying cryogenic fluid (e.g., liquid nitrogen, liquid helium, liquid argon, liquid carbon-dioxide, liquid nitrous oxide, liquid AZ-50, chilled anti-freeze, chilled alcohol, chilled saline, etc.). The generator should deliver cryogenic fluid to the device sufficient to reduce the temperature of the target tissue to between about 0 to −40 degrees Celsius. In some embodiments, a temperature of between about 0 to −10 degrees Celsius may be sufficient to induce necrosis in the target tissue although this may be above the freezing point of the target tissue, whereas a temperature less than about −10 degrees Celsius may be sufficient to freeze the target tissue.

To maintain constant cooling therapy, it may be desirable to circulate the cryogenic fluid through the interstitial portions of the device. For example, as illustrated in FIG. 12A, the device 211 is configured with an interstitial element 212 comprising at least two concentric tubes 213, 214. In this embodiment, cryogenic fluid can be delivered through the interstitial element 212 and to the thermally conductive element by the inner tube 213 and then circulated out of the interstitial element 212 through the outer tube 214. In this embodiment, the outer tube 214 itself can be a thermally conductive element. Alternatively, as illustrated in FIGS. 12B and 12C, the interstitial element 212 could be configured with a tubular coil 215 that resides either inside or outside of the element 212. The cryogenic fluid would be routed through the lumen of the coil 215 to provide a thermal treatment effect to the target tissue.

In other embodiments, the device may comprise a cryoballoon catheter, wherein the thermally conductive element comprises a balloon. In such balloon configurations a pressurized liquid such as nitrous oxide is routed through the interstitial element's passageway. When the liquid reaches the balloon it undergoes an endothermic phase change such that the liquid absorbs heat from the surrounding area to achieve a treatment effect on the target tissue.

Alternatively, an interstitial needle or probe can be used instead of a cryoballoon catheter to administer cryotherapy to target tissue. For example, FIG. 12D shows an interstitial element 212 comprising an inner tube 216 and outer tube 217. The inner tube 216 comprises an inner lumen 218 for liquid nitrous oxide to travel from a proximal portion 219 to a distal portion 220 of the tube. The inner tube 216 further comprises at least one port or nozzle 221 along the distal portion 220 of the tube for the liquid nitrous oxide to exit the inner tube 216. As the liquid nitrous oxide exits the port 221 at, preferably, high velocities, it undergoes an endothermic phase change, wherein the outer tube 217 is cooled by the nitrous oxide gas. As the gas absorbs energy from the outer tube 217, which comprises the thermal conductive element in this embodiment, and the surrounding target tissue, the gas then exits the interstitial element 212 through the annular space between the outer tube 217 and inner tube 216.

The approach disclosed in FIG. 12D allows for a more focused area of cryogenic treatment. The nitrous oxide gas exits the distal portion 220 of the inner tube 216 at its coldest temperature and then absorbs thermal energy from the distal portion 1242 of the outer tube 217. Following heat exchange with the distal portion 1242 of the outer tube 217, the gas then travels toward and out the proximal end 219 of the interstitial element 212. Therefore, the distal portion 1242 of interstitial element 212, the portion which is adjacent to the target tissue, is the coolest.

Various parameters of this cryogenic system can be adjusted to modulate the temperature of the gas and vary the rate and extent of thermal treatment. For example, the shape, size and number of nozzle/port openings may have bearing on the rate of conduction and convection. The size of the annular space between the outer and inner tubes of the interstitial element will also impact the heat transfer properties of the device. Additionally, the pressure of the nitrous oxide liquid will also contribute to the heat exchange capabilities of the treatment.

Figure 12F:
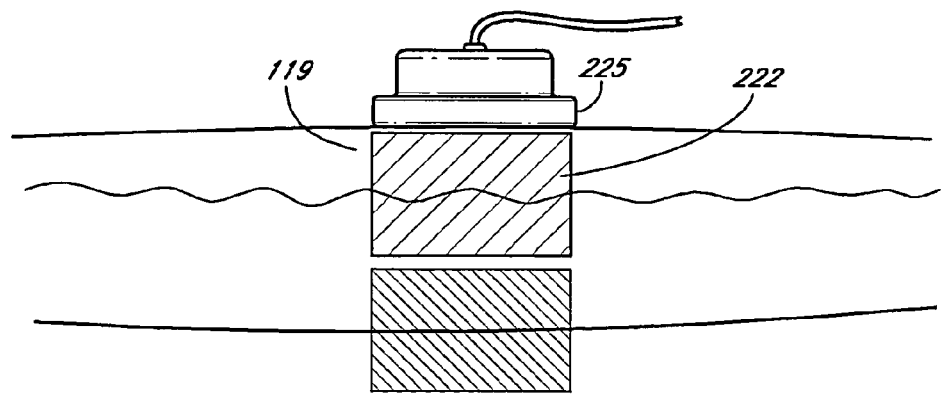
FIG. 12F shows a zone of protected non-target tissue between a cold source at the skin surface and the cryogenic treated region of target tissue according to one embodiment.

Cryotherapy may also be administered topically to treat target tissue below the surface of the skin. To minimize the risk of damage to the epidermis and other non-target tissue, it may be desirable to use cryoprotective agents in conjunction with non-invasive cryotherapy. As illustrated in FIG. 12E, cryoprotective agents 222 such as ethylene glycol, glycerol, erythritol or dimethylformamide can be applied topically or via injection to minimize the treatment effect to non-target tissue 103. Cryoprotective agents 222 can also be utilized in conjunction with percutaneous therapies utilizing the interstitial elements discussed above. As shown in FIG. 12F, the cryoprotective agents 222 can be used to create a zone of protected non-target tissue 223 between the cold source 225 at the skin surface 119 and the cryo-treated region 224 of target tissue.

Phototherapy

Another approach for treating target tissue comprises the use of phototherapy. In this approach, the unique optical characteristics of target structures are used to determine a spectral signature for each structure. Light energy can be delivered to the target tissue at a wavelength that is matched to the spectral signature of a particular structure to selectively heat and treat the structure through light absorption.

Phototherapy can also be implemented through coloring the target tissue or area surrounding the target tissue and then delivering light energy to heat the coloring. For example, a colored substance can be introduced into the target tissue and a light energy having a waveform that has a specific absorption for this color can be delivered from an internal or external source to treat the target tissue. The principal advantage of this approach is that the target tissue can be selectively colored so that the treatment can be localized to the target tissue with minimal impact to non-target tissue. Phototherapy can be performed using various types of light energy, including, but not limited to, laser, intense pulsed light ("IPL"), focused IP, infrared and near infrared. These various light energies can be implemented with any number of energy delivery elements, including, but not limited to, a laser, light emitting diode ("LED") or light bulb. Optionally, one or more filters can be used in conjunction with any of these energy delivery elements to remove unnecessary wavelengths, including those that would be absorbed by non-target tissue.

In one embodiment associated with phototherapy, a chromophore (i.e., colored molecule) is introduced into the target tissue. In the case where the target structures are the sweat glands, the chromophore can be introduced through the gland ducts via topical delivery, injected to the target tissue or ingested by the patient such that the coloring appears in the patient's sweat (i.e., chromohidrosis). For example, it is known that sulfur compounds in garlic are metabolized by the body to form allyl methyl sulfide (AMS), which is excreted from the body via the sweat. By binding a chromophore to the sulfur in garlic such that the chromophore is bound to AMS post-metabolization, the color can be delivered directly to the sweat glands. Following the appearance of color in the target tissue, an external source or energy delivery element (e.g., light emitting diode "LED") can deliver a light energy source, such as a laser or other light delivery system specifically matched to one or more chromophores to selectively treat the target tissue. This light energy can non-invasively travel down the sweat duct or transcend the layers of epidermis and dermis to reach the target tissue. Alternatively, an interstitial device utilizing fiber optics can deliver the light energy directly to the target tissue.

Figure 13:
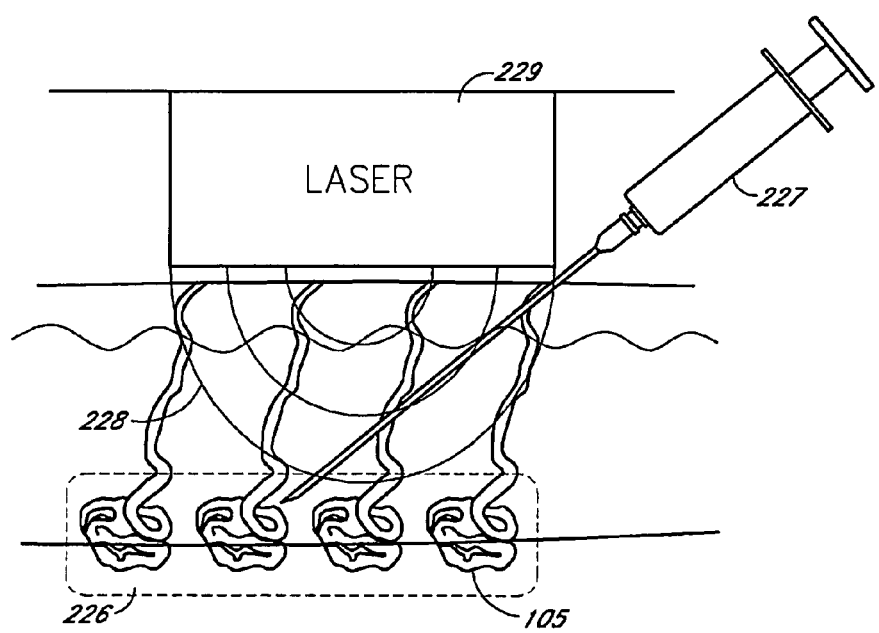
FIG. 13 shows a layer of colored bioresorbable microspheres deposited into or around target tissue according to one embodiment.

In another embodiment associated with this approach, a colored bioresorbable element can be introduced into or around the target tissue. For example, as illustrated in FIG. 13, a layer of colored bioresorbable microspheres 226 can be deposited into or around the target tissue 105. The microspheres 226 can be injected as part of a bio-inert solution, gel or other carrier with a syringe 227 into or around the target tissue 105. Once deposited in or around the target tissue 205, the colored microspheres 226 can be heated by laser light 228 from a laser 229 matched to their particular color, thereby conductively heating the target tissue 105 to yield a treatment effect. These microspheres 226 can be comprised of materials, such as polytetrafluoroethylene (PTFE), polymethyl methacrylate (PMMA) or calcium hydroxylapatite (CaHA), and colored to match laser wavelengths that would result in the most efficient heating of the microspheres 226, with the laser 229 having relatively little impact on the tissue in its path.

Figure 14:
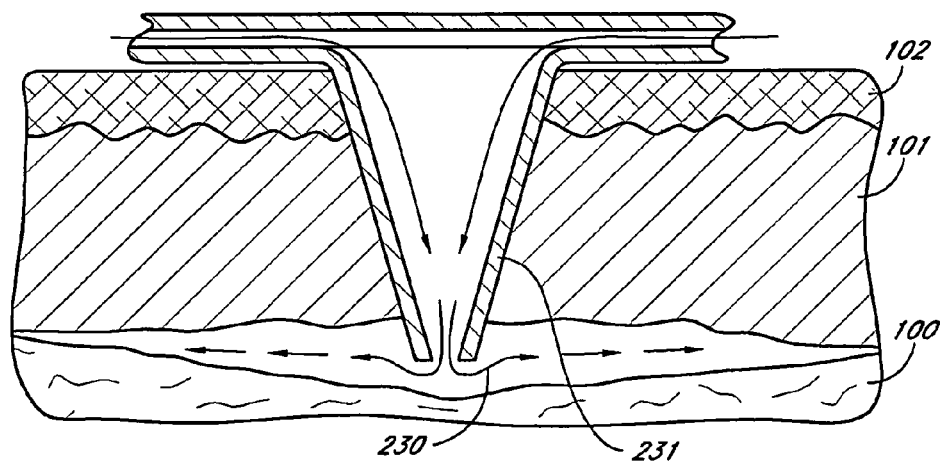
FIG. 14 shows a carrier solution being introduced by a hollow needle into a planar interface between the dermal layer and subcutaneous layer according to one embodiment.

In phototherapies involving the deposition of chromophores into or around the target tissue, delivering chromophores in the presence of a carrier solution may result in a wider and more even distribution of chromophore prior to treatment. A wider and more even distribution of chromophore may result in a wider and more consistent treatment effect. For example, chromophore may be suspended in a carrier solution of buffered or unbuffered saline prior to injection into the target tissue. As illustrated in FIG. 14, a carrier solution 230 is introduced using a hollow needle 231 into the planar interface between the dermal layer 101 and subcutaneous layer 100 to create a pathway for chromophore migration. Additionally, the carrier solution 230 may incorporate drugs for enhancing the distribution and/or effects of the chromophore or facilitating recovery following treatment.

In another embodiment associated with the phototherapy approach, a neurotoxin can be used as a vehicle to carry a colorant to the neuroglandular or neuromuscular junctions of the target tissue and/or target structures. It's commonly known that *Clostridium botulinum* neurotoxins, such as botulinum toxin type-A, can be administered to treat various neuromuscular and neuroglandular conditions by binding to cholinergic neurons at these junctions and blocking the release of acetylcholine in the synaptic vesicles of the neurons. Although the tissue at the junction is denervated by this blocking, this result is only temporary. By using the toxin to color the neural junctions of the target tissue and/or target structures, light energy can be delivered to thermally ablate these junctions and selectively denervate the target tissue/structure to achieve a longer lasting treatment.

In this approach, the toxin itself can be colored or alternatively, a chromophore chemically bound to the toxin may be used. Additionally, the light energy delivered to the target tissue will be specifically matched to the colorant to maximize the energy absorbed at the junctions.

There are seven serologically distinct types of botulinum toxin, designated A through G. The toxin is a two-chain polypeptide with a 100-kDa heavy chain ("heavy chain") joined by a disulphide bond to a 50-kDa light chain ("light chain"). The heavy chain is responsible for targeting and binding to the cholinergic neurons at and around the injection site and helping the light chain cross the neuron cell's membrane. The light chain is responsible for carrying the toxicity to the neuron. Although a potential molecular mechanism of toxin intoxication of botulinum toxin is discussed here, other toxins, for example, butyricum toxins, tetanus toxins, exotoxins, diphtheria toxins, cholera toxins, ricin, or variants thereof may have the same or substantially similar mechanisms.

In this approach it may be desirable to only use the heavy chain fragment of the toxin as the colorant's delivery vehicle. By isolating the heavy chain fragment and excluding the light chain fragment from the toxin molecule, the introduction of toxicity into the body will be avoided. Additionally, since an intact toxic molecule may provide a temporary treatment effect, presence of the light chain fragment may make it difficult to determine the success of the thermal treatment. Accordingly, coloring a heavy chain toxin fragment or binding a chromophore to a heavy chain toxin fragment may result in a more appealing treatment. In some embodiments, 100 to 200 units of botulinum toxin are administered to a patient to treat an axillary region. Other doses may also be administered depending on the desired clinical result.

In another embodiment, microneedle technology can be employed to facilitate the delivery of chromophores to the target tissue. For example, the microneedles can be hollow to facilitate the delivery of a colored substance (e.g., liquid or solid chromophore, colored microspheres, etc.) to the target tissue. Alternatively, the needles may be configured to deliver the chromophores only across the stratum corneum from where the chromophores can migrate to the target tissue via reverse iontophoresis. In an additional embodiment, reverse iontophoresis is used to drive the chromophores directly across the epidermis and into the deep dermis.

In another embodiment, as illustrated in FIGS. 15 and 15A, the needle tips 232 are comprised of at least one chromophore 233 and are configured to detach from the needle 234 when inserted into or alongside the target tissue. The needle tip 232 may be coated with a chromophore 233 or be comprised of a solid chromophore 233 and the needle shaft 235 may be solid or hollow. In embodiments employing the detachable, chromophore tipped microneedles 234, the microneedles 234 can optionally be configured to engage a tip deployment mechanism 237. A tip deployment mechanism 237, such as a single plunger or array of plungers, can be utilized to facilitate the detachment of the chromophore needle tip 232. For example, hollow-bodied needles 234 can be used to allow the deployment mechanism 237 access to the detachable chromophore tip 232. More specifically, the deployment mechanism 237 can be driven through the needle's lumen 238 to disengage the detachable tip 232. Alternatively, the deployment mechanism 237 can comprise a hydraulic element, such as pressurized air, to effect the detachment of the needle tip 232. Additionally or alternatively, the needle tip 232 and/or needle shaft 235 can be configured with a pre-established weakness to facilitate deployment. For example, as illustrated in FIGS. 15 and 15A, the needle tip 232 can be configured with a notch or groove 236 such that it breaks along the notch or groove 236 following insertion into or prior to retraction from the target tissue.

The needles 234 shown in FIGS. 15 and 15A may be joined in an array of needles, such as a linear or planar array. The needles 234 may have a length of about 2 to 8 mm, more preferably about 4 mm, with the length of the detachable tip 232 being matched to the depth of the target tissue. The deployment mechanism 237 such as a plunger or array of plungers may detach each needle separately, in a preferential sequence, or all at once.

In an alternate embodiment employing chromophore tipped microneedles, the microneedle shaft is comprised of a dissolvable material such that the microneedle shaft dissolves following the microneedle insertion into the skin, leaving the chromophore tip in the target tissue. For example, a microneedle array can be cast and cured with the distal tips comprising chromophores and the proximal shaft comprising a sucrose solution. Once the microneedle is inserted into the skin, the sucrose shaft will be broken down within the interstitial space of the skin tissue such that the chromophore tip is the only portion of the needle that remains in the skin. In this embodiment, it may be desirable to incorporate a flexible backing substrate into the cast microneedle array such that following insertion into the skin; the backing can be peeled off the microneedle leaving a portion of the needle shaft and chromophore tip within the skin.

Optionally, the hollow microneedles can be utilized as a pathway for delivery of light energy to the deposited colored substance from a source outside the body. Alternatively, the microneedles may comprise fiber optic material to facilitate the delivery of light to the color at the target tissue.

In the above embodiments providing for the delivery of color to the target tissue, various mechanisms can be employed to minimize the impact of any structures or color fragments left behind following treatment. In the case of certain colored liquids, gels and solids, the laser delivery can be set at an intensity and duration sufficient to ablate and vaporize part or all of the deposited material. In the case of a bioresorbable implant, such as microspheres, the implant may eventually be absorbed into the surrounding tissue so there is no adverse physiological or aesthetic impact resulting from the presence of the microspheres or color. Additionally or alternatively, any remaining color can be bleached by light at the treatment wavelength, or an alternate wavelength, such that it is no longer visible in the skin. Alternatively, the chromophore may not be bioresorbable, or bleachable, but rather the light energy may fracture the chromophore into particles small enough to be phagocytosed and cleared from the body by the immune system. This mechanism of action is well known in the area of tattoo removal, where, for instance, carbon black tattoo inks are fractured by laser light and cleared by the body.

Figure 16:
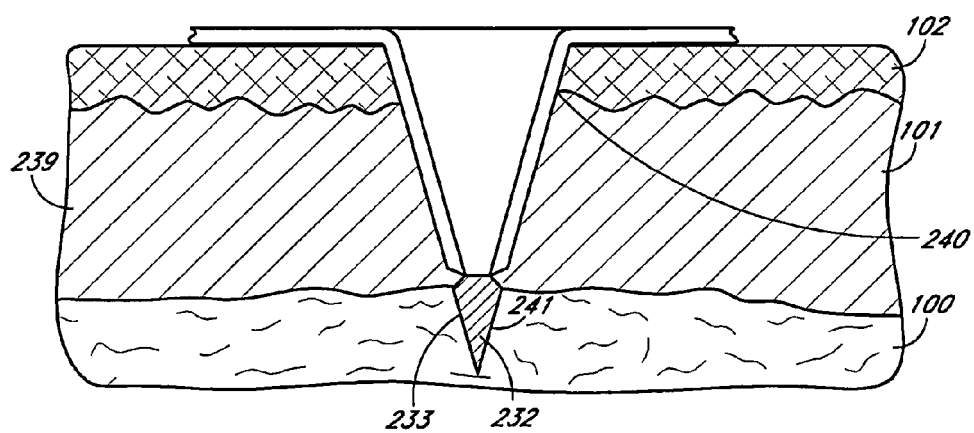
FIG. 16 shows a microneedle configuration having a non-detachable chromophore tip according to one embodiment.

In another embodiment incorporating chromophore-tipped microneedles, the chromophore tip is configured to be removed from the target tissue along with the needle. In this configuration the tip is not detachable from the needle shaft. This intact microneedle 239 configuration is illustrated in FIG. 16. The needle 239 may comprise a proximal portion 240 made of an optically clear material or an optically neutral chromophore (i.e., unable to absorb, block or otherwise be activated by the treatment wavelength) and a distal portion 241 made of a chromophore. As light energy is delivered across the proximal portion 240 of the needle and absorbed by the colored distal portion 241, the distal portion 241 begins to heat, thereby conductively heating and treating the surrounding target tissue. Alternatively, the proximal portion 240 of the needle 239 can be configured as a light pipe or lens to focus the light energy into the chromophore tip 232.

In embodiments utilizing non-detachable, chromophore-tipped microneedles, it may be desirable to incorporate an array of needles into an optically neutral backing system. This array comprising chromophore tips and optically neutral shafts, configured with a geometry and needle density to optimize the treatment to target tissue, can be permanently coupled to an optically neutral backing system to form a microneedle patch. Following the insertion of this patch into the patient's skin, light energy can be applied to the optically neutral backing such that this energy is delivered via the optically neutral shafts and absorbed by the chromophore tips of the needles. The absorbed energy will heat the chromophore tip and thereby treat the surrounding target tissue. The patch can be any size, shape and geometry necessary to match the treatment area. Optionally, the patch's backing may comprise a flexible material to allow the patch to conform to the patient's skin. The backing system may also comprise an optically neutral adhesive on the portion most proximate to the skin to minimize movement of the patch during treatment. The use of adhesive may provide significant benefit in avoiding targeting error of treatment or patient discomfort from needle motion.

In any of the above embodiments relating to microneedles or microneedle patches, it may be beneficial to incorporate a drug into the adhesive, backing, or proximal portion of the needle shaft to facilitate healing of non-target tissue. The needles or patch can optionally be left inserted into the patient's skin following treatment of the target tissue to serve as an integral bandage. These healing drugs may comprise steroids, non-steroidal analgesics or anti-inflammatory medications such as antibiotic cream. Alternatively, the needle may be fully or partially coated with a chemical substance, such as a sclerosing agent, to enhance treatment of the target tissue.

In embodiments incorporating a microneedle patch having optically neutral components, it may be desirable to configure the system to block the delivery of energy once a specific threshold is reached to prevent unnecessary damage to the target tissue and/or non-target tissue. For example, an optically neutral backing, adhesive and/or needle can be designed such that when a prescribed amount of energy is transmitted through the system, at least a portion of the component becomes optically opaque to the treatment wavelength, thereby preventing additional energy from reaching the chromophore tips and heating the target tissue. Alternatively, these components can be heat or temperature sensitive such that energy delivery is blocked once the target tissue or non-target tissue reach a prescribed threshold temperature. Alternatively, the backing material may be configured to be opaque, blocking the light delivery to all but the proximal needle shafts, which extend through the backing material to the upper surface of the array system, thereby blocking light delivery to all tissue except those directly in contact with the chromophore tips.

In any of the phototherapy applications, it may be desirable to monitor absorption of the light spectra within the tissue in order to detect changes in the absorption spectra. Changes in the absorption characteristics of the tissue are indicative of changes within the tissue, and can be used to detect treatment efficacy, control extent of treatment, or confirm completion of treatment.

Inductive Heating

Another method of providing a treatment effect to target tissue comprises inductively heating particles within or around the target structures. These particles are preferably metallic (e.g., iron) and of a size that can be introduced into the target tissue region in a non-invasive or minimally invasive manner. For example, a solution of micro-sized ferromagnetic particles can be introduced into the target tissue via injection with a syringe. Alternatively, it may be easier to reach the target tissue using magnetic nanoparticles. Once one or more particles (e.g., ferromagnetic particles) are in or around the target tissue, an electromagnetic energy source from either inside or outside the body can generate an electromagnetic field to create a current in the metallic particles in vivo. These currents will cause resistive heating of the particles and the consequent conductive heating of the target tissue. The electromagnetic energy source can continue delivery of energy to the particles until treatment of the target tissue is completed.

Figure 17:
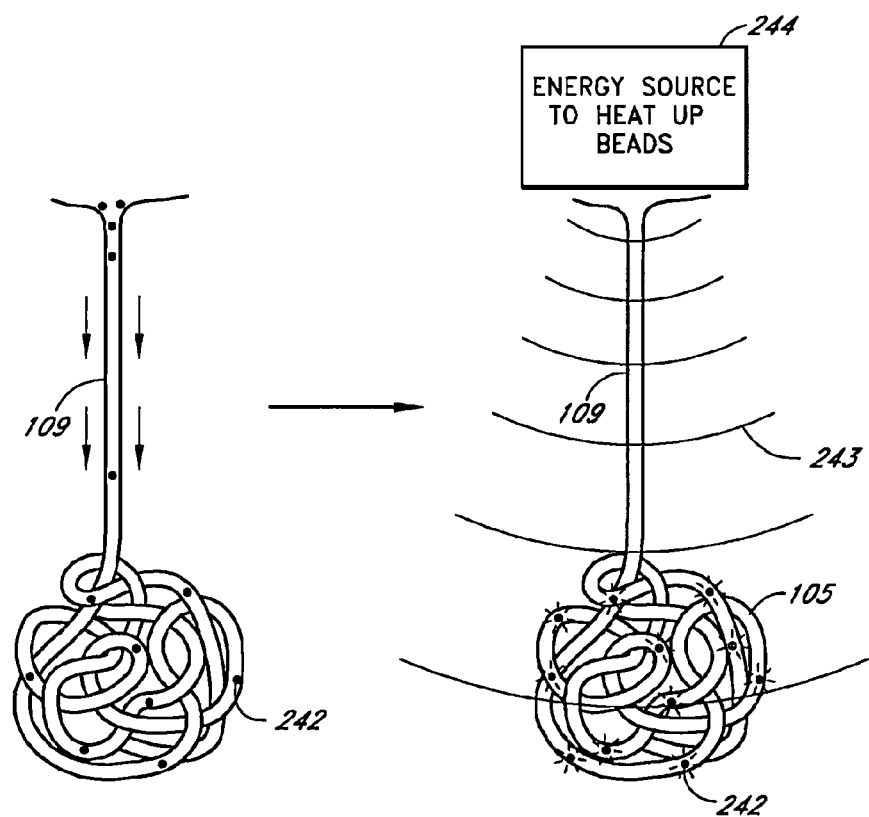
FIG. 17 shows topically-applied aluminum ion particles migrating down a sweat gland duct.

In the case where the target tissue is one or more sweat glands, the particles may be introduced topically via the sweat gland ducts. As with aluminum ion particles in antiperspirants, which are sent down the sweat gland duct to block sweat from reaching the skin surface, topically-applied particles can be introduced into the sweat gland ducts. As illustrated in FIG. 17, these particles 242 can migrate naturally down the duct 109 and into the coil of the gland. Alternatively, pressure can be used to facilitate the travel of these particles 242 to the sweat gland. Alternatively or optionally, iontophoresis may facilitate the delivery of metallic particles 242 into the sweat glands. As mentioned above, electromagnetic energy 243 may be delivered from an electromagnetic energy source 244 to heat the particles 242 and surrounding target tissue 105 until the treatment is completed (e.g., sweat production in the sweat gland has halted and/or the sweat gland has been thermally ablated).

It should be understood that virtually every phototherapy relating to the delivery of color to the target tissue discussed in this specification can be modified to deliver metallic particles for an inductive heating treatment. For example, ferromagnetic particles can be substituted for chromophores, ferromagnetic fluidic suspensions can be used instead of colored solutions, and ferrous-tipped microneedles can be used in place of chromophore-tipped microneedles.

Figure 18A:
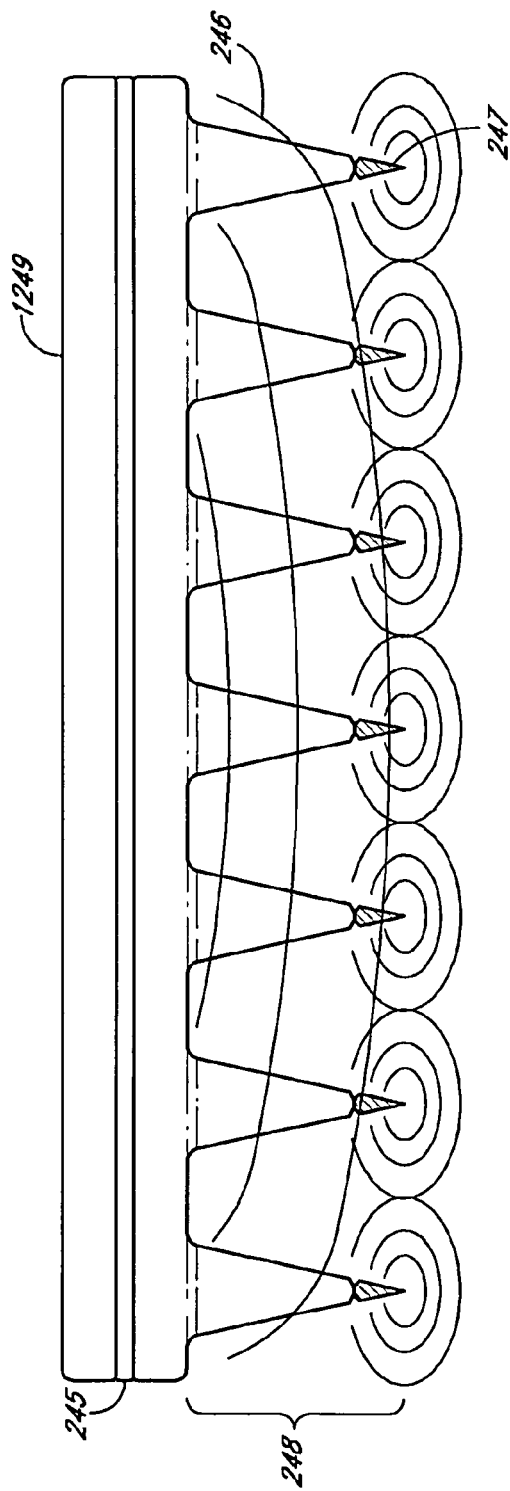
FIG. 18A shows a microneedle patch according to one embodiment.

It may be desirable to remove the ferromagnetic particles from the body following treatment. As such, a microneedle patch comprising a non-magnetic backing system, non-magnetic needle shafts (or proximal portions of the shafts) and non-detachable ferro-tipped microneedles may be employed. Optionally, this embodiment, as illustrated in FIG. 18A, can incorporate an electromagnetic element 245 directly into the backing material 1249. This electromagnetic element 245 can be any structure or material, such as a metal wire, that has electromagnetic properties and is electrically connected to an energy source. The electromagnetic element or an electromagnetic source delivers a field 246 to resistively heat the tips 247, thereby treating the target tissue 105. Following the treatment, the microneedle patch 248 is removed from the patient along with the non-detachable ferromagnetic tips 247.

Ultrasonic energy can be used as another means of treating the target tissue. For example, ultrasound hyperthermia can be induced by delivering an ultrasonic wave to target tissue, causing the tissue to vibrate and heat. Wave frequencies between about 20 kHz and 18 MHz with powers ranging from about 0 to 50 W/cm$^2$ can achieve these results. Treatment may be more effective at frequencies between about 0.1 MHz and 3 MHz and powers from about 720 mW/cm$^2$ to 50 W/cm$^2$.

Figure 18C:
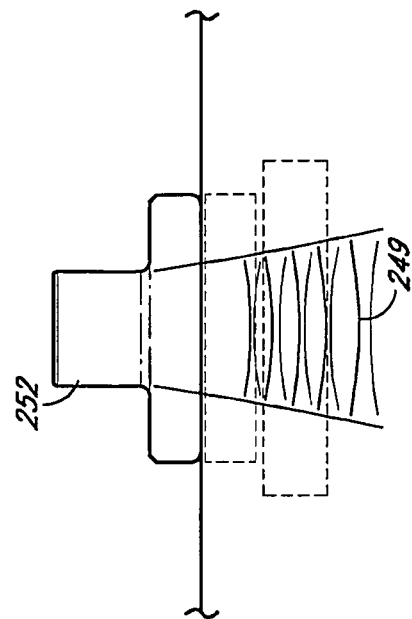
FIG. 18C shows a planar ultrasonic transducer emitting waves as part of an ultrasound treatment according to one embodiment.
Figure 18B:
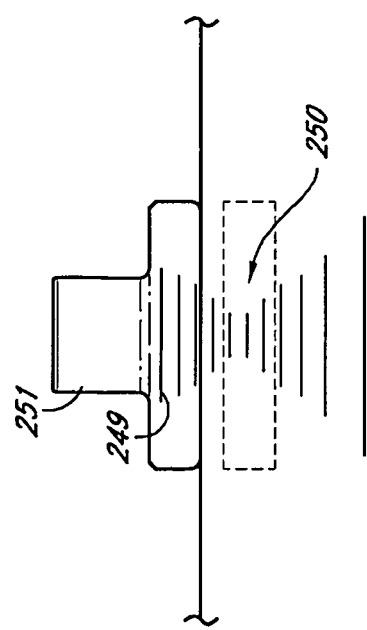
FIG. 18B shows an ultrasonic transducer emitting waves as part of an ultrasound treatment according to one embodiment.

In focused ultrasound treatments, one or more ultrasonic transducers emit waves which meet at a specific focal point at a prescribed distance from the transducer. As shown in FIG. 18B, the convergence of these waves 249 from an ultrasonic transducer 251 causes an intense, cumulative effect at the focal point 250. Once each wave 249 passes the focal point 250, it continues along its radial path and disburses. Multiple transducer embodiments may be oriented in any number of configurations, including linear, radial, and semi-spherical arrays.

In treatments using planar ultrasonic transducers, the emitted waves do not converge at a specific point. As shown in FIG. 18C, the waves 249 instead travel in a planar fashion from the edge of the transducer 252. Additionally, the ultrasound signal can be attenuated such that it terminates at a given distance and does not propagate into the deep non-target tissue. Both planar 252 and focused 251 transducers may induce ultrasound hyperthermia. Used in conjunction with technology for protecting non-target tissue (e.g., cooling system/element), as described elsewhere herein, both methods of ultrasound can isolate heating to the target tissue.

Chemical Thermal Reaction

Figure 19:
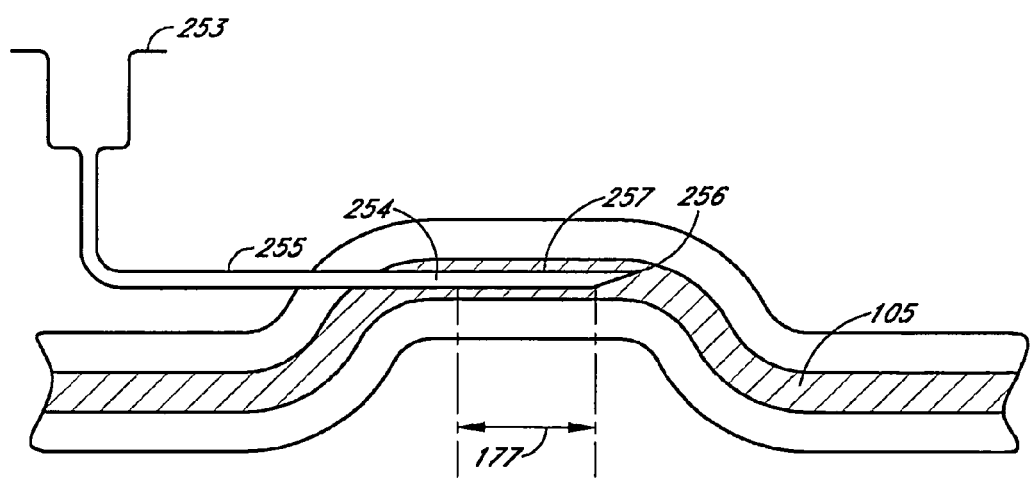
FIG. 19 shows the thermal disablement of sweat glands using a controlled chemical reaction according to one embodiment.

Another method for the reduction of sweat production is illustrated in FIG. 19. In the illustrated embodiment, the sweat glands are thermally disabled by a controlled chemical reaction. This chemical reaction can be either exothermic or endothermic and can involve one or more components. The components can reside in one or more chemical reservoirs 253 in communication with an interstitial probe 254. The probe 254 comprises at least one lumen 255 in communication with the chemical reservoir(s) 253, a sharp tip 256 for penetrating the skin and entering the target tissue and a thermally conductive element 257 comprising a thermally conductive material (e.g., a metal such as copper). The thermally conductive element portion 257 of the probe 254 is configured to be positioned adjacent the target tissue. In one embodiment, the probe 254 with the sharp tip 256 approaches the target tissue parallel to the skin, with a portion of the skin 177 lifted to allow the tip 256 to puncture through tissue. The thermally conductive material 257 is positioned at a location on the probe 254 to be located in the target tissue region. Further details regarding this delivery mechanism are described below. The components can be delivered simultaneously or sequentially such that they mix and undergo a reaction in the thermally conductive element 257. For an exothermic reaction, acid (e.g., HCl, $H_2SO_4$) and water, for example, can be delivered into the thermally conductive element 257 in sufficient amounts to generate sufficient heat to disable and/or ablate the sweat glands via conduction across the element 257. In another embodiment, supersaturated sodium acetate is introduced into the thermally conductive element 257 wherein heat is generated as the solution crystallizes. In an alternate embodiment, the components can be mixed prior to introduction into the thermally conductive element 257. Optionally, a catalyst can be placed within the thermally conductive element 257, or elsewhere along the probe's lumen 255, to facilitate the chemical reaction.

In another embodiment related to treating target tissue, a solution can be used to carry an electric charge to treat the target tissue. In this embodiment, an electrically conductive liquid, such as a hypertonic solution (e.g., saline), can be injected into or around the target tissue with a syringe and needle and then electrically charged by an electrode located proximate to the target tissue. Alternatively, the needle itself may comprise an electrode to directly charge the solution once it is deposited in or adjacent to the target tissue. For example, an array of microneedles (such as that shown in FIG. 14) but also comprising electrodes can be used to deliver hypertonic solution to the target tissue, wherein the tissue is treated by the electrical charge conducted through the solution following activation of the electrodes.

Since sweat already travels a path from the intimate regions of the sweat gland to the surface of the skin, it may be advantageous to use the conductivity of the sweat itself to reach the sweat gland. FIGS. 20A-20C illustrate a method of delivering an electrical charge to sweat glands via the sweat. To prevent injury to the skin surface and surrounding tissue along the duct 109 of the sweat gland, it may be desirable to first apply an insulator coating 258 to cover the skin surface and duct 109 walls while still leaving a path for the sweat to travel from the sweat gland to the surface. Following the application of insulation 258, the patient can be induced to sweat by administering an injection of epinephirine or a cholinergic agent or agonist, stimulating the nerves with an electrical signal, and/or increasing the patient's body temperature via exercise or other means. Once sweat reaches the skin's surface, the operator can apply electrical energy 259 from an energy source (e.g., RF generator 204) to this surface sweat. Through the electrical conductivity of the sweat, the electrical energy 259 from the energy source 204 can reach and disable the sweat gland. It may be desirable for the operator to induce sweating for the entirety of the treatment to maintain continuity of the conductive path in some embodiments.

B. Chemical Treatment

In another embodiment for treating target tissue, a chemical treatment substance can be introduced into or near the target tissue to cause a chemical reaction and resulting treatment effect. For example, alcohols, acids or bases can be delivered to the target tissue to chemically ablate the tissue. More specifically, the injection of small quantities of acids such as tricholoracetate or alphahydroxy acid can result in a treatment effect. Ethanol in concentrations from 5% to 100% has been used to treat hepatocellular carcinoma, thyroid glands, fibroids and cysts in the body and can be used to treat target tissue in this application. The chemical treatment substance can be delivered to the target tissue by any number of mechanisms, including a syringe and needle or a microneedle patch as described elsewhere herein.

C. Mechanical Treatment

Percutaneous Excision

Figure 21A:
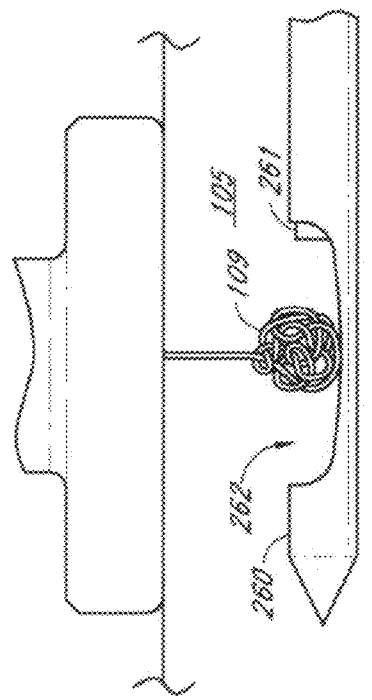
FIG. 21A shows a probe equipped with a retractable blade in a non-retractable position percutaneously inserted under a sweat gland according to one embodiment.
Figure 21B:
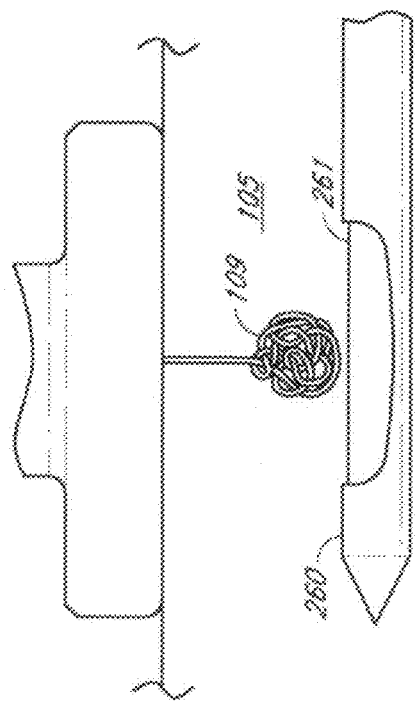
FIG. 21B shows the probe of FIG. 21A having the retractable blade in a retracted position according to one embodiment.
Figure 21C:
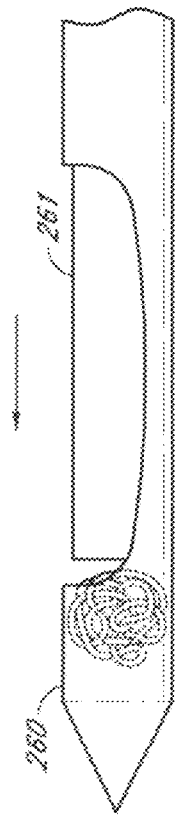
FIG. 21C shows the probe of FIG. 21B having the retractable blade in an advanced position from its retracted position such that the sweat gland is sheared according to one embodiment.

FIGS. 21A-21C illustrate a method and device for percutaneous excision of sweat glands. A probe 260 equipped with a retractable cutter or blade 261 can be percutaneously inserted under target tissue 105 comprising one or more sweat glands. Optionally, imaging technology can be utilized to facilitate placement of the probe/cutter 260. The probe 260 is configured with a hollow chamber 262 such that the blade 261 forms the outer wall of the chamber 262. When the blade 261 is in the retracted position, the chamber 262 is open. When the blade 261 is engaged, the chamber 262 is closed. As illustrated in FIG. 21A, the probe 260 is placed under one or more sweat glands such that at least one sweat gland is supported by the wall of the engaged blade 261. When the blade 261 is retracted, as shown in FIG. 21B, the sweat gland drops into the open hollow chamber 262. When the blade 261 is advanced and engaged, the sweat gland is sheared from the duct 109 and falls within the probe's chamber 262. To facilitate the shearing of the gland, it may be desirable for the blade 261 to rotate, vibrate and/or oscillate. With the blade 261 engaged, the sheared gland is contained within the chamber 262 such that it can be removed with the probe 260 following the treatment or vacuum aspirated coincident with the treatment.

Planar Cutting Devices

In another embodiment for treating target tissue, a planar cutting device can be inserted into the target tissue via a small incision or puncture in the skin. This device can be configured to translate laterally, longitudinally and/or angularly within a plane of target tissue such that it shears, scrapes and/or cuts the target structures within the target tissue to result in a treatment effect. More specifically, the device can move across the interface between the dermal layer and subcutaneous layer of the skin to destroy the eccrine and apocrine glands or, at least, render them inoperable.

In one embodiment of a planar cutting device, the device can have a reduced profile configuration when inserted into the skin and an expanded profile when positioned in the target tissue. For example, as illustrated in FIGS. 22A and 22B, a device 263 comprising at least one wire 264 in a low profile configuration is inserted into an opening in the skin. Following insertion into the skin, an actuator 265 can be used to bow out the wire 264 into an expanded profile and cut and disable target structures within the target tissue during this expansion. In its expanded profile, the wire 264 has access to a large area of target tissue to treat. Optionally, the wire 264 can be expanded and contracted multiple times with the actuator 265 to yield a treatment effect. As shown in FIG. 22B, the actuator 265 may comprise an outer element 266 and inner element 267. The inner element 267 comprises a shaft having a distal end 268 that is coupled to the wire 264 and a proximal end 269 that extends at least partially outside of the patient. The outer element 266 may comprise a collar or sheath that is coupled to the wire 264, wherein the contraction and expansion of the wire 264 can be actuated by the movement of inner element 267 relative to the outer element 266.

In another embodiment, as illustrated in FIG. 23, the planar cutting device comprises a pinwheel cutter 270 that is positioned into the target tissue 105 in a reduced profile configuration. The pinwheel cutter 270 is comprised of a handle 271 for insertion into a least a portion of the target tissue 105 and at least one blade 272 that is rotatably coupled to the distal portion 273 of the handle 271. The blade 272 is configured to rotate about the distal portion 273 of the handle 271 such that the target tissue 105 and target structures in the blade's path are injured and disabled.

Figure 25:
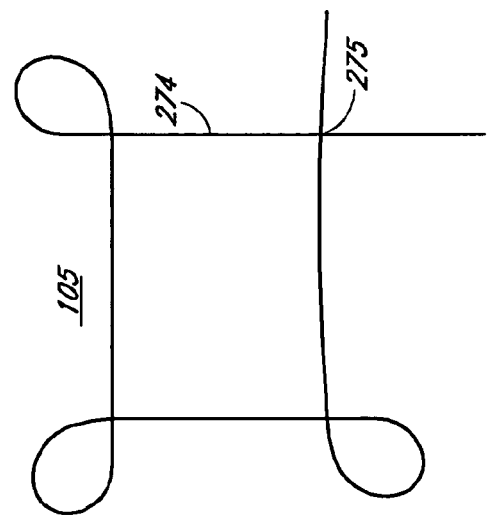
FIG. 25 shows a wire configured to be inserted into target tissue and exiting the target tissue through a sole insertion point according to one embodiment.
Figure 24:
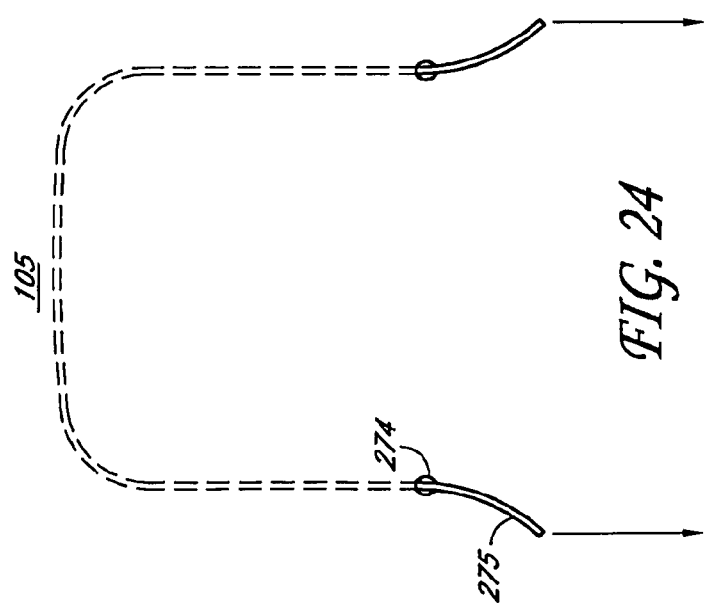
FIG. 24 shows a wire tunneled through target tissue through two insertion points in the skin according to one embodiment.

In another embodiment relating to a planar cutting device, a guided wire can be introduced into the target tissue and routed through the tissue to define a plane of tissue to be treated. As illustrated in FIG. 24, a wire 274 is tunneled through the target tissue 105 through two insertion points 275 in the skin. Once the wire 274 is positioned such that it defines an area of tissue to be treated and each end of the wire 274 is positioned outside of the insertion points 275, tension can be applied to both ends of the wire 274 to pull the wire 274 through the defined plane of tissue. As the wire 274 translates through the tissue, it will injure and disable the target structures in its path. In an alternate embodiment, as shown in FIG. 25, the wire 274 is configured to be inserted into the target tissue 105, guided across the target tissue 105 to define a treatment area and routed out of the body all through a single insertion point 275 in the skin. Once the wire 274 is in place and both ends of the wire 274 are positioned outside the insertion point, the wire ends can be pulled to sweep the wire 274 through the treatment area.

In the planar cutting devices discussed above utilizing guided wires, it may be desirable to route the wire through the target tissue to define a plane of target tissue for treatment. A tunneling instrument with a steerable tip can be used to facilitate the positioning and routing of the wire in and through the target tissue. A tunneling instrument 276 comprising a proximal end 279 and a distal end 278 is shown in FIGS. 26A and 26B. The instrument 276 further comprises a hollow passageway 277 for routing a guided wire 274 from the proximal end 279 through the distal end 278 for placement in the target tissue. The distal end 278 of the instrument 276 is configured for insertion through the skin and into the target tissue. The proximal end 279 of the instrument is located outside the body and used to facilitate the insertion and positioning of the distal end. This instrument 276 further comprises a steering actuator 280 at the proximal end 279 for positioning the distal end 278 of the instrument 276 and facilitating the placement of wire in the target tissue.

In any of the planar cutting devices discussed herein, it is contemplated that a treatment effect can be achieved utilizing the mechanical force of driving the cutting element (wire or blade as the case may be) through the target structures within the target tissue. It should be understood, however, that it is also contemplated that the cutting elements of these devices may also or alternatively comprise energy delivery elements to treat the target tissue as the element moves through the tissue. For example, the wire 274 in FIG. 24 could also be a resistive heating element that is connected to a power source outside the body, wherein the heated wire ablates and coagulates the target tissue as it translated through the planar region of treatment. Alternatively, the wire could be an energy delivery element (e.g., electrode) for delivering one or more forms of energy (e.g., radiofrequency, microwave, ultrasound, etc.) to the surrounding target tissue. Still alternatively, the wire and its electric field can be used to cut and shear the target structures as it is swept through the treatment area.

Photodynamic Glue

Figure 27:
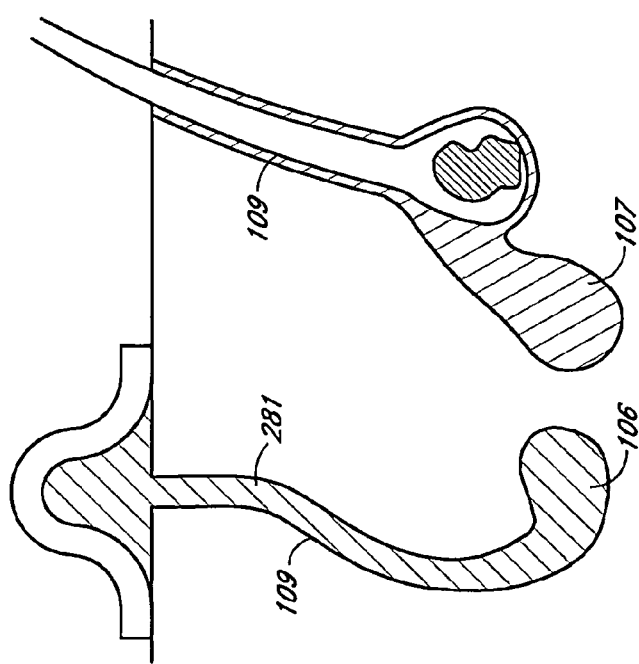
FIG. 27 shows sweat gland ducts filled with photodynamic glue according to one embodiment.

In another method for reducing sweating, as illustrated in FIG. 27, the sweat gland ducts 109 can be filled with photodynamic glue. In this embodiment, a photosensitive dye 281 is introduced into the sweat ducts 109 wherein the dye 281 is exposed to fluorescent light from an outside source. The dye 281 is preferably introduced into the eccrine and/or apocrine glands 106, 107 via topical application. With or without the assistance of pressure, the dye 281 can be applied topically for access to the sweat ducts 109 through the pores. The dye 281 can also be introduced into the gland or duct via injection. When exposed to light of the necessary wavelength and for sufficient duration, the dye 281 undergoes a chemical change through the cross-linking of proteins in the dye. The cross-linked dye seals the sweat duct 109 shut, thereby preventing sweat from reaching the surface of the skin.

In one embodiment, Janus green dye is delivered into the sweat duct. Optionally, pressure may be used to facilitate the delivery of dye into the duct. Once the dye is in the duct, a laser light source from outside the body can deliver light of approximately 650 nanometers to the duct, thereby cross-linking the dye and sealing the duct. Rose Bengal and indocyanine green are other dyes that can be used for this application. Additionally, albumin or other proteins can be added to the dye to facilitate the sealing action.

In another embodiment, a chromophore is mixed with a chemical agent whereby the chemical agent and chromophore will react when exposed to fluorescent light. Specifically, the chromophore will absorb the light and consequently heat the chemical agent, transforming the agent into a seal, thereby preventing sweat from reaching the surface of the skin.

In any of the embodiments disclosed herein relating to sealing the gland ducts, such treatments can optionally include delivering energy that has a particular affinity to water (e.g., microwave) or that is specifically configured to be absorbed by water (e.g., infrared). Application of energy to the sweat-filled glands may result in selective treatment of those glands, with minimal impact to surrounding non-target tissue or structures.

Fibrin Glue

Another method for sealing the sweat glands to reduce sweating comprises introducing biocompatible scaffolding into the sweat duct. As illustrated in FIG. 28, by introducing a scaffolding structure 282 into the sweat duct 109, fibroblast cells 283 will migrate from the skin onto the scaffold 282 as part of the body's healing response and form scar tissue that permanently seals the sweat duct 109. The scaffold 282 can be, for example, a biodegradable fibrin hydrogel, such as glycosaminoglycen chains linked to synthetic polyamine. These scaffolds 282 can be introduced into the ducts 109 from the skin surface using a variety of delivery techniques, including injection, pressure and iontophoresis.

Pressure-Induced Disablement

In another embodiment for reducing sweating, the sweat gland is disabled utilizing positive or negative pressure delivered from the skin surface to the sweat gland via the sweat duct. In one embodiment of this approach, as illustrated in FIG. 29, a piston 284 can deliver pressurized gas (e.g., air) to the sweat gland such that the pressure gradient across the sweat gland wall is sufficient to cause a disabling rupture 285 within the coils 286 of the gland. In one embodiment, a pressure of at least about 200, 300, 400, 500, 600, 700 psi or more may be used. Sufficient pressure can also be achieved by using a volume displacement pump, syringe or suction device.

In another embodiment, as illustrated in FIGS. 30A and 30B, the sweat glands are saturated with a liquid that has a greater volume density as a liquid than as a solid (e.g., water). The liquid may be introduced into the sweat glands by topical application (e.g., a patch), injection or in the case of the liquid being sweat, by inducing the patient to sweat. Cold is then applied to the liquid within the sweat gland using any number of cryogenic techniques. As the liquid freezes, it expands and applies pressure against the wall of the gland. The liquid continues to freeze causing the pressure in the gland 286 to build until a rupture 285 is created in the gland and/or duct 109.

Pressure-Induced Necrosis

Figure 31:
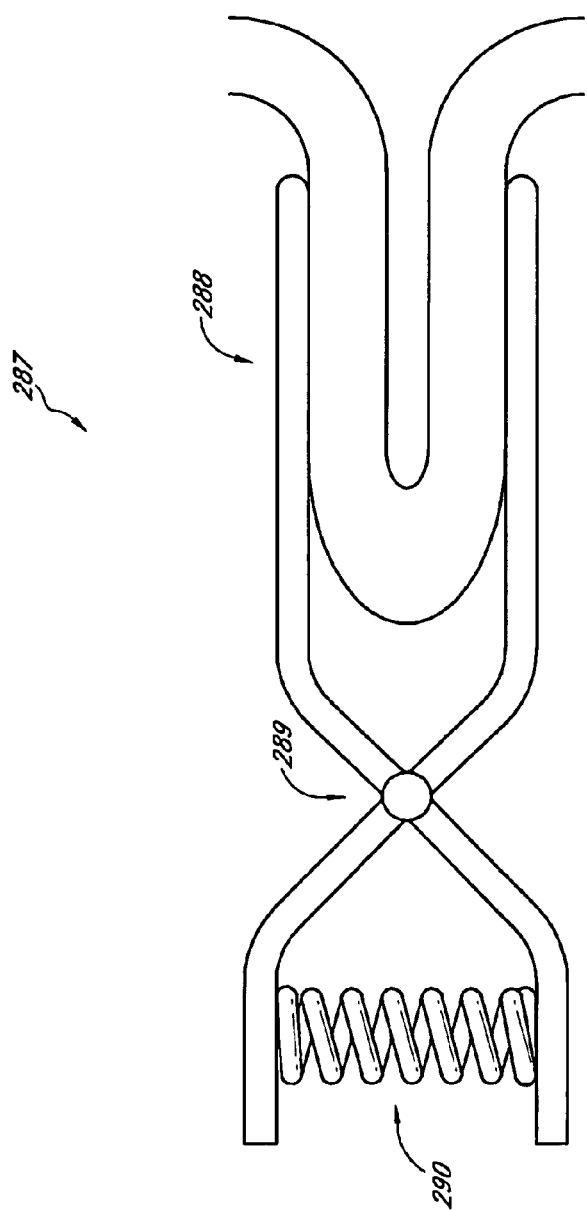
FIG. 31 shows a device for causing pressure-induced necrosis in sweat glands according to one embodiment.

It is believed that sweat glands may be more susceptible to ischemia than surrounding tissue. For example, it is mentioned in *Pressure-Induced Bullae and Sweat Gland Necrosis Following Chemotherapy Induction*, The American Journal of Medicine (Sep. 15, 2004, Volume 117), which is herein incorporated by reference in its entirety, that ischemia from persistent local pressure may precipitate sweat gland necrosis. Accordingly, another treatment for reducing sweat production may comprise applying pressure to a region of target tissue at a level and for a duration sufficient to cause necrosis in one or more sweat glands within the region while minimizing ischemic damage to non-target tissue, alone or in combination with other methods described herein. A device 287 for causing pressure-induced necrosis in sweat glands is shown in FIG. 31. This device 287 may comprise a clamp or pincher 288 for engaging the skin at its distal end and an actuator 289 for the operator to apply and sustain pressure. Alternatively, the actuator 289 may further comprise a spring element 290 so that constant pressure can be maintained during treatment without the need for operator assistance or intervention. The device 287 may comprise an array of clamps or pinchers 288 so that multiple locations can be treated at once. In an alternative embodiment, the device 287 could be configured for the patient to wear over a period of a few hours or a few days to achieve the desired treatment effect. For example, to achieve axillary anhidrosis, a variation of the device shown in FIG. 31 can be strapped to the patient's axillae so that it can be worn overnight or over the course of a day.

Acoustic Cavitation

Figure 32:
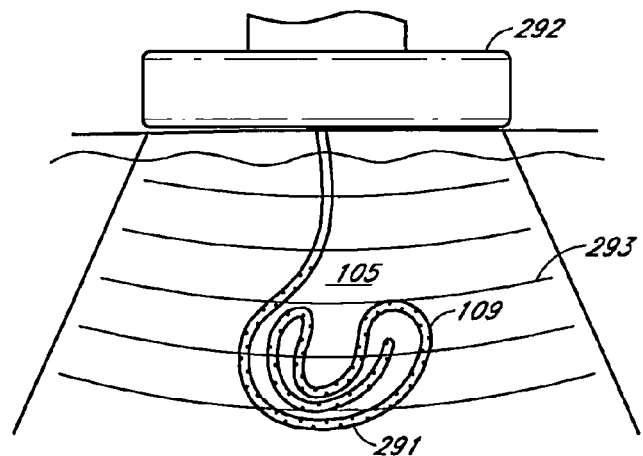
FIG. 32 shows a target tissue having microbubbles and microspheres subject to rupturing by an ultrasonic transducer device according to one embodiment.

In another embodiment, micro-bubbles of air are introduced into the target tissue and cavitated by an ultrasonic signal to achieve a treatment effect. For example, as illustrated in FIG. 32, encapsulated microspheres or microbubbles 291 (e.g., OPTISON™ sold by GE Healthcare) are delivered to the target tissue 105 whereby an energy delivery device from outside the body (e.g., an ultrasound transducer 292) delivers energy 293 (e.g., an ultrasound signal) to the target tissue 105 to rupture the microbubbles/microspheres 291. The microbubbles 291 can be introduced into the glands through either topical delivery via the ducts 109 or injection. The ultrasound transducer 292 can be configured to deliver a wave with an amplitude and frequency sufficient to violently collapse the microbubbles/microspheres 291 residing in and around the target structure, such that sufficient energy is released to disable the target structure and render a treatment effect. Alternatively, cavitation can be induced in the sweat gland by increasing the sonic pressure applied to the tissue above a threshold necessary to cause native cavitation without exogenous bubble introduction. Sodium and other ions in the sweat may act a nidus for bubble formation. For example, the types of pressures provided by shock wave lithotriptors may be sufficient to generate this cavitation.

i. Protection of Non-Target Tissue

Thermal Treatment to Protect Non-Target Tissue

In thermal treatments of tissue, it may be beneficial to protect against the unnecessary and potentially deleterious thermal destruction of non-target tissue. This is particularly the case in sub-dermal treatments since excess energy delivered to the epidermal and dermal layers of the skin can result in pain, discomfort, drying, charring and edge effects. Moreover, drying, charring and edge effects to surrounding tissue can impair a treatment's efficacy as the impedance of desiccated tissue may be too high to allow energy to travel into deeper regions of tissue.

Figure 33:
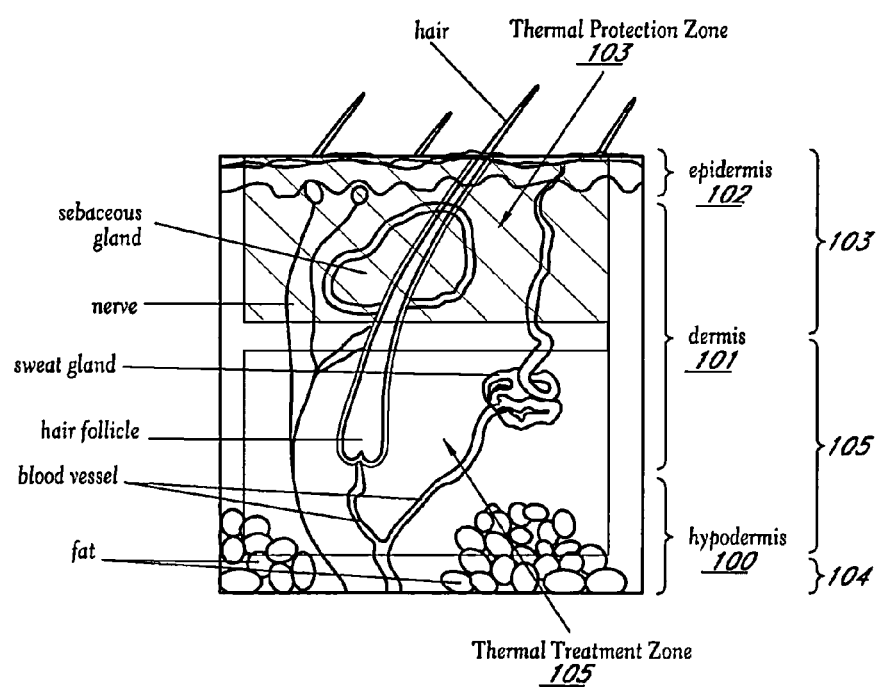
FIG. 33 shows a cross-sectional view of a target tissue having a zone of thermal treatment according to one embodiment.

To avoid thermal destruction to non-target tissue and any complications associated therewith, the energy delivery device can include a cooling element for providing a cooling effect to the superficial non-target tissue (e.g., the epidermis and portions of the dermis). By conductively and/or convectively cooling the epidermis and allowing the cooling effect to penetrate into the dermis, the cooling element will establish a zone of thermal protection 103 for the superficial non-target tissue as illustrated in FIG. 33. With the cooling element providing this zone of protection 103, the target tissue (e.g., zone of thermal treatment 105 in FIG. 33) can be treated with minimal risk of thermal damage to non-target tissue.

To further reduce the risk of pain and/or other uncomfortable sensations associated with thermal treatment, the cooling element can further cool the superficial non-target tissue to create a numbing effect. Depending on the type of thermal treatment employed and the associated need for complementary cooling, the cooling treatment and resulting cooling and/or numbing effect may be applied before, during and/or after the thermal treatment. Protective cooling may also be applied in an alternating fashion with the heating treatment to maximize energy delivery while minimizing adverse effects to non-target tissue.

The cooling element can take many forms. The cooling element can be a passive heat sink that conductively cools the skin, such as a layer of static, chilled liquid (e.g., water, saline) or a solid coolant (e.g., ice, metal plate) or some combination thereof (e.g., a metal cylinder filled with chilled water). The cooling element can also provide active cooling in the form of a spray or stream of gas or liquid, or aerosol particles for convective cooling of the epidermis. A thermoelectric cooler (TEC) or Peltier element can also be an effective active cooling element. Alternatively, an active cooling element can comprise a thermally conductive element with an adjacent circulating fluid to carry away heat.

The cooling element can also be incorporated into the device as an internal cooling component for conductively cooling non-target tissue. For example, an energy delivery device can couple a cooling component to the energy applicator, where the cooling component can actively or passively provide conductive cooling to adjacent tissue. When passive cooling is provided, the cooling component may comprise a cold metal plate or block. When active cooling is provided, the cooling component may comprise a thermally conductive element, wherein a chilled liquid (e.g., water, dry ice, alcohol, anti-freeze) is circulated through the element's internal structure. For example, in microwave energy delivery devices that include a dielectric, the dielectric itself can be a cooling component. In another example, the cooling component can be incorporated into an electrode in embodiments where RF energy is delivered to skin tissue.

Figure 34B:
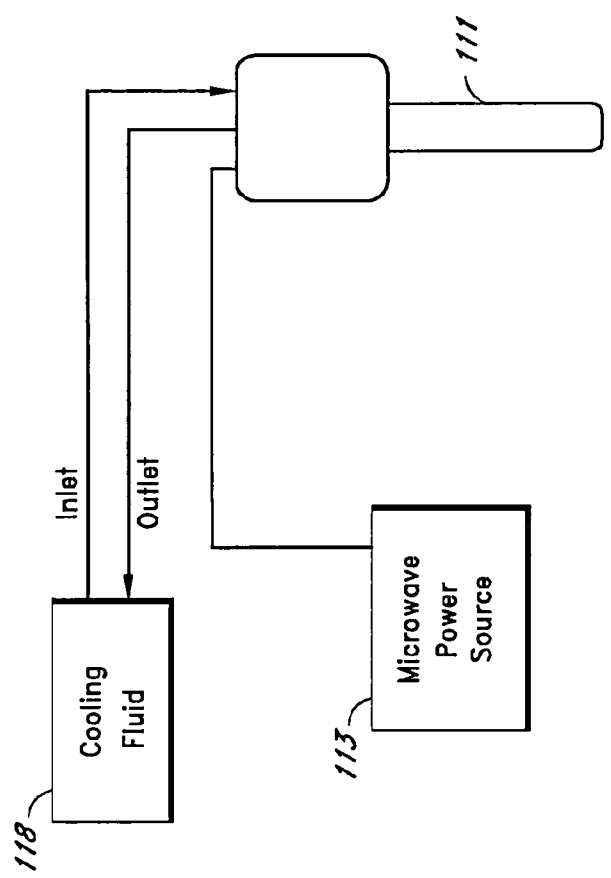
FIG. 34B shows a schematic view of a cooling source located remotely from an energy source and energy applicator according to one embodiment.

As shown in FIG. 34A, a cooling component 115 can be incorporated into an energy delivery device 117 comprising at least one microwave antenna 120, such as described above. In this embodiment, fluid is used to cool adjacent skin tissue 119. This convective cooling can be enhanced by a coolant circulator 118 that could optionally be integrated within, coupled to or located remotely from the energy generator 113. As shown in FIG. 34B, the cooling circulator 118 is located remotely from both the energy source 113 and energy applicator 111. The properties and characteristics (e.g., medium, flow rate, temperature) of the circulating fluid (gas or liquid) can be selected and modified to achieve the desired cooling effect in light of the amount and rate of energy delivered to the target tissue.

A cooling element can also be used to provide a directional component to a thermal treatment. For example, the needle 294 illustrated in FIG. 35A can be configured with a proximal region comprising a cooling element 295 and a distal end comprising an electrode tip 296. In this configuration, thermal damage can be isolated to the target tissue while non-target tissue is protectively cooled along the needle's proximal region by the cooling element 295. Optionally, the electrode 296 itself can be equipped with a cooling component such that internally-circulated chilled fluid can conductively cool tissue adjacent to the electrode 296, thereby minimizing unnecessary damage to non-target tissue.

FIG. 35B shows an energy delivery element comprising a metal electrode 297, an inner tube 298 and an outer circumferential surface 299. In this embodiment, the metal electrode 297 comprises a cooling component. An energy generator supplies the metal electrode 297 with electrical energy to deliver an electric field to adjacent tissue. The cooling component of the electrode 297 conductively cools the adjacent tissue, wherein a coolant is delivered to the electrode 297 through the inner tube 298 and then circulated out through the annular space between the inner tube 298 and outer circumferential surface 299.

In minimally invasive thermal treatments where the energy delivery device delivers energy from a position proximate or adjacent to the target tissue, surface cooling can be utilized in addition to or instead of subcutaneous cooling to protect non-target tissue. For example, in FIG. 11, an energy delivery device comprising a needle 205 is depicted delivering energy 210 subdermally. A cooling element can be incorporated into this delivery device to provide protective cooling adjacent to the heat treatment and/or, as illustrated, a cooling element can be applied topically to protect the superficial non-target tissue.

In another embodiment comprising a minimally-invasive treatment, a cooling element can be incorporated into a needle such that a proximal portion and a distal portion of the needle comprise cooling elements. In this configuration, an electrode or other energy delivery element can be situated between the proximal and distal cooling elements such that the superficial non-target tissue adjacent to the proximal cooling element and the deep non-target tissue adjacent to the distal cooling element are protectively cooled. Accordingly, the thermal treatment is regulated from above and below the treatment area such that treatment of target tissue is localized.

It may also be desirable to utilize a cooling element to improve the efficiency of the overall thermal treatment. As previously mentioned, a thermal treatment may be undermined by the overheating and desiccation of tissue adjacent to the electrode or other energy delivery element. Since desiccated tissue has relatively high impedance, energy delivery beyond the desiccated tissue is compromised, thereby resulting in an inefficient, inconsistent and potentially ineffective treatment. By incorporating a cooling element or cooling component proximate to the treatment site, excess heat can be absorbed by the energy delivery device and removed from the body. For example, an electrode or other energy delivery element can include a cooling component to extract excess heat from the electrode and adjacent tissue and facilitate thermal conductivity for a deeper treatment.

In another embodiment, a heat pipe can be incorporated into the energy delivery element to absorb and expel excess energy from the treatment area. FIG. 36 depicts an energy delivery device 1200 comprising a bipolar pair of needle-tipped electrodes 1201, 1202, wherein the electrodes 1201, 1202 are located adjacent to target tissue 105. Incorporated within these electrodes 1201, 1202 are cooling components comprising heat pipes 1204, wherein the heat pipes 1204 are connected to heat sinks 1203 located outside of the body. The heat pipes 1204 operate on the principle of evaporative cooling, whereby a fluid in the pipe 1204 (e.g., water, alcohol, ammonia, etc.) is rapidly condensed and evaporated at opposite ends of the pipe 1204 to transfer heat along the tube. In this example, the heat sink 1203 draws heat away from the vaporized fluid at a proximate portion of the heat pipe 1204 in order to condense the fluid into a liquid. Once it is condensed, the liquid travels down towards the electrode at the distal portion of the pipe and absorbs heat from the electrode and surrounding area until it vaporizes. The vapor then travels up to the proximal portion of the heat pipe 1204 to once again begin the heat exchange cycle.

Figure 37B:
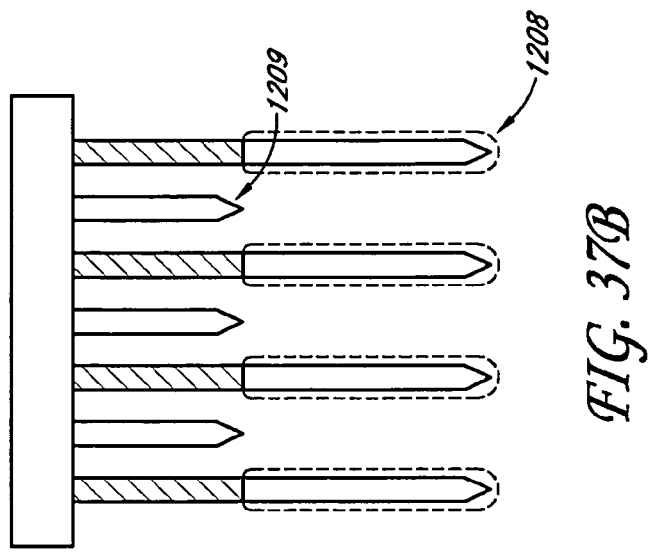
FIG. 37B shows cooling electrodes in an alternating sequence with monopolar electrodes according to one embodiment.
Figure 37A:
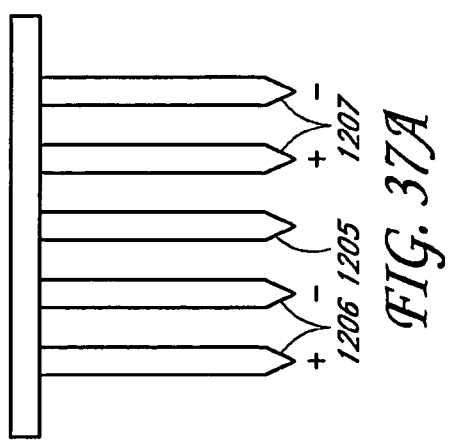
FIG. 37A shows a cooling electrode comprising a heat sink positioned between two pairs of bipolar needle electrodes according to one embodiment.

In another embodiment, cooling elements can be interspersed with heating electrodes to achieve the desired thermal protection. For example, as shown in FIG. 37A, a cooling electrode comprising a heat sink 1205 is positioned between two pairs 1206, 1207 of bipolar needle electrodes. The heat sink 1205 can be a thermally-conductive metal with a high heat capacity. Optionally, the heat sink 1205 may further comprise a chamber for holding a static or circulating cooling medium for absorbing and carrying away excess heat. In the example illustrated in FIG. 37A, the cooling element 1205 is of a length equal to the adjacent energy delivery elements 1206, 1207 such that excess heat can be drawn away from the treatment area to both protect non-target tissue and avoid the adverse consequences of desiccation of target tissue. In another example, as illustrated in FIG. 37B, the cooling elements 1209 are in alternating sequence with monopolar electrodes 1208, wherein the cooling elements 1209 are shorter than the energy delivery elements 1208 so that they primarily provide protective cooling to the superficial non-target tissue. In any of these embodiments, the cooling elements 1209 may alternatively comprise electrically active elements such as thermo-electric coolers (TECs) or Peltier elements.

In applications where the target tissue is thermally treated using cryotherapy, it may be beneficial to provide a heating element to protect non-target tissue from the undesirable effects of cooling. As various modes of protective cooling have been disclosed above with respect to heating treatments, the same conductive and convective techniques can analogously be employed using a heating element to protectively heat non-target tissue in cryotherapy treatments. In addition to the modes of conductive and/or convective heat exchange already disclosed, a heating element can also use resistive, radiant and/or inductive heating to provide the necessary amount of heat to protect non-target tissue. Such protective heating treatments can be applied before, during, after and/or in alternating sequence with the application of cryotherapy to treat the target tissue. Further ii. Geometries In many of the embodiments disclosed herein, treatment is administered topically and/or in a minimally-invasive fashion to achieve the desired treatment effect on target tissue. In some of these embodiments, the skin is depicted as a flat, multilayer plane of tissue, wherein treatment can be administered to target tissue in a manner that is virtually perpendicular to its planar surface. It should be understood that although a treatment may be disclosed with respect to a particular skin geometry (e.g., perpendicular topical delivery, perpendicular percutaneous insertion, etc.), such treatment may be administered with respect any number or variety of geometries, including those discussed below.

Elevated Skin Treatment

In energy treatments involving the delivery of RF, infrared, microwave or ultrasound, for example, there is the risk that the delivered energy may penetrate too deep into the body and cause harm to the deep non-target tissue, associated critical structures (e.g., blood vessels, lymph nodes, muscle tissue, etc.) and body organs. Therefore, it may be beneficial to elevate the target tissue comprising portion of the skin from the underlying tissue. Such elevation can be achieved through manual manipulation by the clinician or facilitated using any number of devices. For example, as illustrated in FIG. 38, a vacuum 147 can be used to pull and hold the skin 119, thereby elevating it for treatment. Optionally, a vacuum-suction device can be incorporated into the energy delivery device such that suction and energy delivery can be applied in unison.

In another embodiment, a tool utilizing a sterile adhesive can effectively prop up the skin for treatment. More simply, however, a clinician can use any number of clamps, tongs or other devices to achieve and maintain skin elevation for and during treatment.

Non-Perpendicular Percutaneous Insertion

In treatments comprising minimally-invasive insertion of a treatment device, it may be desirable to administer treatment by inserting the device into the skin tissue in a non-perpendicular fashion. This approach may provide multiple benefits. First, by inserting the device at an angle, the risk of reaching and damaging critical structures in the subcutaneous tissue may be minimized. For example, an angular insertion may avoid the blood vessels, lymph nodes and muscular tissue that lie beneath the subcutaneous tissue. Second, a non-perpendicular approach may have a higher likelihood of achieving a planar treatment. Since the target tissue resides at a plane that's parallel to the skin's surface, it is believed that an angular approach can create a wider treatment per insertion.

Figure 39:
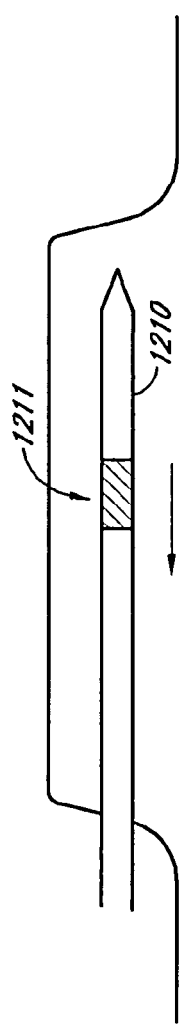
FIG. 39 shows a needle comprising an energy delivery element according to one embodiment.

For example, a device can be inserted into the skin at an angle and then tunneled between the dermal layer and subcutaneous layer in parallel to a region of target tissue. As shown in FIG. 39, a needle 1210 comprising an energy delivery element can be used to deliver an energy treatment to the target tissue in a planar fashion. In this embodiment, a needle 1210 comprises an electrode, and a small portion 1211 of the needle is used to administer multiple treatments to the parallel plane of target tissue as the needle is longitudinally retracted along its path of insertion. Alternatively, the electrode is slidably engaged with the needle 1210 and treatment is administered by longitudinally translating the electrode along the needle 1210 while the needle 1210 itself remains in place. In another alternative embodiment, the length of the needle 1210 may comprise an electrode and a segmented insulator sleeve comprising an electrical insulator (e.g., polyimid) such that the sleeve can be translated along the length of the electrode so that only a portion of the electrode is exposed at a time. Still alternatively, the needle 1210 comprises multiple electrodes along its length that are dynamically activated (e.g., monopolar, bipolar) simultaneously or sequentially to yield a treatment effect across the plane of target tissue.

Figure 40:
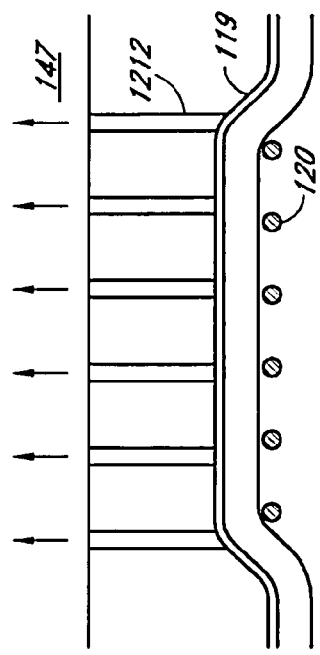
FIG. 40 shows a side view of a vacuum pulling and holding skin implanted with electrodes according to one embodiment.

Additionally, it may be beneficial for the operator to manipulate the patient's skin to facilitate a non-perpendicular insertion. By pulling, holding, and/or squeezing the skin prior to, during and/or following insertion of the device, the operator can tunnel the device alongside the plane of target tissue in order to achieve a planar treatment. This manipulation of the skin can be performed manually by the operator or it can be facilitated by any number of devices, including those discussed above with respect to skin elevation. As shown in FIG. 40, a vacuum suction 147 having multiple vacuum channels 1212 can be used to elevate the skin 119 and facilitate the non-perpendicular insertion of one or more energy delivery elements 120. While FIG. 40 shows six vacuum channels 1212, it should be understood that as few as one, two, three, four, five and as many as seven, eight, nine, ten or more channels can be used to provide suction.

Figure 41:
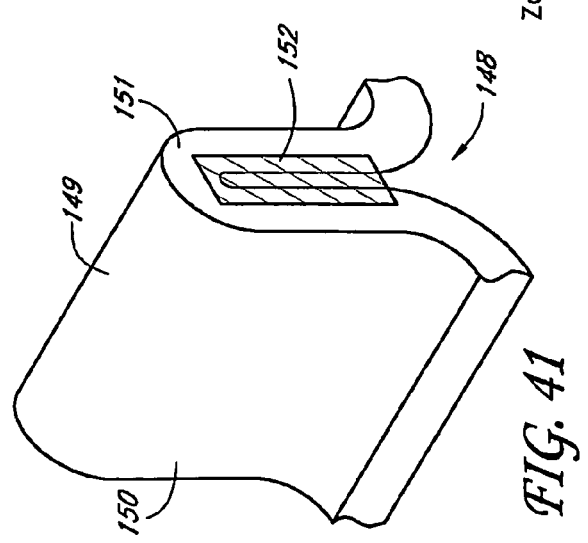
FIG. 41 shows an example of a typical skin fold.

In another skin geometry configuration, it may be beneficial to first pinch and fold the patient's skin prior to delivering energy to the target tissue. Following the optional administration of a local anesthetic such as lidocaine (topically or subdermally), the patient's skin can be grasped and pulled partially away such that the epidermis, dermis and subcutaneous layer are separated from the underlying skeletal muscle. Once separated, the skin could then be folded such that neighboring sections of the skin abut one another wherein the subcutaneous layer of one side of the fold faces the subcutaneous layer of the other side of the fold. Isolating these adjacent subcutaneous layers results in a treatment zone that is dense with target tissue and target structures. FIG. 41 shows an example of a typical skin fold 148. The skin fold 148 comprises a top 149, two sides 150 (only one visible), two edges 151 (only one visible) and a zone of "sandwiched" target tissue 152 along the longitudinal length of the fold (i.e., treatment zone).

Focusing treatment on the target tissue rich region within the skin fold 148 will allow for a more efficient procedure as two adjacent layers of target tissue can be treated in a single treatment. Additionally, treatment can be administered from one or more orientations (e.g., both sides of the fold 148), which can result in a more effective and reliable treatment. Also, since the skin is being pulled away from the body, damage to critical subcutaneous structures is minimized. Moreover, there is less risk of disruption due to thermal conductivity of blood flow since the target tissue is further from the blood supply and the act of pinching or vacuuming the skin fold 148 into position will temporarily cut off the blood supply to the folded tissue. Additionally, the neural activity caused in the skin by the folded configuration may reduce the patient's pain sensation during treatment under the aforementioned gate control theory of pain management.

Figure 42:
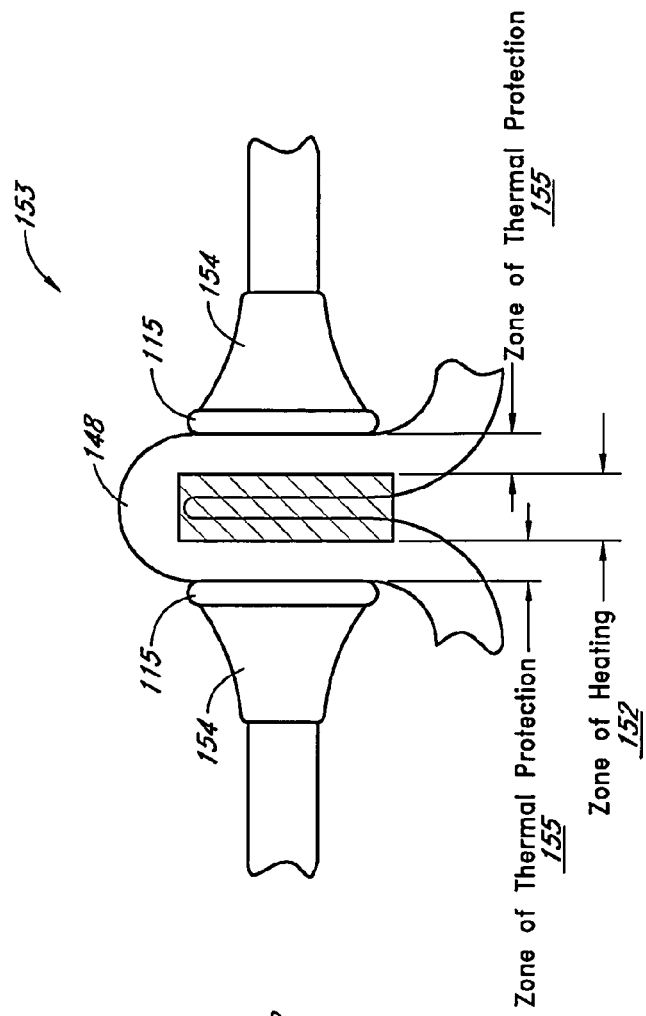
FIG. 42 shows a skin fold being treated by an energy delivery device comprising two energy delivery elements according to one embodiment.

In one embodiment, as illustrated in FIG. 42, the skin fold 148 is treated from opposite sides by an energy delivery device 153 comprising two energy delivery elements 154. The energy delivery elements 154 are configured to deliver energy to the treatment zone 152 in the middle of the fold 148. In the case of energy delivery devices 153 that comprise one or more microwave antennas connected to one or more microwave generators, the microwave energy can cross the outer epidermal layers from each side of the skin fold 148 and penetrate deep into the treatment zone 152. To optimize the delivery of microwave energy to target tissue, a dielectric can optionally be used in this treatment. As shown in FIG. 42, cooling elements 115 can also be used on the skin surface to create a zone of protection 155 for non-target tissue. Additionally, the device 153 can be configured with a cooling element 115 and/or dielectric element on either side of the skin fold 148 to stabilize the fold during treatment.

Alternatively, the embodiment illustrated in FIG. 42 can achieve a treatment effect by delivering RF energy instead of microwave energy. This energy delivery device would comprise one or more electrodes on either or both sides of the skin fold. These electrodes would either touch the skin surface or be in close proximity to the skin to deliver an electric field to the skin tissue. Portions of the skin tissue would be resistively heated by the electric field with surrounding portions being conductively heated. One or more cooling elements can be used on either side or both sides of the skin fold to conductively and/or convectively cool superficial non-target tissue. Alternatively, the electrode itself can have a cooling component to provide a cooling effect at the point of contact between the skin surface and electrode.

FIGS. 43A-43C depict three embodiments of treatment devices using different energy sources (RF, microwave and cryogenic) that are configured for insertion into and across the skin fold 148. Minimally-invasive insertion allows for a more localized treatment of target tissue such that damage to non-target tissue is minimized. The devices depicted in these figures may include one or more needles, micro-needles, stylets or catheters for insertion into the epidermal layer of the skin fold such that the device reaches at least a portion of the treatment zone 152. Optionally, the device can be inserted on one side of the skin fold 148 such that the distal end of the device will exit the other side of the fold 148. The device may further comprise one or more stabilizing plates on either side of the skin fold 148 to support each end of the inserted device. The stabilizing plates can optionally comprise cooling elements to treat the epidermal tissue and create a zone of protected non-target tissue. Moreover, the device can be physically or electrically connected to an energy generator for supplying energy to be delivered to the target tissue.

FIG. 43A illustrates a minimally-invasive RF delivery device 1245 including RF generator 204 comprising one or more needles 207 for insertion into the skin fold. The needles 207 comprise one or more electrodes 206 strategically placed along the length of the needle 207 to optimize energy delivery to and treatment of target tissue 152. Alternatively, the needle 207 itself can be an electrode. To minimize the treatment of non-target tissue, the electrode comprising portion 206 of each needle 207 can be insulated at portions 205 that will not be proximate to target tissue 152. To reduce the risk of edge effects, charring and/or desiccation at and around the point of contact between the electrode 206 and tissue and resulting loss of conductivity, the needle 207 can be coupled to one or more cooling elements or the electrode itself can incorporate a cooling component.

The embodiment depicted in FIG. 43B comprises a minimally-invasive microwave delivery device 1213 comprising one or more microwave antennas 120 for insertion into the skin fold 148. The antennas 120 can be inserted such that they are adjacent to the target tissue 152 to maximize delivery of microwave energy to the sweat glands within the treatment zone 152. To optimize the delivery of microwave energy to target tissue over the course of the treatment, one or more antennas 120 of the device 1213 may optionally be insulated with a dielectric material.

The embodiment depicted in FIG. 43C comprises a minimally-invasive cryogenic therapy device 1243 including cryotherapy source reservoir 1244 and one or more injection needles, stylets, cannulas or catheters for insertion into the skin fold 148. The stylets 211 should have one or more passageways and openings for delivering a cryogenic fluid to the target tissue 152 at a rate and volume sufficient to freeze, ablate and/or disable one or more sweat glands within the target tissue 152. A heating element may optionally be used to protect non-target tissue from disruptive or destructive damage. This heating element could be located as part of or alongside a stabilizer plate to treat the skin tissue from the skin surface. Alternatively or additionally, the heating element could be located along the interstitial portion of the device to provide protective heating to the non-target tissue.

Figure 44:
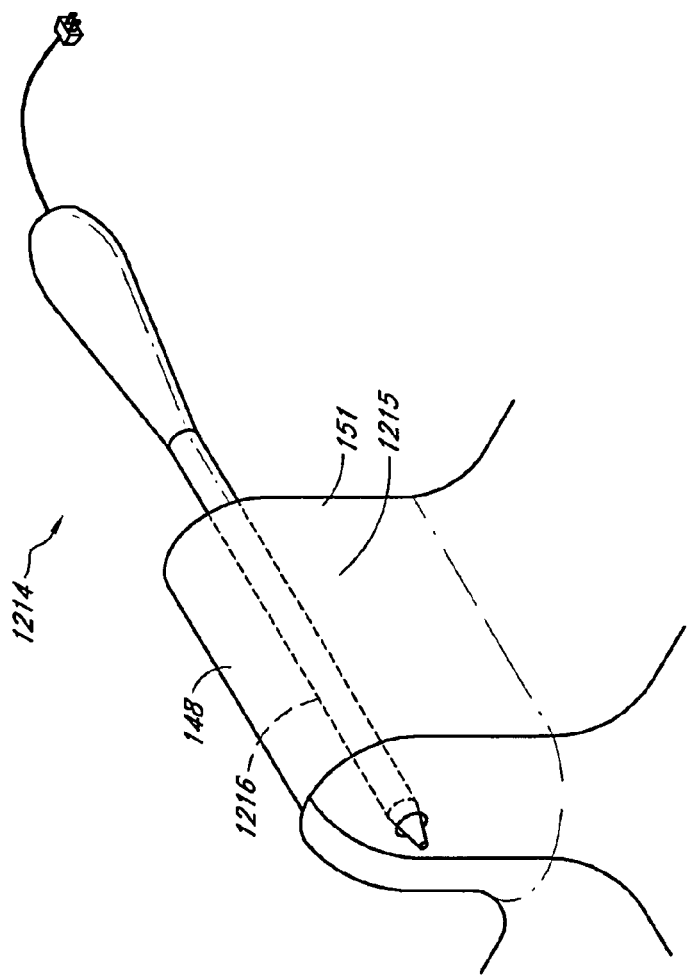
FIG. 44 shows an energy delivery device according to one embodiment inserted through an edge of a skin fold and positioned along the longitudinal axis of the fold.

In the minimally-invasive treatments illustrated in FIGS. 43A-43C, the energy delivery devices are inserted across the skin fold 148 (e.g., transverse to the longitudinal axis of the fold). However, it should be understood that these devices can be configured to be inserted through either edge and along the longitudinal length of the fold as well. For example, as illustrated in FIG. 44, an energy delivery device 1214 is shown inserted through an edge 151 of the skin fold 148 and positioned along the longitudinal axis of the fold 148. As shown in FIG. 44, the needle can optionally pierce the edge of the fold 148 opposite the insertion point. The energy delivery device 1214 comprises a needle having a thermally conductive outer wall 1215 and an inner resistive heating element 1216. A power source (e.g., battery, outlet, generator, etc.) delivers power to resistively heat the heating element and outer wall thereby thermally treating the surrounding target tissue.

FIG. 45 illustrates another approach for a minimally-invasive treatment utilizing the skin fold configuration. In this embodiment an energy delivery element 209 is inserted through the top of the skin fold 148 so that it is positioned in the approximate middle of the treatment zone 152. This approach provides certain advantages over other approaches in that treatment is delivered directly to the immediately surrounding target tissue 152 with minimal treatment to non-target tissue. As shown in FIGS. 46A and 46B, an array or rows of monopolar electrode needles 207 can be used to deliver treatment along the longitudinal length of the skin fold. These elements can include insulation 205 at their proximal ends to prevent unnecessary treatment of the non-target tissue at the top of the skin fold. Alternatively, a row of bipolar electrode pairs 1206, 1207 can be used to deliver treatment that will result in a consistent planar lesion within the target tissue.

Figure 47B:
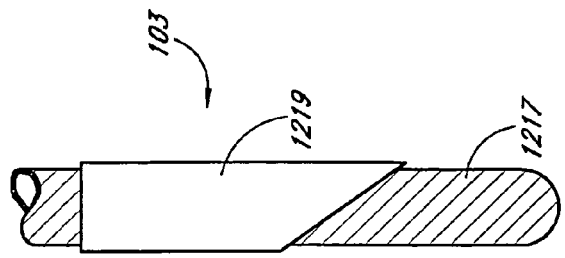
FIG. 47B shows an energy delivery device inserted at the top of a skin fold after a needle and blunt dissector electrode are inserted according to an alternate embodiment.
Figure 47A:
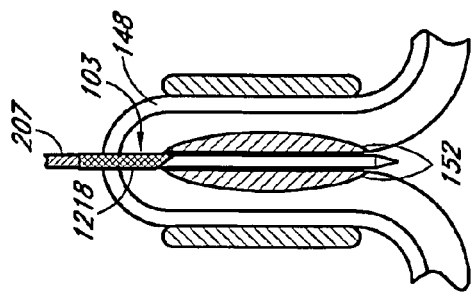
FIG. 47A shows an energy delivery device inserted at the top of a skin fold after a needle and blunt dissector electrode are inserted according to one embodiment.

FIGS. 47A-47B show a variation of the embodiment illustrated in FIG. 45 depicting a device insertion at the top of the skin fold 148. In this embodiment, a needle 207 having a hollow passageway 1218 is first inserted into the top of the fold 148 and through the superficial non-target tissue 103. Once the needle 207 is in place, a blunt dissector electrode 1217 is inserted into the needle's passageway 1218 and driven through the target tissue 152. When the blunt electrode 1217 is placed in the treatment zone 152, it can be activated to deliver an electric field to the treatment area to administer the thermal treatment. Optionally, the inserted hollow needle 207 can be insulated by a insulator 1219 (as shown in FIG. 47B) to protect non-target tissue 103 from the electric field.

The use of a blunt electrode may provide certain benefits over those available using a needle electrode. First, blunt dissection tends to follow the naturally occurring tissue plane that exists at the junction of the dermal and subcutaneous layers, whereas one or more needle embodiments may dissect whatever tissue is in its path. Therefore, a blunt dissector can facilitate accurate electrode placement. Second, the blunt electrode's current density is more evenly distributed than that of a needle electrode. The current density of the needle electrode is concentrated at the needle's sharp tip such that the tissue immediately at the tip is heated and desiccated before a significant amount of energy is able to reach the surrounding tissue. Conversely, the current density of a blunt electrode is evenly distributed to allow for a more consistent and predictable treatment.

Figure 48:
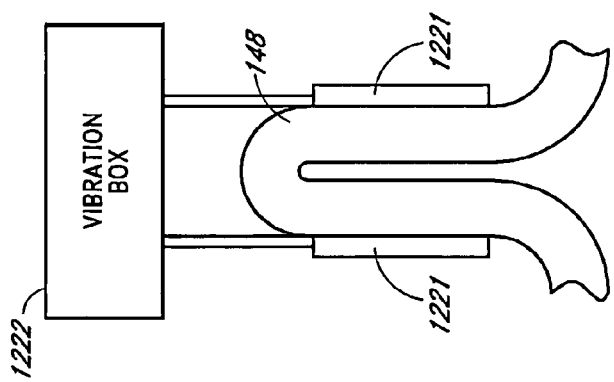
FIG. 48 shows one or more paddle elements connected to a vibration source removably coupled to each outer side of a skin fold according to one embodiment.

Another embodiment utilizing the folded skin 148 configuration is depicted in FIG. 48. In this embodiment, one or more paddle elements 1221 are removably coupled (e.g., via adhesive) to each outer side of the skin fold 148. The paddles elements 1221 are operatively connected to a vibration source 1222 that drives movement of the paddles 1221 in alternating sequence. Alternating movement of the paddle elements 1221, particularly between paddles on each side of the skin fold 148, creates friction between the adjacent subcutaneous layers sandwiched within the skin fold 148. Because the sweat glands within these subcutaneous layers possess a solid, grainy structure, the frictional contact between the abutting subcutaneous layers is high. The friction created by the opposing movement of the subcutaneous layers can mechanically deform and damage these sweat glands and also generate frictional heat in an amount sufficient to disable or ablate at least one sweat gland within the target tissue. The amount of frictional heat generated will depend on a number of factors, including, speed and power of paddle movement, frequency of paddle oscillation, the contact force between abutting subcutaneous layers and the adhesion force of the paddle elements 1221 with the skin surface.

Figure 49:
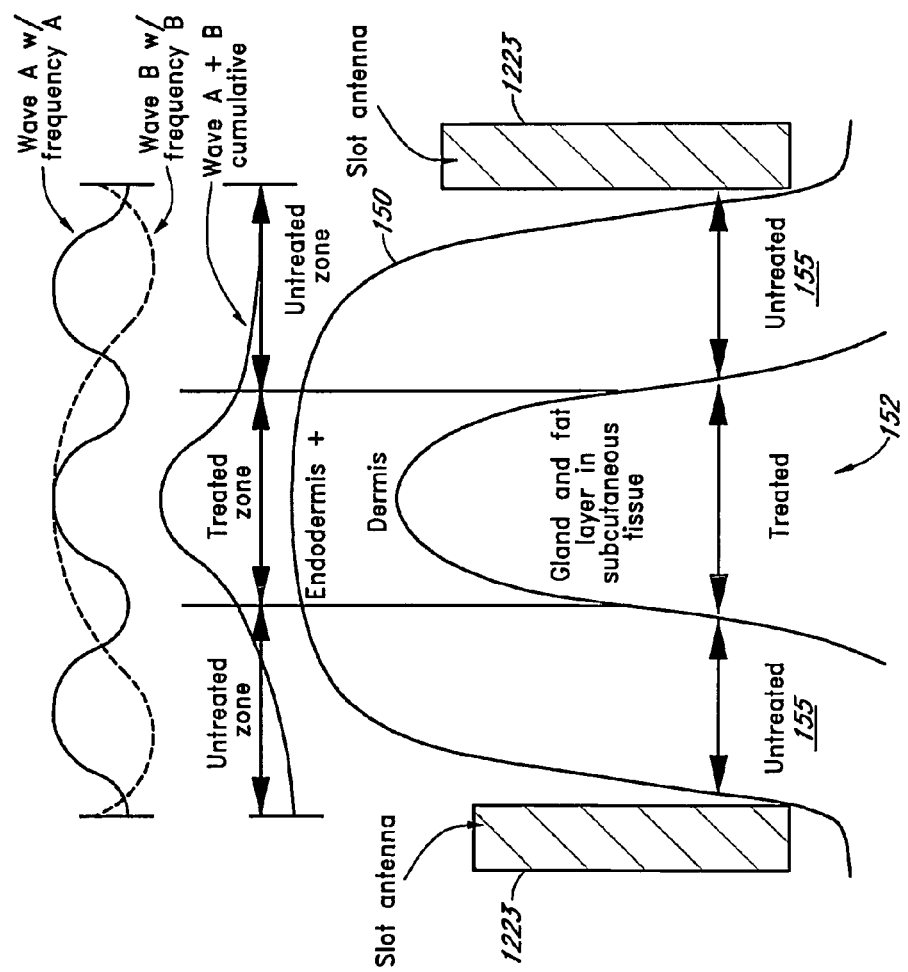
FIG. 49 shows a skin fold being treated by two ultrasonic transducers positioned on two sides of the skin fold according to one embodiment.
Figure 50:
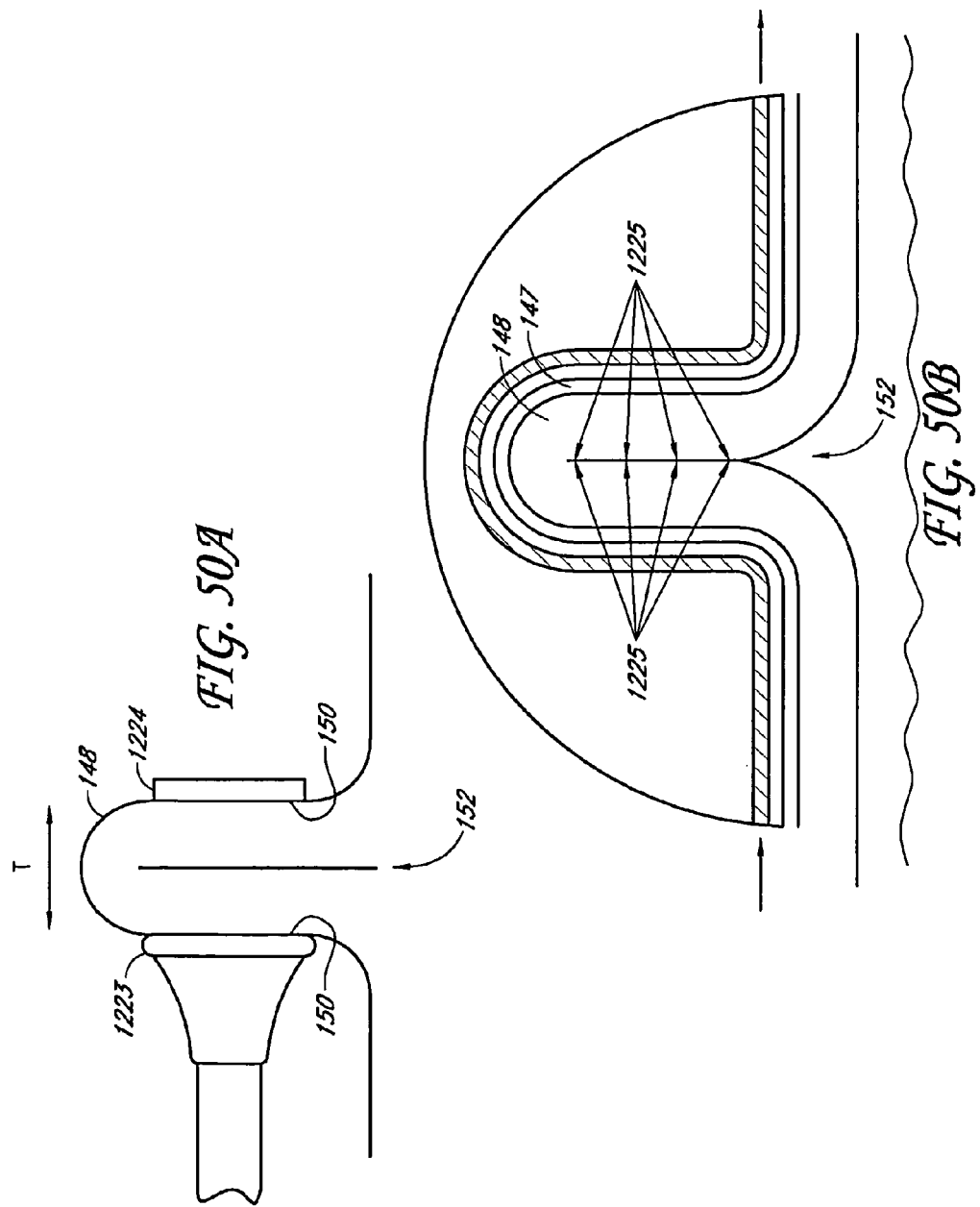
FIG. 50A shows an ultrasonic delivery instrument used to deliver ultrasound treatment on one side of a skin fold according to one embodiment.
FIG. 50B shows light energy being radiated to the skin fold from one energy source according to one embodiment.

In another embodiment employing the skin fold geometry, treatment can be concentrated and localized at the target tissue using focused ultrasound. As illustrated in FIG. 49, ultrasonic transducers 1223 can be used to deliver continuous ultrasound treatment from both sides of the skin fold 150 using one or more channels. The energy waves from each transducer 1223 can be phased such that the wave from one transducer 1223 can harmonize with the wave from the other transducer 1223 and yield a cumulative treatment effect at the zone of target tissue 152. The waves can also be synchronized such that they cancel one another out in areas where treatment is not desired (i.e., non-target tissue 155). Accordingly, the optimal ultrasound treatment would comprise transducers configured and coordinated to deliver energy waves that are additive at the target tissue dense region but subtractive at other regions. In this embodiment, energy waves can be delivered with frequencies from about 20 kHz to 18 MHz and powers from about 0 W/cm² to 50 W/cm². More specifically, treatment may be most effective at frequencies from about 0.5 MHz to 3 MHz and powers from about 720 mW/cm² to 50 W/cm².

Another embodiment utilizing ultrasound energy and the skin fold geometry is shown in FIG. 50A. In this embodiment, a transducer 1223 is located on one side 150 of the skin fold and a reflector 1224 is used on the other side 150 of the skin fold instead of a transducer 1223. As discussed above, the parameters of the remaining transducer 1223 can be set such that the propagated wave reaches its peak amplitude at the point it reaches the treatment zone 152 within the fold 148. In this embodiment, the frequency of the transducer's wave and position and angle of the reflector 1224 on the opposite side of the skin fold 148 can be matched to create a resonant frequency, wherein the wave that is reflected back through the skin fold by the reflector 1224 is virtually identical to the initial wave. Accordingly, the treatment zone 152 receives a cumulative treatment despite the use of only one transducer 1223. Additionally, the use of a reflector 1224 may provide the added benefit of preventing ultrasound waves from straying from the treatment site and doing damage to non-target structures elsewhere in the body.

Many skin treatments using light energy are unable to deliver maximum energy because the water in the blood of the skin tissue absorbs much of the energy. The embodiment illustrated in FIG. 50B provides a means for minimizing water absorption of delivered energy. In this embodiment, light energy 1225 is configured to be non-invasively delivered to the treatment zone 152 and absorbed by the target tissue 152 to yield a treatment effect. In some embodiments, near infrared light is selected at a wavelength off-peak of the highest water absorption frequency such that minimal light is absorbed by the blood and a significant amount of energy penetrates into the treatment zone. In one embodiment, the energy can be delivered at a wavelength from about 1300 to 1600 nanometers. In another embodiment, the energy wavelength can be from about 1400 to 1450 nanometers.

In one embodiment of the approach illustrated in FIG. 50B, the light energy 1225 can be radiated to the skin fold 148 from one energy source. Energy penetration associated with this treatment, and the resulting treatment effect, can be enhanced by increasing its spot size and optical fluence. In another embodiment, the light energy 1225 can come from multiple sources that are focused on the treatment zone 152, such that the energy from multiple sources converges to the treatment zone 152. In addition to near infrared, some of the various energy types that can be employed in this configuration include, but are not limited to, infrared and IPL. Although the embodiment shown in FIG. 50B discloses administering light energy 152 treatment to skin fold 148 geometry, this treatment can also be administered using a planar geometry. One benefit of using a folded or pinched skin geometry is that some of the blood within the microvasculature of the skin fold 148 will have been forced out of the fold tissue, making the tissue more transparent to the light energy 1225. This benefit will be greater in the presence of vacuum pressure, as shown in FIG. 50B, since the vacuum 147 will facilitate the evacuation of blood from the skin fold.

It may be desirable to thermally protect non-target tissue in embodiments disclosed herein relating to administering thermal treatment employing the skin fold geometry. Thermal protection can be particularly helpful with this geometry because protection can be applied to non-target tissue from either side of the skin fold as well as from the top of the skin fold. For example, for treatments where an energy delivery device is configured to deliver thermal energy to the target tissue in the zone of treatment, cooling elements can be used at either side of the fold and at the top of the fold to protect non-target tissue and localize the heat treatment to the target tissue. The cooling elements can also be incorporated into the stabilizer plates on either side of the fold that are used to maintain the fold during treatment.

Figure 51:
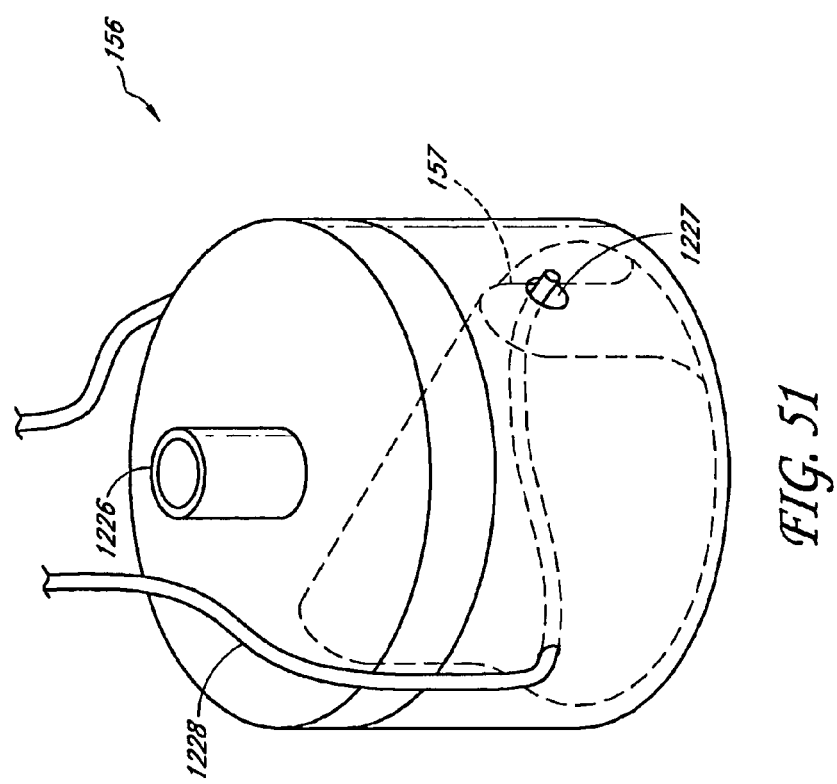
FIG. 51 shows a perspective view of a suction electrode comprising a housing, a tissue chamber, a vacuum port and electrodes according to one embodiment.

As mentioned with respect to many of the embodiment discussed above, it may be desirable to create the skin fold with the assistance of suction. For example, a suction-vacuum cavity can be incorporated into any of the aforementioned devices. FIG. 51 shows a suction electrode 1226 comprising a housing 156, a tissue chamber 157, a vacuum port (not shown) for connection to a vacuum source (not shown) and electrodes 1227 connected by leads 1228 to a power source. The vacuum source can be configured for providing sufficient vacuum force to grasp and hold the skin in a folded orientation within the tissue chamber 157. The device may utilize the suction 1226 for simply grasping the skin at the beginning of the procedure or holding the skin in place for some or all of the treatment. This area of lower pressure or suction within the device 1226 will help adhere the device 1226 to the skin, bringing the target tissue into closer apposition to the electrode antenna 1227, and reduce blood flow in the target tissue, thereby enabling more efficient heating of the tissue.

Additionally, suction may help to control pain by triggering stretch and pressure receptors in the skin, thereby blocking pain signals via the gate control theory of pain management. The gate control theory holds that an overabundance of nerve signals arriving at the dorsal root ganglion of the spinal cord will overwhelm the system, and mask or block the transmission of pain receptor signals to the brain. This mechanism of pain management is exploited by implantable electrical pain controls units, TENS systems, the Optilase system and others.

Figure 52A:
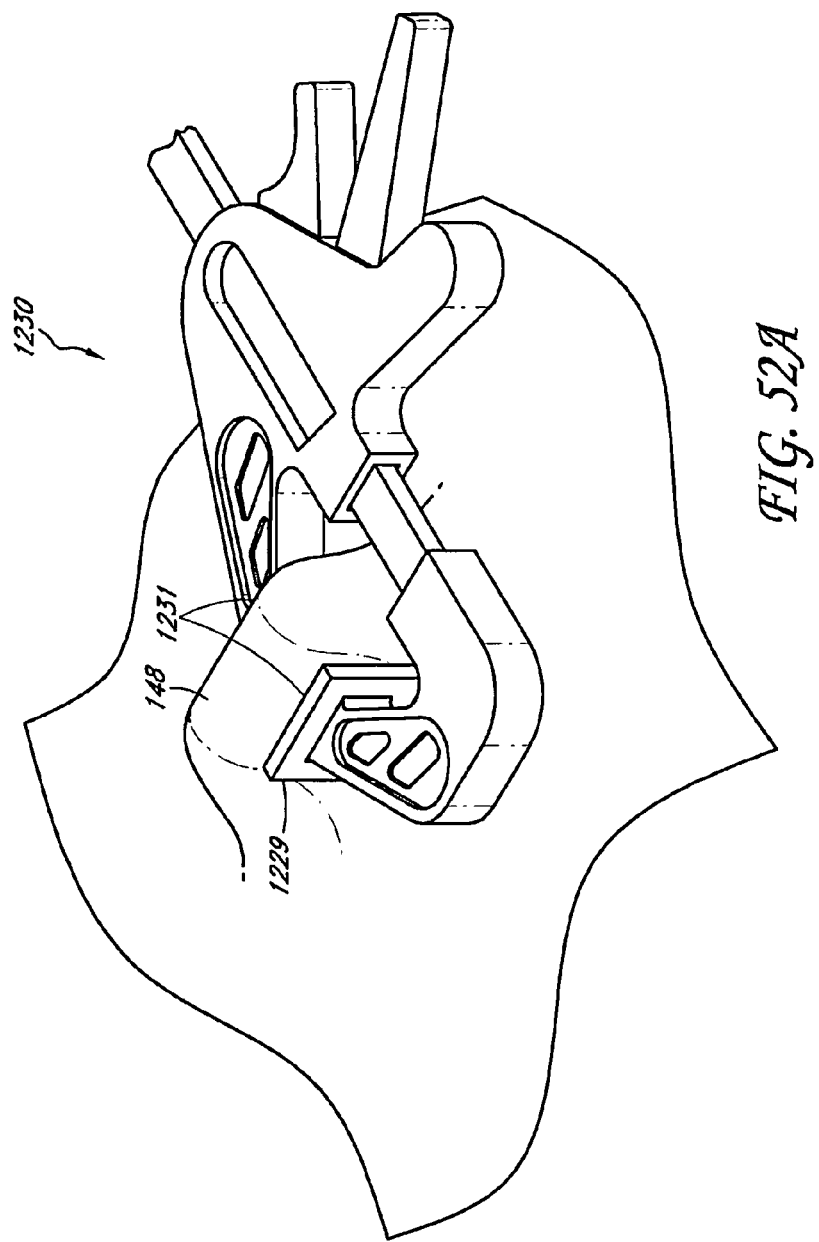
FIG. 52A shows a perspective view of a clamp used to create and hold a skin fold according to one embodiment.
Figure 52C:
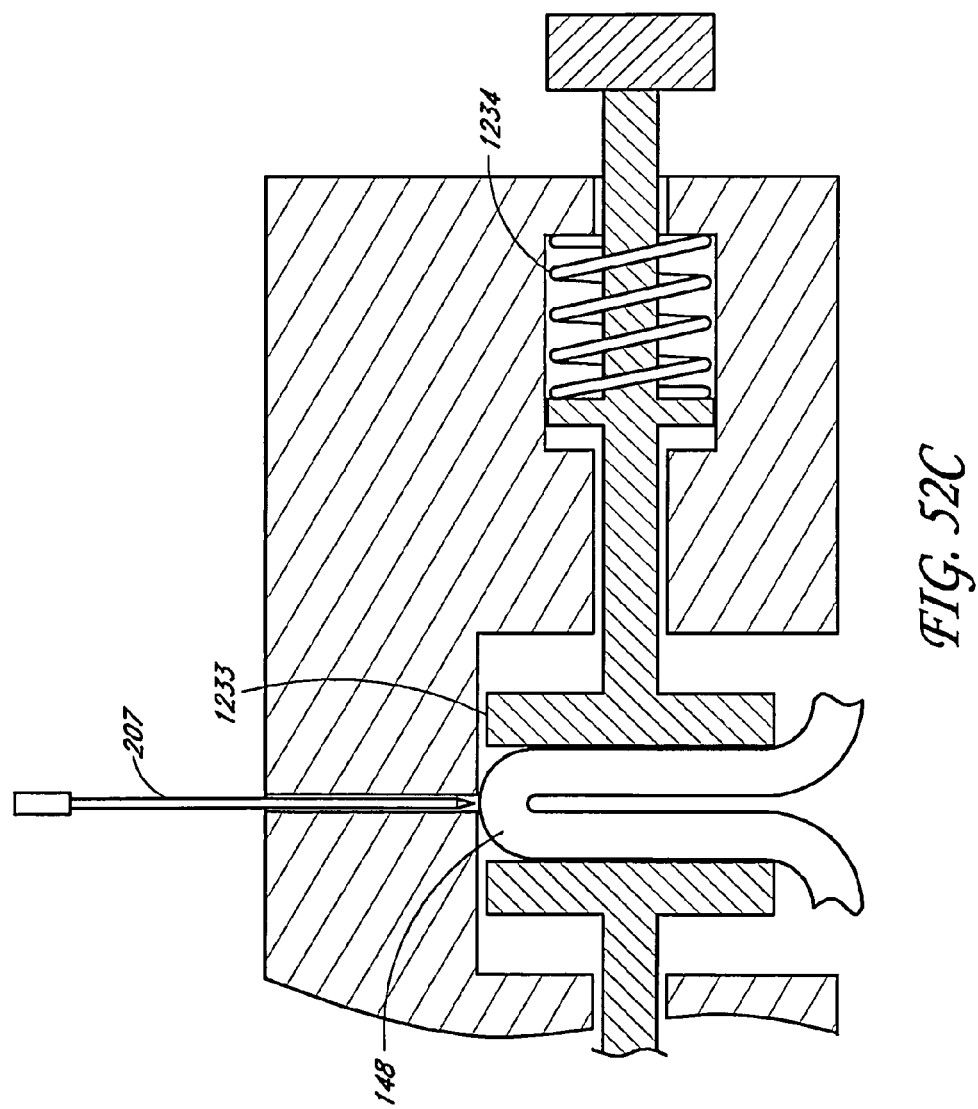
FIG. 52C shows a side view of the clamp of used to create and hold a skin fold according to a third embodiment.

FIGS. 52A, 52B and 52C illustrate alternatives embodiment where a clamp 1229 is used to create and hold the skin fold 148. As illustrated in FIG. 52A, a device 1230 comprising an insulated clamp 1229 and conductive metal plates 1231 is used to deliver treatment to the skin fold 148 treatment. The metal plates 1231 are electrically connected to a power source for delivering energy to the target tissue within the skin fold 148. Conductive gel can be optionally used to ensure contact and that energy is properly delivered to the target tissue. Alternatively, the embodiments depicted in FIGS. 52B and 52C show a minimally-invasive treatment wherein the skin fold 148 is maintained by stabilizer plates 1232 on either side of the fold 148 while a needle 207 referenced to the stabilizer plates 1232 is inserted through the top of the fold 148 to deliver treatment. The stabilizer plates 1233 in the embodiment in FIG. 52C are spring-loaded with one or more springs 1234 to maintain the fold during treatment. Other non-limiting examples of tissue acquisition systems, devices, and methods that can be used with embodiments described herein are disclosed, for example, at pp. 69-71 of U.S. Provisional Application No. 61/045,937, previously incorporated by reference in its entirety.

iii. Enhancements

1. Medications

In many of the treatments disclosed herein, the target tissue is damaged to yield a treatment effect. However, non-target tissue may also be affected in some of these treatments. Such treatments may have complications such as pain, inflammation, infection, and scarring, which may occur both during and after treatment. Therefore, it may be beneficial to provide the patient with medications prior to, during and/or after the treatment to minimize the incidence and impact of these complications. The medications, which could be anesthetics for pain, steroids for inflammation and antibiotics for infection, can be administered orally, topically or via local injection.

2. Imaging

For any of the embodiments disclosed herein, it may be desirable to administer treatment with the assistance of diagnostic medical imaging technology. For example, high resolution imaging such as ultrasound, magnetic resonance imaging (MRI) and optical coherence tomography (OCT) can be used to locate, identify and visualize the target tissue before, during and after treatment is administered to optimize the efficacy of the treatment. Alternatively, imaging can be used in combination with other diagnostic techniques to identify the target tissue for treatment or determine treatment efficacy. For example, iodine staining can be used to determine the location of where a patient is sweating following treatment.

3. Controlled Energy Delivery w/Physiological Feedback Loop

With some of the treatments disclosed herein for delivering energy to target tissue, controlled delivery of energy may be helpful in avoiding unnecessary damage to target tissue (e.g., desiccation, charring, etc.) and non-target tissue as a result of overheating. A controlled delivery of energy may also result in a more consistent, predictable and efficient overall treatment. Accordingly, it may be beneficial to incorporate into the energy delivery system a controller having programmed instructions for delivering energy to tissue. Additionally, these programmed instructions may comprise an algorithm for automating the controlled delivery of energy.

In an embodiment employing the controlled delivery of energy, the aforementioned controller can be incorporated into or coupled to a power generator, wherein the controller commands the power generator in accordance with a preset algorithm comprising temperature and/or power profiles. These profiles may define parameters that can be used in order to achieve the desired treatment effect in the target tissue. These parameters may include, but are not limited to, power and time increments, maximum allowable temperature, and ramp rate (i.e., the rate of temperature/power increase). Feedback signals comprising real-time or delayed physiological and diagnostic measurements can be used to modulate these parameters and the overall delivery of energy. Among the measurements that can be taken, temperature, impedance and/or reflected power at the treatment site and/or target tissue can be particularly useful. These measurements may help monitor the effect that the energy delivery has at the treatment site and at the target tissue over the course of the treatment. The energy controller may have fixed coefficients or the controller coefficients may be varied depending upon the sensed tissue response to energy delivery. Additionally, an algorithm comprising a safety profile may be employed to limit energy delivery or to limit sensed tissue temperature. These algorithms could shut off energy delivery or modulate the energy delivery. Additionally, in treatments where thermal protection is employed, such as an active cooling element, the protective cooling can be modulated based on the monitored data.

By considering temperature measurements in the delivery of energy, treatment can be administered to achieve the necessary treatment effect while avoiding unnecessary complications of the treatment. For example, energy delivery to target tissue can be steadily increased (i.e., ramped up) until the desired threshold temperature is reached for the target tissue, wherein the threshold temperature is that which is necessary to yield a treatment effect. By ceasing the power increase, or the delivery of energy altogether, once the threshold temperature is reached, harm to non-target tissue resulting from additional and excessive heating can be avoided.

Temperature can be measured using any number of sensors, including thermocouples and thermistors, wherein such sensors can be incorporated into the energy delivery element, the energy delivery device and/or the energy delivery system. For example, in an RF energy delivery system, a thermocouple can be imbedded in the electrode that delivers the RF energy, positioned adjacent to the electrode as part of the energy delivery device or located separate from the device such that the thermocouple is wired directly to the generator. The temperature measured can be that of the tissue immediately adjacent the device, the target tissue or any other tissue that may provide useful temperature measurements. In cases where the energy delivery element is in thermal communication with the surrounding tissue (e.g., via conduction), a sensor that is incorporated into the energy delivery element may measure the temperature of the element itself.

Impedance can be measured by observing a tissue's response to electrical stimulation. This measurement is useful because it can help assess the extent of energy delivery to and through tissue. For example, energy that is directed to tissue having high impedance may have difficulty infiltrating deeper regions of tissue. This is particularly important in the case of skin tissue, as the impedance of skin can change over the course of treatment. As tissue is heated, it loses moisture and its conductivity drops and impedance increases. If the tissue is heated until it is desiccated, the resistivity of the tissue may impair energy delivery to surrounding tissue via electrical conduction. Employing impedance measurement feedback in the energy delivery system can optimize the delivery of energy to target tissue while avoiding adverse consequences to target and non-target tissue.

FIG. 53 shows another embodiment relating to the controlled delivery of energy to target tissue. In this embodiment, an array of electrodes 1235 can be configured such that they are sequentially activated as adjacent bipolar pairs (e.g., 1236, 1237). For example, the first electrode 1236 is the positive pole and the second electrode 1237 in the negative pole in the first activation. In the second activation, the second electrode 1237 serves as the positive pole and the third electrode 1238 is the negative pole. A treatment effect can therefore be achieved between the first 1236 and second 1237 electrode, the second 1237 and third 1238 electrode, the third 1238 and fourth 1239 electrode and the fourth 1239 and fifth 1240 electrode. Additionally, since only one electrode pair is activated at a time, each treatment in the sequence can be customized based on the characteristics of the tissue being treated. For example, if the impedance between the first 1236 and second 1237 electrodes is higher than the impedance between the second 1237 and third 1238 electrodes, the first treatment may be applied for a longer duration than the second treatment. This results in a higher resolution per activation and a more accurate overall treatment.

4. Staged Treatment

Figure 54:
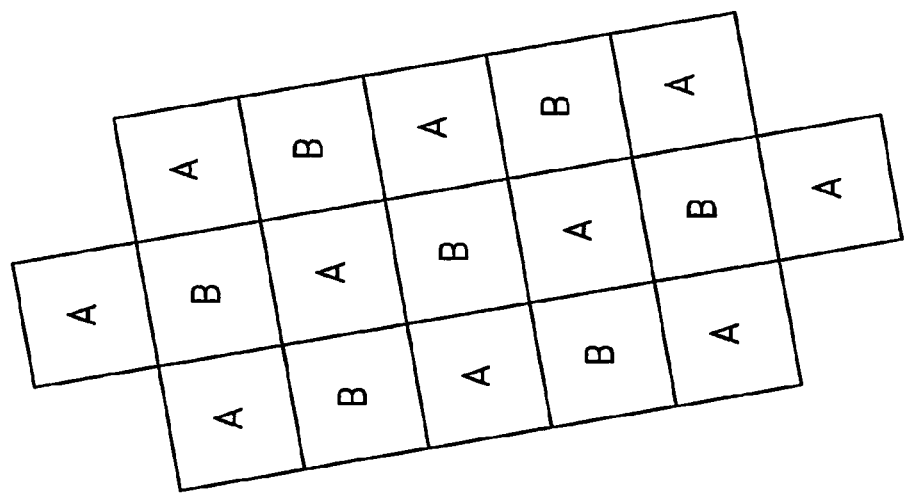
FIG. 54 shows one embodiment of a representative grid indicating target treatment sites "A" and target treatment sites "B" that could be used over a skin area to identify specific areas of treatment.
Figure 55B:
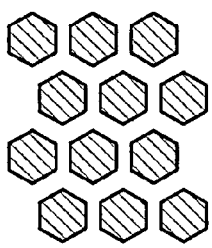
FIG. 55A-E show a variety of patterns illustrating specific areas of treatment and non-treatment sites that could be used over an area of skin.
Figure 55D:
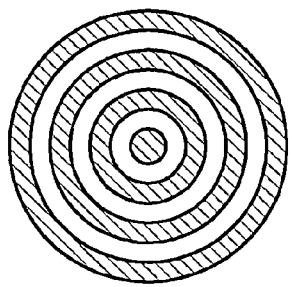
Figure 55A:
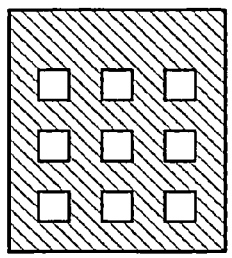
Figure 55C:
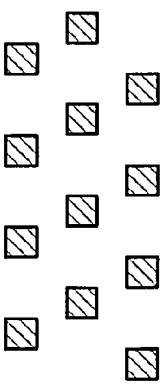
Figure 55E:

In many of the treatments disclosed in this specification, it may desirable to perform the treatment in stages. Additionally, the treatment can be patterned such that sections of target tissue are treated in the initial stage while other sections are treated in subsequent stages. For example, as illustrated in FIG. 54, a patient could have the regions marked "A" treated in a first stage and the regions marked "B" treated in a second stage. Additionally, the treatment could be broken down into further stages and additional regions. Optionally, treatment could be administered to the same regions in multiple stages such that each region receives treatment multiple times. In one embodiment, in subsequent stages the treatment to a particular region may vary, such as with an increased or decreased amount of energy, or with a different treatment type.

This approach has numerous potential benefits. First, a staged treatment gives the body the opportunity to heal between treatments. This is particularly important since treating or thermally damaging discrete regions of tissue over several sessions will likely have fewer and less severe complications compared to treating or thermally damaging a relatively large area of tissue in one session. Secondly, a patterned treatment having small regions of treatment will elicit a more favorable healing response. Since healing time is related to the distance that fibroblasts must migrate from surrounding tissue, smaller treatment areas heal much faster than larger treatment areas. FIGS. 55A-E illustrate examples of various patterned treatments.

For the medical practitioner, a staged and patterned treatment will provide the opportunity to track the treatment's efficacy and provide follow-up treatments tailored to the patient's specific needs. For example, in the case of treatments for axillary hyperhidrosis, the clinician can have follow-up sessions where sweating is mapped (e.g., iodine staining) to (1) identify the remaining areas for treatment and (2) determine the overall reduction in sweating in the underarm area. For patients who do not necessarily desire 100% anhidrosis, a staged treatment may allow them to discontinue treatment at a particular point. For example, a patient suffering from a severe case of axillary hyperhidrosis may be satisfied with a 70% reduction in sweating and may only wish to participate in the number of treatments necessary for such reduction.

Additionally, a staged and patterned treatment can minimize the body's contracture response during the healing process. In a process called fibrosis (or scarring), fibroblasts lay down a mesh of collagen to facilitate the healing of tissue. As the density of the scar increases, the treated area contracts, thereby tightening the skin within that region. In the case of treatments for axillary hyperhidrosis, contracture could potentially impair the patient's full range of arm motion. A treatment can be patterned and staged to minimize contracture and/or its impact on the patient. For example, the slender treatment areas depicted in FIG. 55C would result in minimal axillary contracture and resulting impairment to range of arm motion.

A template can be used to facilitate the application of a staged and/or patterned treatment. FIG. 56 illustrates a staged treatment series comprising three templates 158, 159, 160, wherein each template is configured to allow treatment to a different portion of the overall treatment area. The template may be configured to engage the energy delivery device or one or more energy delivery elements to facilitate the application of a staged and/or patterned treatment. The template can be comprised of a single frame made from a wood, plastic or metal with removable or adjustable pieces to reflect the desired pattern and/or stage. Alternatively, the template can also be a pattern that is drawn on the patient's skin using a temporary marker, tattoo or dye (e.g., henna) that will remain over the course of multiple staged treatments.

Figure 57:
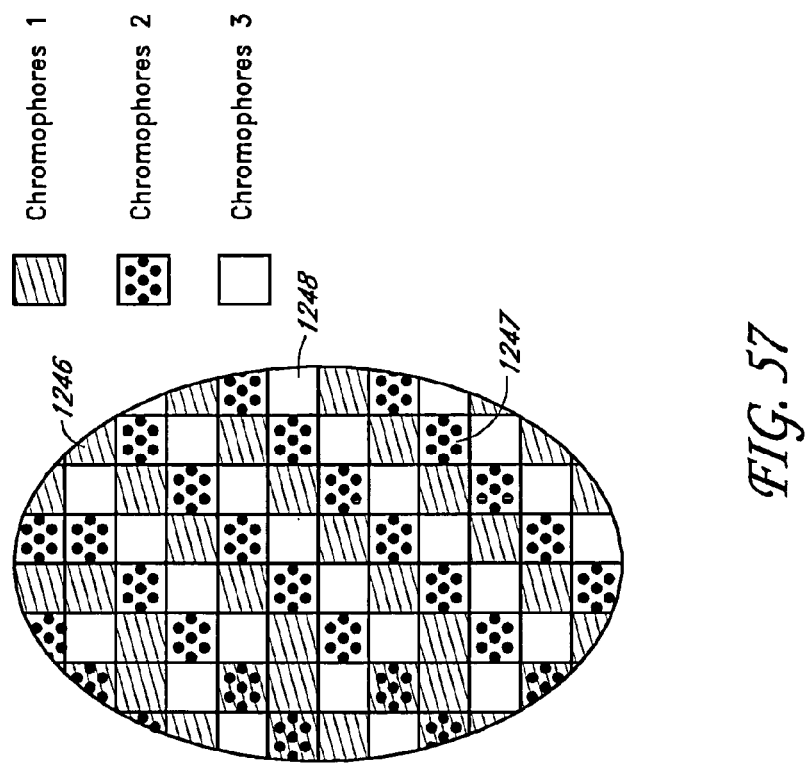
FIG. 57 shows a single template pattern represented by different chromophores corresponding to different stages of treatment according to one embodiment.

In another embodiment, as illustrated in FIG. 57, the template pattern can be represented by different chromophores 1246, 1247, 1248 corresponding to different stages of the treatment. For example, different chromophores 1246, 1247, 1248 can be injected into the patient's skin prior to any treatment such that each chromophore 1246, 1247, 1248 and the regions colored by such chromophore 1241 corresponds to one treatment stage. Once all regions have been appropriately colored, laser treatment can commence. At each stage of treatment, the treatment area is irradiated with a different laser, wherein the wavelength of each laser is specifically matched to the absorption characteristics of a different chromophore region.

In another application employing the color-coordinated template described above, the energy delivery device, energy applicator or energy delivery element may comprise this template. For example, in the intact microneedle configuration illustrated in FIG. 16, a patch of chromophore-tipped microneedles 239 can be configured with selective coloring in accordance with the above color-coordinated template. The same patch can be used at each treatment stage, wherein different treatments are administered by irradiating the patch with lasers of different wavelengths.

5. Diagnosis

Embodiments of the present invention also include methods and apparatuses for identifying and diagnosing patients with hyperhidrosis. Such diagnosis can be made based on subjective patient data (e.g., patient responses to questions regarding observed sweating) or objective testing. In one embodiment of objective testing, an iodine solution can be applied to the patient to identify where on a skin surface a patient is sweating and not sweating. For example, U.S. Pat. No. 4,190,056 to Tapper et al., which is hereby incorporated herein by reference in its entirety, describes methods and means for recording sweat gland activity. Moreover, particular patients can be diagnosed based on excessive sweating in different parts of the body in order to specifically identify which areas to be treated. Accordingly, the treatment may be applied only selectively to different parts of the body requiring treatment, including, for example, selectively in the hands, armpits, feet and/or face.

6. Quantifying Treatment Success

Following completion of any of the treatments described above, or any stage of a treatment, the success can be evaluated qualitatively by the patient, or may be evaluated quantitatively by any number of ways. For example, a measurement can be taken of the number of sweat glands disabled or destroyed per surface area treated. Such evaluation could be performed by imaging the treated area or by determining the amount of treatment administered to the treated area (e.g. the quantity of energy delivered, the measured temperature of the target tissue, etc.). The aforementioned iodine solution test may also be employed to determine the extent of treatment effect. In addition, a treatment can be initiated or modified such that the amount of sweating experienced by a patient may be reduced by a desired percentage as compared to pre-treatment under defined testing criteria. For example, for a patient diagnosed with a particularly severe case of hyperhidrosis, the amount of sweating may be reduced by about 10%, 20%, 30%, 40%, 50%, 60%, 70%, 80%, 90% or more. For a patient diagnosed with a less severe or more normal sweating profile, a step-wise reduction of sweating may be achieved, but with less resolution. For example, such a patient may only be able to achieve partial anhidrosis in 25% increments.

Overview of Certain Methods, Systems and Other Embodiments

In one embodiment, the present application provides a method related to treating a patient comprising identifying a patient having a condition of excessive sweating, wherein the patient desires that sweating be reduced on at least a portion of the patient's body; positioning an energy delivery device proximate to a skin tissue of the patient; and delivering energy to a sweat gland of the patient sufficient to halt the secretion of sweat by at least partially disabling or destroying the sweat gland.

In one embodiment, positioning an energy delivery device may further comprise positioning proximate to the skin tissue of the patient an energy delivery element selected from the group consisting of an electrode, antenna, ultrasound transducer, laser, light emitting diode, light bulb cryogenic probe and combinations thereof. In one embodiment, delivering energy to a sweat gland of the patient may further comprise delivering energy to the sweat gland selected from the group consisting of electromagnetic, x-ray, radiofrequency, microwave, ultrasound, near infrared, infrared, intense pulsed light, visible light and laser and combinations thereof. Delivering energy to a sweat gland of the patient may further comprise heating the sweat gland, wherein heating the sweat gland may further comprise at least partially ablating the sweat gland.

In one embodiment, positioning an energy delivery device may further comprise inserting the energy delivery device within the skin tissue. In one embodiment, inserting the energy delivery device within the skin tissue may further comprise inserting the energy delivery device into the skin tissue to a depth ranging from about 1 mm to about 8 mm beneath the surface of the skin. Inserting the energy delivery device within the skin tissue may further comprise inserting in the skin tissue an interstitial device selected from the group consisting of needles, stylets, catheters, probes and microneedles.

In one embodiment, the method may further comprise providing protective cooling to the skin tissue. Providing protective cooling to the skin tissue may further comprise positioning a cooling element proximate the skin tissue.

In one embodiment, the method may further comprise administering to the patient a medication selected from the group consisting of anesthetics, steroids, and antibiotics. Administering medication to the patient may further comprise administering the medication orally, topically or via injection.

In one embodiment, the method may further comprise visualizing the sweat gland using medical diagnostic imaging.

In one embodiment, the method may further comprise monitoring a diagnostic parameter of the skin tissue. The diagnostic parameter may be selected from the group consisting of impedance, temperature, reflected light and reflected power.

In one embodiment, delivering energy to a sweat gland of the patient may further comprise modulating energy delivery in response to a monitored diagnostic parameter.

In one embodiment, the method may further comprise quantifying the reduction of sweating achieved in the patient or the treated portion of the patient's body.

In accordance with the method, a patient may desire that sweat be reduced on at least a portion of the patient's body including at least a portion of the patient's axillae.

In one embodiment, the method may further comprise elevating the skin tissue away from the underlying tissue prior to delivering energy to the sweat gland.

In one embodiment, provided is a method related to treating a patient for a condition of hyperhidrosis comprising identifying an area of skin tissue on a patient comprising a layer of sweat glands, wherein the area of skin tissue produces excessive sweat relating to the hyperhidrosis; grasping the area of skin tissue to form a skin fold comprising a first side and a second side, wherein the layer of sweat glands corresponding to the first side is adjacent to the layer of sweat glands corresponding to the second side such that the layers comprise a treatment zone; and delivering energy to the treatment zone to yield a treatment effect, said treatment effect reducing the amount of sweating from the area of skin tissue.

In one embodiment, the method may further comprise applying protective cooling to at least a portion of the area of skin tissue.

In one embodiment, applying protecting cooling to at least a portion of the area of skin tissue may further comprise positioning a cooling element proximate the skin fold. Positioning a cooling element proximate the skin fold may further comprise positioning a first cooling element proximate the first side of the skin fold and a second cooling element proximate the second side of the skin fold.

In one embodiment, grasping the area of skin tissue to form a skin fold may further comprise providing suction to the area of skin tissue. Providing suction to the area of skin tissue may further comprise maintaining suction to the area of skin tissue during the treatment.

In one embodiment, provided is a method related to reducing sweating in a patient comprising elevating a skin tissue of the patient, wherein the skin tissue comprises a target tissue comprising at least one sweat gland; and delivering energy to the target tissue, said delivery of energy at least partially disabling or destroying the at least one sweat gland to reduce sweating from the skin tissue of the patient.

In one embodiment, delivering energy to the target tissue may further comprise positioning an energy delivery device proximate to the skin tissue of the patient. In one embodiment, positioning an energy delivery device may further comprise positioning proximate to the skin tissue of the patient an energy delivery element selected from the group consisting of an electrode, antenna, ultrasound transducer, laser, light emitting diode, light bulb cryogenic probe and combinations thereof. In another embodiment, positioning an energy delivery device may further comprise inserting the energy delivery device within the skin tissue. Inserting the energy delivery device within the skin tissue may further comprise positioning an insertion element energy delivery element proximate to the target tissue.

In one embodiment, the energy delivery element may be selected from the group consisting of an electrode, antenna, ultrasound transducer, laser, light emitting diode, light bulb and combinations thereof.

In one embodiment, elevating the skin tissue may further comprise applying suction to the skin tissue.

In one embodiment, the method may further comprise providing protective cooling to the skin tissue. Providing protective cooling to the skin tissue may further comprise positioning a cooling element proximate the skin tissue.

In one embodiment, delivering energy to the target tissue may further comprise delivering energy to a first portion of the target tissue at a first time and delivering energy to a second portion of the target tissue at a second time. The first time and second time may be separated by a predetermined period of time. The predetermined period of time may be selected from the group consisting of 1-7 days, 1-4 weeks, and 1-4 months.

In one embodiment, provided is an apparatus related to treating a sweat gland of a patient comprising an energy generator and an energy delivery device configured for placement proximate a skin tissue of the patient, wherein the energy delivery device is coupled to the energy generator, and wherein the energy delivery device is configured to deliver energy to a target tissue within the skin tissue sufficient to at least partially destroy or disable at least one sweat gland within the target tissue.

In some embodiments, the energy delivery device may be configured for insertion into the target tissue.

In some embodiments, the energy delivery device may comprise at least one energy delivery element selected from the group consisting of electrodes, antennas, ultrasound transducers, lasers, light emitting diodes, light bulbs, cryogenic probes, and combinations thereof.

In one embodiment, the first apparatus may further comprise a cooling element configured for placement proximate a non-target tissue of the patient.

In one embodiment, the first apparatus may further comprise a suction device configured for placement proximate the skin tissue of the patient.

In one embodiment, the present application provides a second apparatus related to treating a target tissue of a patient comprising an interstitial device comprising at least one needle configured for insertion proximate to the target tissue of the patient and a light energy source configured for transmitting light energy to the interstitial device, wherein the needle is configured for receiving the light energy transmitted by the light energy source.

In one embodiment, the chromophore may generate thermal energy from the light energy absorbed from the light energy source. The chromophore may generate thermal energy from the light energy absorbed from the light energy source. The thermal energy from the chromophore may cause a treatment effect to the target tissue. In one embodiment, the treatment effect to the target tissue may comprise heating the target tissue. In another embodiment, the treatment effect to the target tissue may further comprise at least partially ablating the target tissue. In yet another embodiment, the treatment effect to the target tissue may further comprise at least partially disabling at least one target structure selected from the group consisting of sweat glands, hair follicles, sebaceous glands, collagen and fat.

In some embodiments, the interstitial device may further comprise a microneedle patch having an optically neutral backing.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the claims use the word "or" in reference to a list of two or more items, that word covers all of the following interpretations of the word: any of the items in the list, all of the items in the list, and any combination of the items in the list.

The above detailed descriptions of embodiments of the invention are not intended to be exhaustive or to limit the invention to the precise form disclosed above. Although specific embodiments of, and examples for, the invention are described above for illustrative purposes, various equivalent modifications are possible within the scope of the invention, as those skilled in the relevant art will recognize. For example, while steps are presented in a given order, alternative embodiments may perform steps in a different order.

The various embodiments described herein can also be combined to provide further embodiments. Related methods, apparatuses and systems utilizing microwave and other types of therapy, including other forms of electromagnetic radiation, and further details on treatments that may be made with such therapies, are described in the above-referenced provisional applications to which this application claims priority, the entireties of each of which are hereby incorporated by reference: U.S. Provisional Patent Application Ser. No. 60/912,889, entitled "Methods and Apparatus for Reducing Sweat Production," filed Apr. 19, 2007, U.S. Provisional Patent Application Ser. No. 61/013,274, entitled "Methods, Delivery and Systems for Non-Invasive Delivery of Microwave Therapy," filed Dec. 12, 2007, and U.S. Provisional Patent Application Ser. No. 61/045,937, entitled "Systems and Methods for Creating an Effect Using Microwave Energy in Specified Tissue," filed Apr. 17, 2008. While the above-listed applications may have been incorporated by reference for particular subject matter as described earlier in this application, Applicants intend the entire disclosures of the above-identified applications to be incorporated by reference into the present application, in that any and all of the disclosures in these incorporated by reference applications may be combined and incorporated with the embodiments described in the present application.

In general, the terms used in the following claims should not be construed to limit the invention to the specific embodiments disclosed in the specification, unless the above detailed description explicitly defines such terms. While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

ADDITIONAL REFERENCES FOR INCORPORATION

The following references describe methods, devices and other embodiments that may be incorporated into or used in combination with the embodiments described in this application. Each of these references is incorporated by reference herein in their entirety:

Pressure-Induced Bullae and Sweat Gland Necrosis Following Chemotherapy Induction, *The American Journal of Medicine* (Sep. 15, 2004, Volume 117).

U.S. Pat. No. 5,190,518 to Takasu titled Surgical Device for the Treatment of Hyper Hidrosis.

U.S. Pat. No. 4,190,056 to Tapper et al. titled Method and Means for Recording Sweat Gland Activity.

U.S. Pat. No. 6,050,990 to Tankovich et al. titled Methods and Devices for Inhibiting Hair Growth and Related Skin Treatments.

A comparative study of the surgical treatment of axillary osmidrosis by instrument, manual and combined subcutaneous shaving procedures, Park et al., *Annals of Plastic Surgery*, Volume 41, November 1998, pg. 488-497.

Electrosurgery Using Insulated Needles: Treatment of Axillary Bromhidrosis and Hyperhidrosis by Kobayashi, *Journal of Dermatological Surgery and Oncology*, July 1988, pg. 749-752.

Selective sweat gland removal with minimal skin excision in the treatment of axillary hyperhidrosis: a retrospective clinical and histological review of 15 patients by Lawrence et al., *British Journal of Dermatology*, 2006, pg. 115-118.

U.S. Patent Application Publication No. US 2006/0111744 to Makin et al. titled Method and System for Treatment of Sweat Glands.

U.S. Patent Application Publication No. US 2003/0158566 to Brett titled Percutaneous Cellulite Removal System.

We claim:

1. An apparatus for treating a sweat gland of a patient comprising:

a microwave generator;

a grasping mechanism configured to grasp an area of skin tissue to form a skin fold having a first side and a second side;

a cooling element configured to apply protective cooling to at least a portion of the area of skin tissue; and first and second microwave antennas coupled to the microwave generator and associated with the grasping mechanism such that, when the skin fold is formed, the first microwave antenna is positioned on the first side of the skin fold and the second microwave antenna is positioned on the second side of the skin fold, wherein the first and second microwave antennas are configured to deliver microwave energy through the cooling element to the area of skin tissue to at least partially destroy or disable at least one sweat gland within the area of skin tissue.

2. The apparatus of claim 1, wherein the cooling element adapted to be positioned proximate to the skin fold when skin tissue is positioned in the grasping mechanism.

3. The apparatus of claim 1, wherein the cooling element comprises a first cooling element adapted to be positioned proximate the first side of the skin fold and a second cooling element adapted to be positioned proximate to the second side of the skin fold when skin tissue is positioned in the grasping mechanism.

4. The apparatus of claim 1, wherein the grasping mechanism comprises a suction mechanism configured to provide suction to the skin tissue when the skin tissue is positioned in the grasping mechanism.

5. The apparatus of claim 4, wherein the suction mechanism is configured to provide suction to the skin tissue to position the skin tissue in the grasping mechanism.

6. The method of claim 4, wherein the area of skin tissue comprises at least a portion of the axilla.

7. A method of treating a patient comprising:
identifying an area of skin tissue comprising a layer of sweat glands, wherein the area of skin tissue produces sweat;
grasping the area of skin tissue to form a skin fold, the skin fold comprising a first side and a second side, wherein, when folded the layer of sweat glands corresponding to the first side is proximally adjacent to the layer of sweat glands corresponding to the second side such that the layers comprise a treatment zone;
applying protective cooling with a cooling element to at least a portion of the area of skin tissue; and
positioning microwave antennas on the first and second sides of the skin fold and delivering microwave energy with the microwave antennas through the cooling element to the treatment zone to yield a treatment effect, said treatment effect reducing the amount of sweating from the area of skin tissue.

8. The method of claim 7, wherein applying protective cooling to at least a portion of the area of skin tissue further comprises positioning the cooling element proximate the skin fold.

9. The method of claim 8, wherein positioning the cooling element proximate the skin fold further comprises positioning a first cooling element proximate the first side of the skin fold and a second cooling element proximate the second side of the skin fold.

10. The method of claim 7, wherein grasping the area of skin tissue to form the skin fold further comprises providing suction to the area of skin tissue.

11. The method of claim 10, wherein providing suction to the area of skin tissue further comprises maintaining suction to the area of skin tissue during the treatment.

12. The method of claim 11, wherein the skin area of skin tissue is an area of the axilla.

* * * * *